United States Patent
Testa et al.

(10) Patent No.: US 11,369,577 B2
(45) Date of Patent: Jun. 28, 2022

(54) REPROGRAMMING-BASED MODELS OF NEURODEVELOPMENTAL DISORDERS AND USES THEREOF

(71) Applicants: IEO—Istituto Europeo di Oncologia S.r.l., Milan (IT); I.R.C.C.S. "Casa Sollievo della Sofferenza", San Giovanni Rotondo (IT); Università degli Studi di Milano, Milan (IT)

(72) Inventors: Giuseppe Testa, Milan (IT); Sina Atashpazgargari, Milan (IT); Antonio Adamo, Milan (IT); Pierre-Luc Germain, Milan (IT); Giuseppe Merla, Milan (IT); Giuseppe D'Agostino, Milan (IT); Matteo Zanella, Milan (IT)

(73) Assignees: IEO—Istituto Europeo di Oncologia S.r.l., Milan (IT); I.R.C.C.S. "Casa Sollievo della Sofferenza", San Giovanni Rotundo (IT); Università degli Studi di Milano, Milan (IT)

( * ) Notice: Subject to any disclaimer, the term of this patent is extended or adjusted under 35 U.S.C. 154(b) by 573 days.

(21) Appl. No.: 15/529,886

(22) PCT Filed: Nov. 25, 2015

(86) PCT No.: PCT/EP2015/077659
§ 371 (c)(1),
(2) Date: May 25, 2017

(87) PCT Pub. No.: WO2016/083458
PCT Pub. Date: Jun. 2, 2016

(65) Prior Publication Data
US 2019/0022027 A1    Jan. 24, 2019

Related U.S. Application Data

(60) Provisional application No. 62/085,176, filed on Nov. 26, 2014.

(51) Int. Cl.
| | | |
|---|---|---|
| *A61K 31/00* | (2006.01) | |
| *G01N 33/50* | (2006.01) | |
| *C12N 5/074* | (2010.01) | |
| *C12Q 1/6881* | (2018.01) | |
| *C12Q 1/6883* | (2018.01) | |
| *A61K 31/421* | (2006.01) | |

(Continued)

(52) U.S. Cl.
CPC ............ *A61K 31/00* (2013.01); *A61K 31/135* (2013.01); *A61K 31/421* (2013.01); *C12N 5/0696* (2013.01); *C12Q 1/6881* (2013.01); *C12Q 1/6883* (2013.01); *G01N 33/5058* (2013.01); *G01N 33/5073* (2013.01); *C12N 2501/06* (2013.01); *C12N 2501/115* (2013.01); *C12N 2501/13* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2501/727* (2013.01); *C12N 2503/00* (2013.01); *C12N 2503/02* (2013.01); *C12N 2506/1307* (2013.01); *C12N 2510/00* (2013.01); *C12N 2740/15041* (2013.01); *C12Q 1/6897* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 2004/0142859 A1* | 7/2004 | Steffan | ................... | A61K 31/19 514/310 |
| 2013/0035377 A1* | 2/2013 | Minucci | .................. | A61P 35/02 514/443 |

(Continued)

FOREIGN PATENT DOCUMENTS

| | | |
|---|---|---|
| EP | 2 743 256 B1 | 8/2012 |
| EP | 2 907 802 B1 | 10/2013 |

(Continued)

OTHER PUBLICATIONS

Atkinson et al. "Tranylcypromine: A review," Clinical Pharmacology and Therapeutics vol. 6, No. 5, pp. 631-655 (Year: 2013).*

(Continued)

*Primary Examiner* — Jeffrey S Lundgren
*Assistant Examiner* — Michael J Schmitt
(74) *Attorney, Agent, or Firm* — Knobbe, Martens, Olson & Bear, LLP

(57) ABSTRACT

The present invention relates to iPSC produced from fibroblast obtained from a subject affected by a neurodevelopmental disorder entailing intellectual disability (ID) and/or a disorder belonging to the Autism Spectrum Disorder (ASD) and/or Schizophrenia (SZ) and uses thereof. The present invention also relates to a cortical neural progenitor cell or a terminally differentiated cortical glutamatergic or gabaergic neuronal cell or a neural crest stem cell line, a mesenchymal stem cell line produced from the iPSC or iPSC line. The invention also relates to method for identifying a compound for the treatment and/or prevention of a neurodevelopmental disorder entailing intellectual disability (ID) and/or a disorder belonging to the Autism Spectrum Disorder (ASD) and/or Schizophrenia (SZ) and to a LSD1 inhibitor or a HDAC2 inhibitor for use in the treatment of such disorders.

Figure 1:
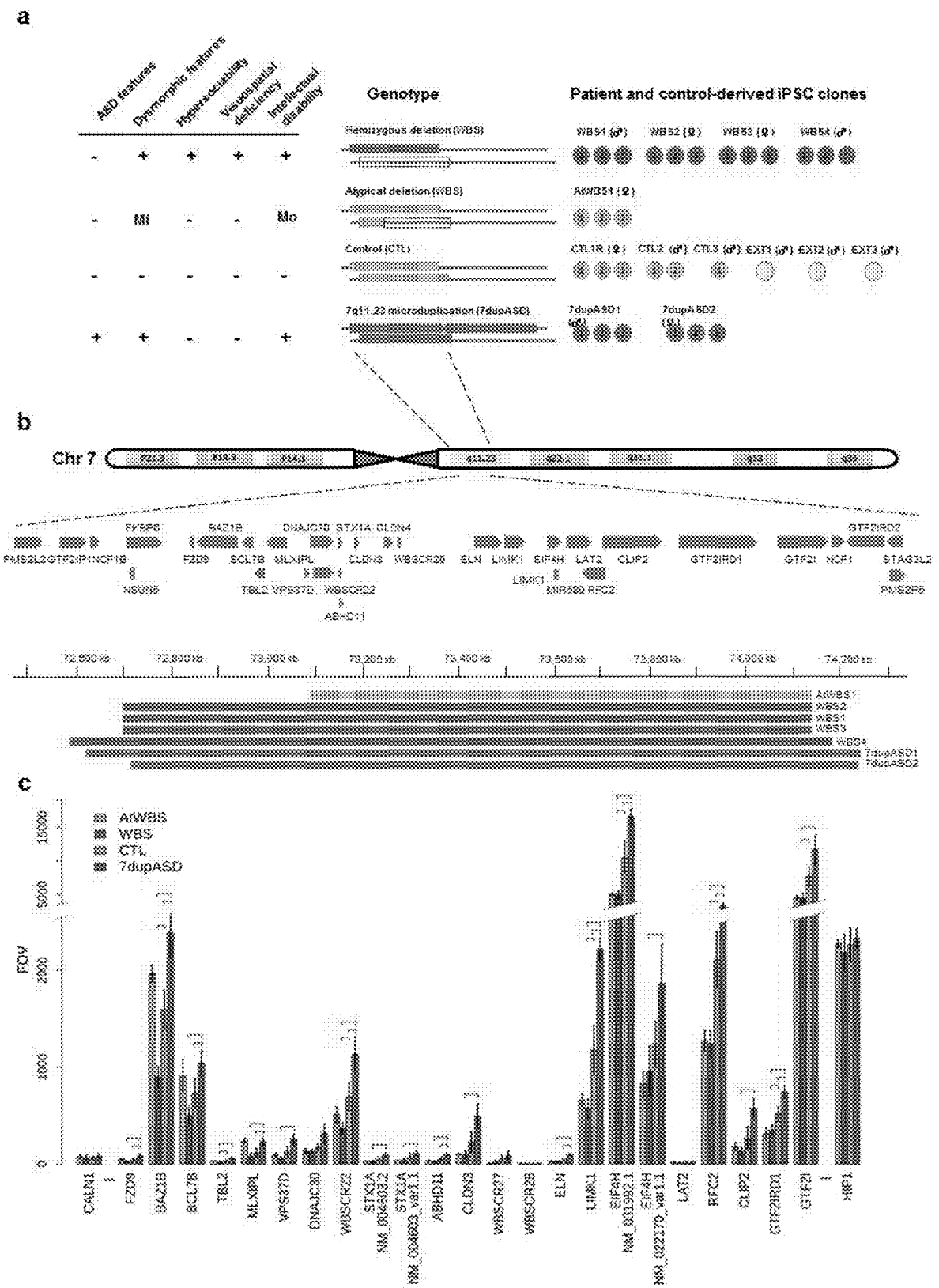

10 Claims, 20 Drawing Sheets
Specification includes a Sequence Listing.

(51) Int. Cl.
*A61K 31/135* (2006.01)
*C12Q 1/6897* (2018.01)

(56) References Cited

U.S. PATENT DOCUMENTS

2013/0149287 A1   6/2013  Livesey et al.
2014/0228405 A1*  8/2014  Tomita .................. A61K 31/366
                                                   514/329

FOREIGN PATENT DOCUMENTS

| WO | WO 2009/027349 A2 | 3/2009 | | |
|----|-------------------|--------|---|---|
| WO | WO 2012/156531 A3 | 11/2012 | | |
| WO | WO-2013057322 A1 * | 4/2013 | ........... | C07D 213/57 |
| WO | WO 2014/164867 A1 | 10/2014 | | |
| WO | WO 2015/021128 A1 | 2/2015 | | |
| WO | WO 2015/156417 A1 | 10/2015 | | |

OTHER PUBLICATIONS

Foley et al. "Pentyl-4-yn-VPA, a histone deacetylase inhibitor, ameliorates deficits in social behavior and cognition in a rodent model of autism spectrum disorders," European Journal of Pharmacology 727 (2014) 80-86. (Year: 2014).*
Weiwer et al. "Therapeutic potential of isoform selective HDAC inhibitors for the treatment of schizophrenia," Future Med. Chem. (2013) 5(13), 1491-1508. (Year: 2013).*
Prontera et al. "Brief Report: Functional MRI of a Patient with 7q11.23 Duplication Syndrome and Autism Spectrum Disorder," J Autism Dev Disord (2014) 44:2608-2613. (Year: 2014).*
Mulle et al. "Reciprocal Duplication of the Williams-Beuren Syndrome Deletion on Chromosome 7q11.23 Is Associated with Schizophrenia," Biol Psychiatry 2014;75:371-377. (Year: 2014).*
Brennand, Kristen J., et al., Modelling schizophrenia using human induced pluripotent stem cells; Nature, vol. 473, No. 7346, pp. 221-225; Supplementary Information pp. 1-44; May 12, 2011.
Hyman, Steven E., Target practice: HDAC inhibitors for schizophrenia; Nature Neuroscience, vol. 15, No. 9, pp. 1180-1181; Sep. 2012.
Kurita, Mitsumasa, et al., HDAC2 as a new target to improve schizophrenia treatment; Expert Review of Neurotherapeutics, vol. 13, No. 1, pp. 1-3; Jan. 2013.
Kurita, Mitsumasa, et al., HDAC2 regulates atypical antipsychotic responses through the modulation of mGlu2 promoter activity; Nature Neuroscience, vol. 15, No. 9, pp. 1245-1254; Sep. 2012.
Marchetto, Maria C.N., et al., A Model for Neural Development and Treatment of Rett Syndrome Using Human Induced Pluripotent Stem Cells; Cell, vol. 143, No. 4, pp. 527-539; Nov. 12, 2010.
Pasca, Sergiu P., et al., Using iPSC-derived neurons to uncover cellular phenotypes associated with Timothy syndrome; Nature Medicine, vol. 17, No. 12, pp. 1657-1662; Dec. 2011.
Prilutsky, Daria, et al., iPSC-derived neurons as a higher-throughput readout for autism: promises and pitfalls; Trends in Molecular Medicine, vol. 20, No. 2, pp. 91-104; Feb. 2014.
Sanders, Stephan J., et al., Multiple Recurrent De Novo CNVs, Including Duplications of the 7q11.23 Williams Syndrome Region, Are Strongly Associated with Autism; Neuron, vol. 70, No. 5, pp. 863-885; Jun. 9, 2011.
International Search Report and Written Opinion in PCT/EP2015/077659 dated Jun. 2, 2016.
Betancur, Catalina (2011) Etiological heterogeneity in autism spectrum disorders: more than 100 genetic and genomic disorders and still counting. Brain Research, Elsevier, 2011, 1380:42-77.
Bourgeron, Thomas (2015) From the genetic architecture to synaptic plasticity in autism spectrum disorder. Nature Reviews | Neuroscience Sep. 2015, 16:551-563.
Coleman et al. (2019) Rating of the effectiveness of 26 psychiatric and seizure medications for autism spectrum disorder: results of a national survey. Journal of Child and Adolescent Psychopharmacology. 2019, 29(2):107-123.
Wetmore et al. (2010) Emerging pharmacotherapies for neurodevelopmental disorders. J Dev Behav Pediatr. Sep. 2010, 31(7):564-581.
Autism Spectrum https://en.wikipedia.org/w/index.php?title=Austism_spectrum&oldid=975446789 Wikipedia Aug. 28, 2020.
Morris et al. (2015) 7q11.23 Duplication Syndrom: physical characteristics and natural history. Am J Med Genet A. Dec. 2015; 167A(12):2916-2935.

* cited by examiner

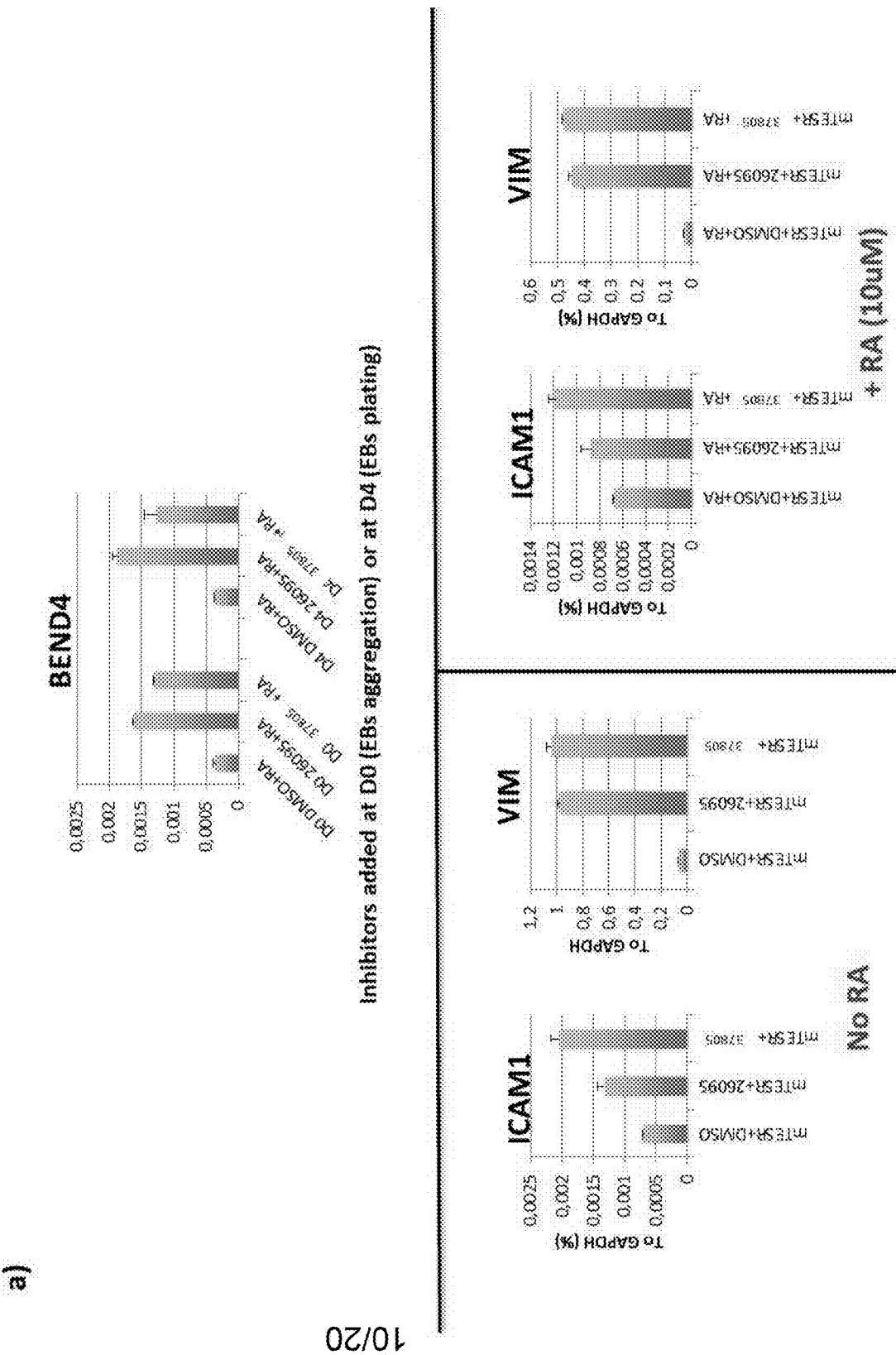
Fig. 10 (1/2)

b)
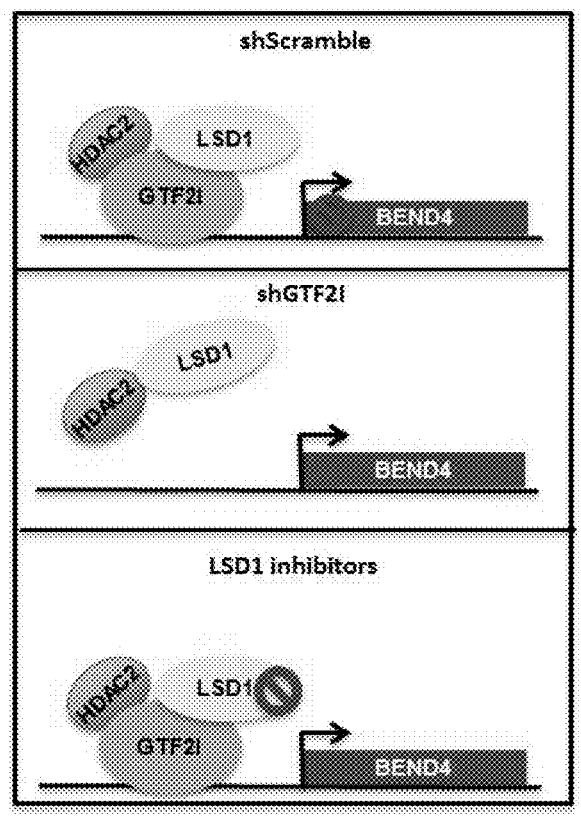
Fig. 10 (2/2)

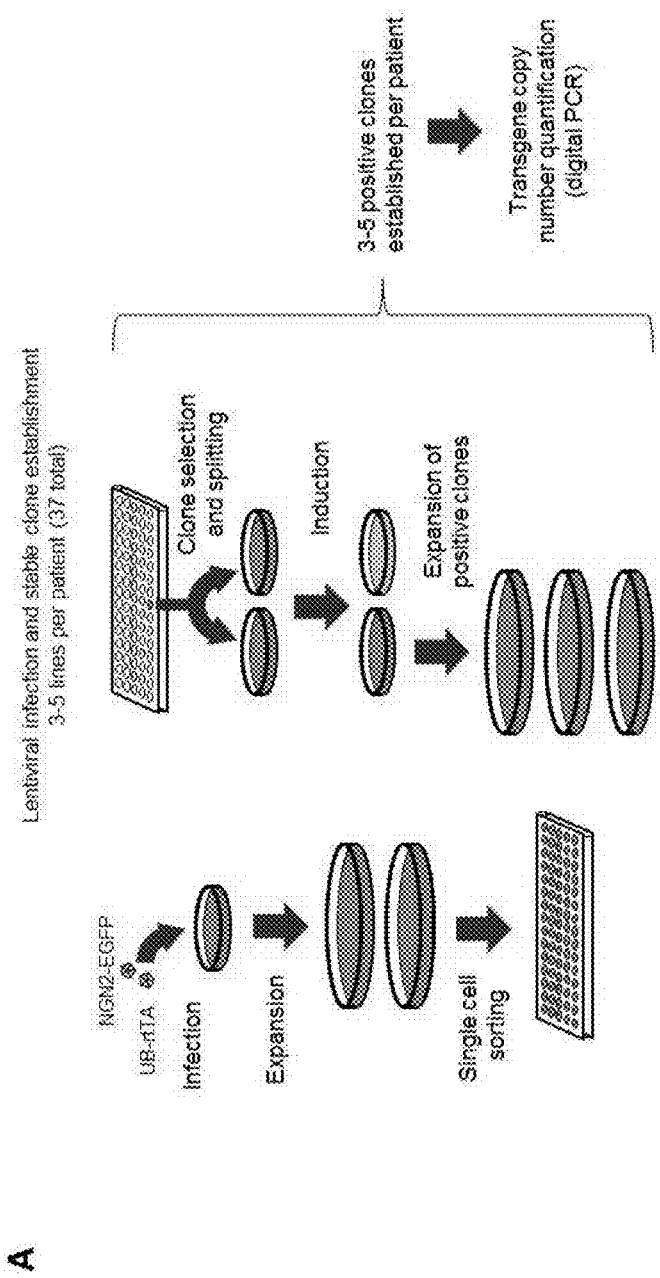
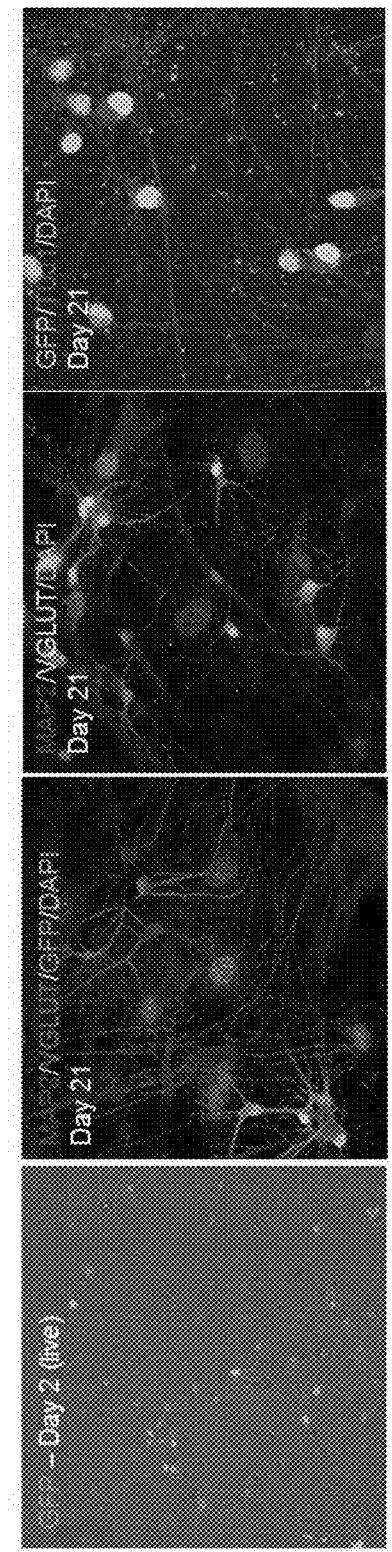
Fig. 11

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
gcaccgtcaa ggctgagaac                                                   20

<210> SEQ ID NO 2
<211> LENGTH: 19
<212> TYPE: DNA
<213> ORGANISM: Artificial Sequence
<220> FEATURE:
<223> OTHER INFORMATION: synthetic primer

<400> SEQUENCE: 2
agggatctcg ctcctggaa                                                    19

<210> SEQ ID NO 3
<211> LENGTH: 21
<212> TYPE: DNA
<213> ORGANISM: Artificial Sequence
<220> FEATURE:
<223> OTHER INFORMATION: synthetic primer

<400> SEQUENCE: 3
ggaaaaggaa aaggtcagtg c                                                 21

<210> SEQ ID NO 4
<211> LENGTH: 21
<212> TYPE: DNA
<213> ORGANISM: Artificial Sequence
<220> FEATURE:
```

```
<223> OTHER INFORMATION: synthetic primer

<400> SEQUENCE: 4
gtttatctgc tcttccgagg g                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
gatcttgcaa ccctgaaatg g                                              21

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
cacctggaga tagtattgac ctg                                            23

<210> SEQ ID NO 7
<211> LENGTH: 21
<212> TYPE: DNA
<213> ORGANISM: Artificial Sequence
<220> FEATURE:
<223> OTHER INFORMATION: synthetic primer

<400> SEQUENCE: 7
gctgccatct tcctctggta a                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic primer

<400> SEQUENCE: 8
gctgccatct tcctctggta a                                              21

<210> SEQ ID NO 9
<211> LENGTH: 22
<212> TYPE: DNA
<213> ORGANISM: Artificial Sequence
<220> FEATURE:
<223> OTHER INFORMATION: synthetic primer

<400> SEQUENCE: 9
cctcctgcat agcttcaaca aa                                             22

<210> SEQ ID NO 10
<211> LENGTH: 19
<212> TYPE: DNA
<213> ORGANISM: Artificial Sequence
<220> FEATURE:
<223> OTHER INFORMATION: synthetic primer

<400> SEQUENCE: 10
ggtcagaggg caacacaga                                                 19
```

```
<210> SEQ ID NO 11
<211> LENGTH: 19
<212> TYPE: DNA
<213> ORGANISM: Artificial Sequence
<220> FEATURE:
<223> OTHER INFORMATION: synthetic primer

<400> SEQUENCE: 11
caccagccct tgacatcag                                                19

<210> SEQ ID NO 12
<211> LENGTH: 22
<212> TYPE: DNA
<213> ORGANISM: Artificial Sequence
<220> FEATURE:
<223> OTHER INFORMATION: synthetic primer

<400> SEQUENCE: 12
tccctccaac tctacccttt ag                                            22

<210> SEQ ID NO 13
<211> LENGTH: 21
<212> TYPE: DNA
<213> ORGANISM: Artificial Sequence
<220> FEATURE:
<223> OTHER INFORMATION: synthetic primer

<400> SEQUENCE: 13
tgatgtggag agtttgagtg g                                             21

<210> SEQ ID NO 14
<211> LENGTH: 21
<212> TYPE: DNA
<213> ORGANISM: Artificial Sequence
<220> FEATURE:
<223> OTHER INFORMATION: synthetic primer

<400> SEQUENCE: 14
gaaaagatga ggaagggacg g                                             21

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
atgttaaggg agcagtgagc                                               20

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
atggtcagct ctcaagaatg g                                             21

<210> SEQ ID NO 17
<211> LENGTH: 21
<212> TYPE: DNA
<213> ORGANISM: Artificial Sequence
<220> FEATURE:
<223> OTHER INFORMATION: synthetic primer
```

```
<400> SEQUENCE: 17
gaacccagat ctcttacgct g                                              21

<210> SEQ ID NO 18
<211> LENGTH: 22
<212> TYPE: DNA
<213> ORGANISM: Artificial Sequence
<220> FEATURE:
<223> OTHER INFORMATION: synthetic primer

<400> SEQUENCE: 18
catctttaat ccccctgcctc tc                                            22

<210> SEQ ID NO 19
<211> LENGTH: 21
<212> TYPE: DNA
<213> ORGANISM: Artificial Sequence
<220> FEATURE:
<223> OTHER INFORMATION: synthetic primer

<400> SEQUENCE: 19
ggaaaccaga ttagagacgg g                                              21

<210> SEQ ID NO 20
<211> LENGTH: 22
<212> TYPE: DNA
<213> ORGANISM: Artificial Sequence
<220> FEATURE:
<223> OTHER INFORMATION: synthetic primer

<400> SEQUENCE: 20
gtttgtagtt acctctccag cg                                             22

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
gaaatcaagc ctcccaaagt g                                              21

<210> SEQ ID NO 22
<211> LENGTH: 19
<212> TYPE: DNA
<213> ORGANISM: Artificial Sequence
<220> FEATURE:
<223> OTHER INFORMATION: synthetic primer

<400> SEQUENCE: 22
tggagaggca gaaggaaaa                                                 19

<210> SEQ ID NO 23
<211> LENGTH: 21
<212> TYPE: DNA
<213> ORGANISM: Artificial Sequence
<220> FEATURE:
<223> OTHER INFORMATION: synthetic primer

<400> SEQUENCE: 23
aagccttctc cggtcataat g                                              21

<210> SEQ ID NO 24
<211> LENGTH: 20
```

```
<212> TYPE: DNA
<213> ORGANISM: Artificial Sequence
<220> FEATURE:
<223> OTHER INFORMATION: synthetic primer

<400> SEQUENCE: 24
tgatgtccgt gtttctcagg                                          20

<210> SEQ ID NO 25
<211> LENGTH: 20
<212> TYPE: DNA
<213> ORGANISM: Artificial Sequence
<220> FEATURE:
<223> OTHER INFORMATION: synthetic primer

<400> SEQUENCE: 25
cctgtgaact gaggttcctg                                          20

<210> SEQ ID NO 26
<211> LENGTH: 21
<212> TYPE: DNA
<213> ORGANISM: Artificial Sequence
<220> FEATURE:
<223> OTHER INFORMATION: synthetic primer

<400> SEQUENCE: 26
ccactgaaga ctcctgctaa g                                        21

<210> SEQ ID NO 27
<211> LENGTH: 19
<212> TYPE: DNA
<213> ORGANISM: Artificial Sequence
<220> FEATURE:
<223> OTHER INFORMATION: synthetic primer

<400> SEQUENCE: 27
acaagcccga agtccaaag                                           19

<210> SEQ ID NO 28
<211> LENGTH: 18
<212> TYPE: DNA
<213> ORGANISM: Artificial Sequence
<220> FEATURE:
<223> OTHER INFORMATION: synthetic primer

<400> SEQUENCE: 28
tcctgttcct gcacaacg                                            18

<210> SEQ ID NO 29
<211> LENGTH: 20
<212> TYPE: DNA
<213> ORGANISM: Artificial Sequence
<220> FEATURE:
<223> OTHER INFORMATION: synthetic primer

<400> SEQUENCE: 29
cctcaaccag aaacaagcag                                          20

<210> SEQ ID NO 30
<211> LENGTH: 21
<212> TYPE: DNA
<213> ORGANISM: Artificial Sequence
<220> FEATURE:
<223> OTHER INFORMATION: synthetic primer

<400> SEQUENCE: 30
```

```
ccaccgaccc tttagcttta g                                            21

<210> SEQ ID NO 31
<211> LENGTH: 21
<212> TYPE: DNA
<213> ORGANISM: Artificial Sequence
<220> FEATURE:
<223> OTHER INFORMATION: synthetic primer

<400> SEQUENCE: 31
gctcctgtaa ttagtgtcgg g                                            21

<210> SEQ ID NO 32
<211> LENGTH: 21
<212> TYPE: DNA
<213> ORGANISM: Artificial Sequence
<220> FEATURE:
<223> OTHER INFORMATION: synthetic primer

<400> SEQUENCE: 32
gggatcactt ttcagggtca g                                            21
```

REPROGRAMMING-BASED MODELS OF NEURODEVELOPMENTAL DISORDERS AND USES THEREOF

TECHNICAL FIELD

The present invention relates to iPSC produced from fibroblast obtained from a subject affected by a neurodevelopmental disorder entailing intellectual disability (ID) and/or a disorder belonging to the Autism Spectrum Disorder (ASD) and/or Schizophrenia (SZ) and uses thereof. The present invention also relates to a cortical neural progenitor cell or a terminally differentiated cortical glutamatergic or gabaergic neuronal cell or a neural crest stem cell line, a mesenchymal stem cell line produced from the iPSC or iPSC line. The invention also relates to method for identifying a compound for the treatment and/or prevention of a neurodevelopmental disorder entailing intellectual disability (ID) and/or a disorder belonging to the Autism Spectrum Disorder (ASD) and/or Schizophrenia (SZ) and to a LSD1 inhibitor or a HDAC2 inhibitor for use in the treatment of such disorders.

BACKGROUND

The potential of induced pluripotent stem cells (iPSC) for the functional annotation of human genomes and the modeling of diseases relies on the alignment of well defined genetic lesions to clinical data through molecular phenotypes in vitro. For this the critical challenge is two fold: i) define the extent to which early developmental lineages are informative about disease-relevant pathways affected by genetic mutations and, ii) assess the feasibility of reliably identifying those pathways beyond the sources of variability inherent to the iPSC-based approach[1].

In "iPSC-derived neurons as a higher-throughput readout for autism: promises and pitfalls"[2] Prilutsky et al. present an overview of efforts to study iPSC-derived neurons as a model for autism, and explore the plausibility of gene expression profiling as a reproducible and stable disease marker. The elucidation of disease etiologies and establishment of robust, scalable, high-throughput screening assays for autism spectrum disorders (ASDs) have been impeded by both inaccessibility of disease-relevant neuronal tissue and the genetic heterogeneity of the disorder. Neuronal cells derived from induced pluripotent stem cells (iPSCs) from autism patients may circumvent these obstacles and serve as relevant cell models. To date, derived cells are characterized and screened by assessing their neuronal phenotypes. These characterizations are often etiology-specific or lack reproducibility and stability.

Figure 6:
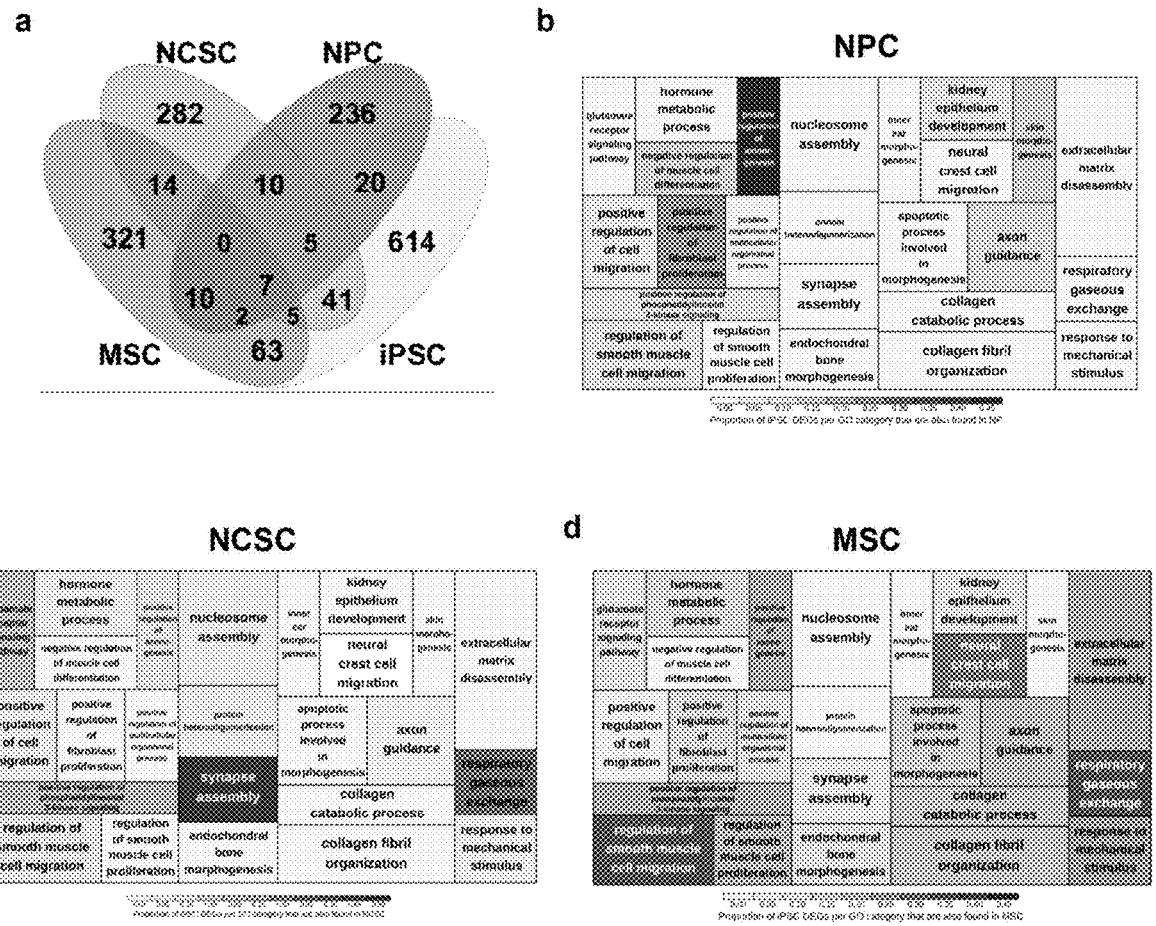

Ghosh et al.[3] highlight that the rising rates of autism spectrum disorder (ASD) and the lack of effective medications to treat its core symptoms have led to an increased sense of urgency to identify therapies for this group of neurodevelopmental conditions. Developing drugs for ASD, however, has been challenging because of a limited understanding of its pathophysiology, difficulties in modelling the disease in vitro and in vivo, the heterogeneity of symptoms, and the dearth of prior experience in clinical development. In the past few years these challenges have been mitigated by considerable advances in the understanding of forms of ASD caused by single-gene alterations, such as fragile X syndrome and tuberous sclerosis. In these cases they have gained insights into the pathophysiological mechanisms underlying these conditions. In addition, they have aided in the development of animal models and compounds with the potential for disease modification in clinical development. Moreover, genetic studies are illuminating the molecular pathophysiology of ASD, and new tools such as induced pluripotent stem cells offer novel possibilities for drug screening and disease diagnostics. Finally, large-scale collaborations between academia and industry are starting to address some of the key barriers to developing drugs for ASD. In FIG. 6 of the review, use of iPSCs for ASD drug discovery is presented: patient-derived fibroblasts can be reprogrammed to generate induced pluripotent stem cells (iPSCs) that can be differentiated into neurons to assess cellular phenotypes associated with autism spectrum disorder (ASD). These phenotypes can provide a basis for screening for compounds that reverse ASD-associated phenotypes, which could be tested in animal models and should lead to the identification of drug candidates for clinical development.

A particularly exciting advance in the field has been the demonstration that iPSCs derived from patients with neurodevelopmental disorders exhibit phenotypes distinct from those of cells from healthy volunteers. For example, Muotri and colleagues reported that iPSC-derived neurons from patients with Rett syndrome have a defect in synapse density and network activity[4]. Similarly, it has been reported that iPSC-derived neurons from patients with Timothy syndrome display electrophysiological defects[5]. These studies suggest that patient-derived iPSCs provide an avenue for identifying phenotypes that can be used for drug discovery[6,7].

WO2011079307 relates to Rett Syndrome as progressive neurological disorder caused by mutations in X-linked gene encoding MeCP2. X-chromosome inactivated female human neural cell derived from an induced pluripotent stem cell are used. A method of identifying a compound useful in treating the neurological disorder is described.

WO2013163455 relates to a method for screening candidate drugs that inhibit a neurological disease associated with a MeCP2 mutation, haploid insufficiency or a X-linked gene mutation or aberrant activity comprising inducing iPSC from a male subject to undergo neuronal differentiation and analyzing treated cells for an increase in neuronal networks, dendritic spine density, synapses, soma size, neuronal excitation, or calcium signaling.

US2007218068 relates to the identification of a human autism susceptibility gene, which can be used for the diagnosis, prevention and treatment of autism and related disorders, as well as for the screening of therapeutically active drugs. The document describes that the PITX1 gene on chromosome 5 and certain alleles thereof are related to susceptibility to autism and represent novel targets for therapeutic intervention.

SUMMARY OF THE INVENTION

Cell reprogramming promises to transform the study of the functional impact of human genetic variation on health and disease, enabling the bridging of genotypes to phenotypes in developmentally relevant human settings. Here the inventors apply this experimental paradigm to two disorders caused by symmetrical copy number variations (CNV) of 7q11.23 and displaying a striking combination of shared as well as symmetrically opposite phenotypes: Williams Beuren syndrome and 7q microduplication syndrome associated to autism spectrum disorder. Through a uniquely large and informative cohort of transgene-free patient-derived induced pluripotent stem cells (iPSC), along with their differentiated derivatives, the inventors find that 7q11.23 CNVs disrupt transcriptional circuits in disease-relevant pathways already at the pluripotent state. These alterations are then selectively amplified upon differentiation into disease-relevant lineages, thereby establishing the value of large iPSC cohorts in the elucidation of disease-relevant developmental pathways. In addition, the inventors functionally define the quota of transcriptional dysregulation specifically caused by dosage imbalances in GTF2I, a transcription factor in 7q11.23 thought to play a critical role in the two conditions, which the inventors found associated to key repressive chromatin modifiers.

Here the inventors focus on a paradigmatic pair of genetic syndromes caused by symmetrical copy number variations (CNV) at 7q11.23: Williams-Beuren syndrome (WBS; OMIM 194050) and Williams-Beuren region duplication syndrome (also known as Somerville-van der Aa syndrome, OMIM 609757) that includes autistic spectrum disorder (7dupASD)[8]. WBS and 7dupASD involve, respectively, the loss or gain of 26-28 genes and have a prevalence of between 1 in 7,500 and 1 in 10,000[9,10]. WBS is characterized by cardiovascular symptoms and facial dysmorphism, along with the hallmark behavioral-cognitive profile that combines hypersociability with comparatively well-preserved language abilities, but severely compromised visuospatial processing, counting and planning[9,11]. 7dupASD, in contrast, features varying degrees of ASD ranging from severe speech impairment to full blown autism, along with craniofacial dysmorphisms, among which some are similar and some symmetrically opposite to those of WBS patients[10,12]. Finally, both syndromes are associated with anxiety and attention deficit hyperactivity disorder (ADHD). Thus, the two conditions are paradigmatic of a fundamental aspect of CNV-based disease pairs, namely the fact that symmetrically opposite CNV result in shared as well as symmetrical phenotypes. Yet, despite significant insight from mouse models[13-16], the molecular pathways specifically affected by 7q11.23 CNV in the human lineages that are most relevant for disease phenotypes are yet to be uncovered.

Here the inventors present the largest cohort of WBS and 7dupASD iPSC lines and differentiated lineages, in which the inventors find that 7q11.23 dosage impacts disease-relevant transcriptional programs already in the pluripotent state. These alterations are partitioned into shared and symmetrically opposite ones and are further exacerbated upon differentiation into disease-relevant lineages. Finally, the inventors dissect the specific contribution of transcriptional factor GTF2I (also known as TFII-I), a key 7q11.23 gene, to the molecular phenotype of the two conditions in early developmental lineages.

The present invention provides an induced pluripotent stem cell (iPSC) or an iPSC line produced from a fibroblast obtained from a subject wherein said iPSC or an iPSC line expresses detectable levels of at least one of the following markers: OCT4, SOX2, NANOG, KLF4 and wherein the subject is affected by a neurodevelopmental disorder entailing intellectual disability (ID) and/or a disorder belonging to the Autism Spectrum Disorder (ASD) and/or Schizophrenia (SZ).

Preferably the subject is affected by either one of the two disorders caused by symmetrical copy number variations (CNV) at 7q11.23, namely Williams Beuren syndrome (WBS, OMIM 194050) and 7q11.23 microduplication syndrome (also known as Somerville-van der Aa syndrome, OMIM 609757) that includes autistic spectrum disorder (hereafter 7dupASD).

In the present invention iPSC or iPSC lines are generated using modified mRNA which enables non-integrating reprogramming of cells.

Preferably the cells of the invention are mammal cells, preferably human cells.

Preferably said iPSC or iPSC line harbors at least one genetic change as described in Table 4. Such change may be introduced during the reprogramming process and renders these cells genetically distinct from any other somatic cell naturally existing in the subject from which they derive. The iPSC or iPSC line may be engineered and genetically modified. Any method known in the art used to engineer cells may be used.

Preferably said iPSC or iPSC line expresses a reporter gene under the control of a dorsal telencephalon stem cell gene promoter.

Preferably the dorsal telencephalon stem cell gene promoter is selected from the group consisting of the promoters of: FOXG1, PAX6, EGR1, FOS and TBR2.

Preferably said iPSC or iPSC line stably expresses NGN2.

Preferably said stable expression of NGN2 is inducible.

The stable expression of NGN2 may be achieved by any means known in the art such as genetic modification, transfection, exogenous exposure etc.

The present invention provides the iPSC or iPSC line as defined above for use in a method to purify and/or isolate a cortical neural progenitor cell or a neuronal cell.

Preferably the method to purify and/or isolate a cortical neural progenitor cell or a neuronal cell, comprises: i) inducing neurulation of a subject iPSC and generate neural rosettes following established protocols; ii) purifying cortical progenitor cells expressing at least one of the markers: FOXG1, PAX6, EGR1, FOS, TBR2 by either drug selection or fluorescence activated cell sorting (FACS) enabled by the respective reporter constructs; iii) further differentiating said purified neural progenitors into postmitotic, terminally differentiated neuron.

The present invention provides a population comprising two or more iPSC or iPSC line of the invention.

The present invention provides cortical neural progenitor cell produced from the iPSC or iPSC line of the invention, wherein said cortical neural progenitor cell expresses detectable levels of at least one of the following markers: FOXG1, PAX6, EGR1, FOS and TBR2, ZO1, SOX2.

The present invention provides a terminally differentiated cortical glutamatergic neuronal cell produced from the iPSC or iPSC line according to the invention, directly or through the intermediate of the cortical neural progenitor cell of the invention, wherein said terminally differentiated cortical glutamatergic neuronal cell expresses detectable levels of at least one of the following markers: PSD95, Synapsin, Vglut, Ctip2, BRN2, TBR1, TBR2, Cux 1, Reelin, Satb2, MAP2, TUJ1 ClassIII, Glu-R1, ER81, vGlut1, Homer1, Homer 2, Synaptophysin, Foxp1, GRIN1, GRIN2D, GRIN2A, GRM1, GRM8, slc1a6, slc17a7, TrkB.

The present invention provides a terminally differentiated cortical gabaergic neuronal cell produced from the iPSC or iPSC line according to the invention, directly or through the intermediate of the cortical neural progenitor cell of the invention, wherein said terminally differentiated cortical gabaergic neuronal cell expresses detectable levels of at least one of the following markers: Nkx2.1, GABA, VGAT, ASCL1, DLX2, DLX5, CALBINDIN, CALRETININ, SOMATOSTATIN, PARVALBUMIN, GAD67, SLC32A1, PSD95, Synapsin, Vglut, Ctip2, BRN2, TBR1, TBR2, Cux 1, Satb2, MAP2, TUJ1 ClassIII, Glu-R1, vGlut1, Homer1, Synaptophysin.

The present invention provides a population comprising two or more cortical neural progenitor cells according to the invention.

The present invention provides a population comprising two or more terminally differentiated cortical glutamatergic or gabaergic neuronal cells according to the invention.

The present invention provides neural crest stem cell line produced from the iPSC or iPSC line according to any one of claim 1 to 7, wherein said neural crest stem cell expresses detectable levels of at least one of the following markers: HNK1, NGFR, SOX9, SOX10, PAX3, ZINC1 and TFAP2.

The present invention provides a population comprising two or more neural crest stem cells as defined above.

The present invention provides a mesenchymal stem cell line produced from the iPSC or iPSC line as defined above, wherein said mesenchymal stem cell expresses detectable levels of at least one of the following markers: CD44 and CD73.

The present invention provides a population comprising two or more mesenchymal stem cells as defined above.

The present invention provides a method to obtain iPSC or iPSC line as defined above and stably expressing NGN2 comprising the steps of:

Infecting an iPSC population with at least one lentiviral vector driving the expression of NGN2;
expanding the infected iPSC population;
sorting iPSCs as DAPI-negative single cells thereby obtaining iPSC clones;
expanding said iPSC clones and
optionally characterizing integration copy numbers.

Preferably the method comprises the steps of:
infecting iPSCs with lentiviral vectors that drive the expression of NGN2 directly upon splitting of iPSCs, preferably the expression is inducible;
expanding the infected but uninduced iPSC population up to between 3 and 9 million cells;
sorting iPSCs as DAPI-negative single cells, preferably in 96 well plates;
expanding iPSC clones derived from single cells until reaching between 0.5 and 1 million cells;
inducing half of each iPSC clone derived in the step above to check for GFP expression while retaining an uninduced population of the same clone for its expansion;
further expanding GFP-positive and uninduced clones until reaching between 3 and 9 million cells;
characterizing integration copy numbers, preferably by digital PCR or TaqMan assays The present invention provides a method for identifying a compound for the treatment and/or prevention of a neurodevelopmental disorder entailing intellectual disability (ID) and/or a disorder belonging to the Autism Spectrum Disorder (ASD) and/or Schizophrenia (SZ) comprising:

a) inducing the iPSC or iPSC line as defined above or the cortical neural progenitor cell as defined above to undergo differentiation thereby obtaining a neural derivative;
b) exposing said neural derivative to a candidate compound;
c) measuring the level of expression of at least one gene selected from the group of: genes comprised in the 7q11.23 interval, genes found dysregulated in NPC by 7q11.23 dosage imbalances in particular genes of the WBS interval: GTF2IP1, NCF1B, GTF2IRD2P, POM121, NSUN5, TRIM50, FKBP6, FZD9, BAZ1B, BCL7B, TBL2, MLXIPL, VPS37D, DNAJC30, WBSCR22, STX1A, WBSCR26, ABHD11, CLDN3, CLDN4, WBSCR27, WBSCR28, ELN, LIMK1, EIF4H, LAT2, RFC2, CLIP2, GTF2IRD1, GTF2I, NCF1, GTF2IRD2, STAG3L2, PMS2P5, WBSCR16 and differentially-expressed genes in Neural Progenitors:
ABCA1, ABCD1, ACAP3, ADAMTS16, ADHFE1, AFAP1, AGPAT6, AKAP12, ALK, ANKRD52, ANO8, AP2A2, APBA1, APC2, ARC, ARFRP1, ARHGAP6, ARHGEF2, ARSA, ARVCF, ASB1, ASXL3, BAHD1, BAIAP3, BCAR1, BLCAP, BRPF1, BRSK1, C10orf11, C3orf67, CABLES1, CBFA2T3, CCDC88C, CCNE1, CDC25B, CDH5, CDH6, CDK5R1, CDK5R2, CELF3, CELSR3, CENPB, CES3, CHGA, CHUK, CLDN19, CLSTN2, CNTN5, CORO2B, CPEB2, CRIPAK, CTC1, CTSK, CYB561A3, CYTH2, DAGLA, DARC, DBC1, DCHS1, DCTN1, DEFB108B, DISP2, DLK1, DLL3, DNAJC14, DPP9, DRP2, DUSP10, DUSP26, DUSP4, DUSP8, EBF1, EFNA5, EGFL8, ELAVL3, EPHB1, ETS2, FAM166B, FAM173B, FAM174B, FAM20C, FAM222A, FAT3, FKBP11, FKRP, FSTL3, FXR2, GAL3ST4, GALNS, GALR3, GDPD5, GNB3, GNG2, GPR123, GPR162, GPR173, GRIK5, HCN4, HCRT, HEPACAM2, HEXDC, HID1, HIST1H4J, HLA-DPB1, HRH3, HUNK, IFRD1, IL13RA2, INSM1, IRF2BPL, IZUMO4, KALRN, KAZN, KCNA2, KCNK6, KCTD12, KIAA0226, KIF26B, KLHL18, KLK6, KRBA2, LCE1E, LENG8, LPCAT1, LRCH4, LRP2, LRRN3, LZTS1, MANEAL, MAP1A, MAP1LC3C, MAP3K12, MAP3K13, MEGF8, MEIS1, MEIS2, MERTK, MICAL1, MIDN, MIR27B, MIR3194, MIR421, MIR54812, MIR590, MIR765, MLH3, MUC1, MUM1, MXRA5, MXRA7, MYADM, MYH9, NELL1, NFASC, NGFR, NRP1, NRSN1, OSBPL7, PANK2, PCBP3, PCDH10, PCDH9, PCDHGA11, PCDHGB1, PCDHGB7, PDF, PDGFRA, PGBD2, PICK1, PKDCC, PLD6, PLEKHA6, PLXNB1, PNMA1, PON2, POU2F2, PPIP5K1, PPP1R1C, PPP1R3F, PRAMEF13, PRDM11, PRICKLE4, PRKCG, PRKRIP1, PRRT2, PTCHD2, PTPLAD2, PTPN21, PTPRG, PTX3, RAB11FIP3, RAMP2, RBM5, RGAG4, RGS6, RGS8, RGS9, RIN2, RNF121, RNF44, RPS6KA2, RUNDC3A, RUSC2, S100A2, SCG2, SCN3A, SEC16A, SEMA5A, SEMA6D, SGSM2, SLC10A4, SLC2A10, SLC35E2, SLC35F6, SLC35G1, SLC4A3, SLC5A12, SLC6A1, SLC7A1, SLCO1A2, SMPD3, SNED1, SNORA35, SPHK2, SPOCK2, SPRY2, SPTBN2, SRGAP1, SRRM4, SYN1, SYNGAP1, SYNM, SYTL1, TAF13, TECPR2, TENC1, TEX261, THBS3, TIAF1, TLN2, TMEM133, TMEM151B, TMEM201, TNIK, TOB1, TP5313, TPM1, TRIM41, TRIM46, TRPC4, TRPM5, TSPAN9, TSPYL5, TTC21A, TTLL3, TTPAL, UBE2QL1, UBTF, ULK1, UNC13A, VAX1, VIPAS39, XKR4, ZC3H4, ZDHHC22, ZFHX2, ZFHX3, ZNF124, ZNF132, ZNF135, ZNF195, ZNF275, ZNF300, ZNF335, ZNF48, ZNF592, ZNF646, ZNF667, ZNF713, ZNF772.

d) comparing the expression levels measured in c) to control levels wherein if the level of expression of said gene is restored to the control level, said compound is identified.

The present screening platform/method is primarily designed to screen for gene dosage rescue at the mRNA level, measured for instance by qRT-PCR.

The present invention's screening is primarily designed at finding compounds that rescue the dosage of critical genes involved in a neurodevelopmental disorder entailing intellectual disability (ID) and/or a disorder belonging to the Autism Spectrum Disorder (ASD) and/or Schizophrenia (SZ).

Measurement of expression can be performed by multiplex quantitative Reverse Transcription (RT)-Polymerase Chain Reaction (PCR) or barcode-enabled high-throughput Ribonucleic Acid (RNA) sequencing;

Preferably said method involves HTS-format differentiation starting from previously generated cortical neural progenitors as described above.

Preferably the method further comprises analyzing iPSC-derived neurons for morphology (dendritic arborization, density and shape of dendritic spines), expression of markers of neuronal differentiation, synaptic maturation and function. The analysis of iPSC-derived neurons may be carried out either directly or through the intermediate of cortical neural progenitors and may including HTS-compatible quantitation of dendritic arborization, density and shape of dendritic spines, expression of markers of neuronal differentiation, synaptic maturation and function (including either post-fixation assessment of defining markers or live-imaging of neuronal activity-dependent calcium signaling).

Preferably the Autism Spectrum Disorder is WBS or 7dupASD.

Thanks to the finding of the present invention, it is also provided a LSD1 inhibitor or a HDAC2 inhibitor for use in the prevention and/or treatment of a neurodevelopmental disorder entailing intellectual disability (ID) and/or an Autism Spectrum Disorder (ASD) and/or Schizophrenia (SZ). Preferably the Autism Spectrum Disorder (ASD) is WBS or 7dupASD and the Schizophrenia (SZ) is a 7q11.23 microduplication-dependent Schizophrenia (SZ).

In the present invention an autistic pathology means a condition matching at least one criterion in the definition of the Autism Spectrum Disorder (ASD), including the conditions associated to one of the following genetic lesions. Similarly, Schizophrenia (SZ) means a condition matching at least one criterion in the definition of Schizophrenia (SZ) including the conditions associated to one of the following genetic lesions. ASD and SZ pathologies are comprised in the following:

OMIM Categories Related to ASD:

46,xy sex reversal 9; srxy9 (616067). abelson helper integration site 1; ahi1 (608894). acrodysostosis 2 with or without hormone resistance; acrdys2 (614613). activity-dependent neuroprotector homeobox; adnp (611386). adenosine deaminase; ada (608958). adenylosuccinase deficiency (103050). aldehyde dehydrogenase 1 family, member a3; aldh1a3 (600463). aldehyde dehydrogenase 5 family, member a1; aldh5a1 (610045). alg12, s. cerevisiae, homolog of; alg12 (607144). angelman syndrome; as angelman syndrome chromosome region, included; ancr, included (105830). aniridia; an cataract, congenital, with late-onset corneal dystrophy, included (106210). ankyrin 3; ank3 (600465). aristaless-related homeobox, x-linked; arx (300382). armadillo repeat gene deleted in vcfs; arvcf (602269). arthrogryposis multiplex congenita, neurogenic type; amecn (208100). arthrogryposis, mental retardation, and seizures; amrs (615553). asperger syndrome, susceptibility to, 1; aspg1 (608638). asperger syndrome, susceptibility to, 2; aspg2 (608631). asperger syndrome, susceptibility to, 3; aspg3 (608781). asperger syndrome, susceptibility to, 4; aspg4 (609954). asperger syndrome, x-linked, susceptibility to, 1; aspgx1 (300494). asperger syndrome, x-linked, susceptibility to, 2; aspgx2 (300497). athabaskan brainstem dysgenesis syndrome; abds bosley-salih-alorainy syndrome, included; bsas, included (601536). atpase, class v, type 10a; atp10a (605855). attention deficit-hyperactivity disorder, susceptibility to, 1 (608903). attention deficit-hyperactivity disorder, susceptibility to, 2 (608904). attention deficit-hyperactivity disorder; adhd (143465). australia antigen (209800). autism autism, susceptibility to, 1, included; auts1, included (209850). autism, susceptibility to, 10; auts10 (611016). autism, susceptibility to, 11; auts11 (610836). autism, susceptibility to, 12; auts12 (610838). autism, susceptibility to, 13; auts13 (610908). autism, susceptibility to, 15; auts15 (612100). autism, susceptibility to, 16; auts16 (613410). autism, susceptibility to, 17; auts17 (613436). autism, susceptibility to, 18; auts18 (615032). autism, susceptibility to, 19; auts19 (615091). autism, susceptibility to, 3; auts3 (608049). autism, susceptibility to, 5; auts5 (606053). autism, susceptibility to, 6; auts6 (609378). autism, susceptibility to, 7; auts7 (610676). autism, susceptibility to, 8; auts8 (607373). autism, susceptibility to, 9; auts9 (611015). autism, susceptibility to, x-linked 1; autsx1 (300425). autism, susceptibility to, x-linked 2; autsx2 mental retardation, x-linked, included (300495). autism, susceptibility to, x-linked 3; autsx3 (300496). autism, susceptibility to, x-linked 5; autsx5 (300847). bannayan-riley-ruvalcaba syndrome; brrs (153480). beckwith-wiedemann syndrome; bws beckwith-wiedemann syndrome chromosome region, included; bwcr, included (130650). brachydactyly-mental retardation syndrome; bdmr chromosome 2q37 deletion syndrome, included (600430). branched-chain alpha-keto acid dehydrogenase kinase; bckdk (614901). branched-chain ketoacid dehydrogenase kinase deficiency; bckdkd (614923). brunner syndrome (300615). cadherin 8; cdh8 (603008). calcium channel, voltage-dependent, 1 type, alpha-1c subunit; cacna1c (114205). calcium channel, voltage-dependent, 1 type, alpha-1d subunit; cacna1d (114206). calcium-dependent activator protein for secretion 2; cadps2 (609978). catechol-o-methyltransferase; comt catechol-o-methyltransferase activity, low, in red cells, included (116790). ceroid lipofuscinosis, neuronal, 8; cln8 (600143). charge syndrome (214800). chromodomain helicase dna-binding protein 2; chd2 (602119). chromodomain helicase dna-binding protein 8; chd8 (610528). chromosome 12 open reading frame 57; c12orf57 (615140). chromosome 15q11-q13 duplication syndrome autism, susceptibility to, 4, included; auts4, included (608636). chromosome 15q11.2 deletion syndrome (615656). chromosome 15q13.3 deletion syndrome (612001). chromosome 15q25 deletion syndrome (614294). chromosome 16p11.2 deletion syndrome, 220-kb body mass index quantitative trait locus 16, included; bmiq16, included (613444). chromosome 16p11.2 deletion syndrome, 593-kb autism, susceptibility to, 14a, included; auts14a, included (611913). chromosome 16p11.2 duplication syndrome autism, susceptibility to, 14b, included; auts14b, included (614671). chromosome 16p12.1 deletion syndrome, 520-kb fragile site 16p12, included (136570). chromosome 16p12.2-p11.2 deletion syndrome, 7.1- to 8.7-mb (613604). chromosome 16p13.3 deletion syndrome, proximal (610543). chromosome 16p13.3 duplication syndrome (613458). chromosome 17p13.3, centromeric, duplication syndrome (613215). chromosome 17q12 deletion syndrome (614527). chromosome 17q21.31 duplication syndrome (613533). chromosome 1q21.1 deletion syndrome, 1.35-mb (612474). chromosome 1q21.1 duplication syndrome (612475). chromosome 22q11.2 duplication syndrome (608363). chromosome 2p16.1-p15 deletion syndrome (612513). chromosome 2p16.3 deletion syndrome schizophrenia 17, included; sczd17, included (614332). chromosome 3 open reading frame 58; c3orf58 (612200). chromosome 3pter-p25 deletion syndrome (613792). chromosome 3q13.31 deletion syndrome (615433). chromosome 3q29 deletion syndrome (609425). chromosome 4q32.1-q32.2 triplication syndrome (613603). chromosome xp22 deletion syndrome (300830). cognitive function 1, social; cgf1 (300082). contactin 4; cntn4 (607280). contactin-associated protein-like 2; cntnap2 (604569). comelia de lange syndrome 1; cdls1 (122470). cortactin-binding protein 2; cttnbp2 (609772). cowden syndrome 1; cws1 dysplastic gangliocytoma of the cerebellum, included (158350). craniosynostosis 3; crs3 (615314). cyclic vomiting syndrome; cvs cyclic vomiting syndrome with neuromuscular disease, included (500007). cyclin-dependent kinase inhibitor 1b; cdkn1b (600778). cystinuria cystinuria, type a, included (220100). dcn1 domain-containing protein 1; dcun1d1 (605905). diamond-blackfan anemia 6; dba6 (612561). dihydropyrimidine dehydrogenase deficiency 5-@fluorouracil toxicity, included (274270). distal-less homeobox 1; dlx1 (600029). distal-less homeobox 2; dlx2 (126255). doublecortin; dcx (300121). dual-specificity tyrosine phosphorylation-regulated kinase 1a; dyrk1a (600855). early growth response 2; egr2 (129010). engrailed 2; en2 (131310). epilepsy, familial focal, with variable foci; ffevf (604364). epilepsy, focal, with speech disorder and with or without mental retardation; fesd landau-kleffner syndrome, included; lks, included (245570). epilepsy, x-linked, with variable learning disabilities and behavior disorders (300491). epileptic encephalopathy, childhood-onset; eeoc (615369). epileptic encephalopathy, early infantile, 1; eiee1 (308350). epileptic encephalopathy, early infantile, 13; eiee13 (614558). epileptic encephalopathy, early infantile, 6; eiee6 (607208). epileptic encephalopathy, early infantile, 9; eiee9 (300088). epsilon-trimethyllysine hydroxylase deficiency; tmlhed (300872). epsilon-trimethyllysine hydroxylase; tmlhe (300777). eukaryotic translation initiation factor 4e-binding protein 2; eif4ebp2 (602224). eukaryotic translation initiation factor 4e; eif4e (133440). fmr1 gene; fmr1 fragile site, folic acid type, rare, fraxq27.3, included; fraxa, included (309550). forkhead box p1; foxp1 (605515). forkhead box p2; foxp2 (605317). fragile x mental retardation syndrome primary ovarian insufficiency, fragile x-associated, included (300624). fragile x tremor/ataxia syndrome; fxtas (300623). gamma-aminobutyric acid receptor, alpha-4; gabra4 (137141). gamma-aminobutyric acid receptor, alpha-5; gabra5 (137142). gamma-aminobutyric acid receptor, beta-3; gabrb3 (137192). gamma-aminobutyric acid receptor, gamma-3; gabrg3 (600233). gastrin-releasing peptide receptor; grpr (305670). gephyrin; gphn mll/gphn fusion gene, included (603930). gilles de la tourette syndrome; gts chronic motor tics, included (137580). glutamate receptor, ionotropic, n-methyl-d-aspartate, subunit 2b; grin2b (138252). glutamate receptor, metabotropic, 5; grm5 (604102). glycine encephalopathy; gce hyperglycinemia, transient neonatal, included; tnh, included (605899). glyoxalase i; glo1 (138750). hect domain and rcc1-like domain 2; herc2 (605837). hepatocyte cell adhesion molecule; hepacam (611642). homeobox a1; hoxa1 (142955). homer, *drosophila*, homolog of, 1; homer1 homer1a, included (604798). hyper-ige recurrent infection syndrome, autosomal dominant (147060). hyperlexia (238350). integrin, beta-3; itgb3 thrombocytopenia, neonatal alloimmune, included; nait, included (173470). intelligence quantitative trait locus 2 (610294). interleukin 1 receptor accessory protein-like 1; il1rapl1 il1rapl1/dmd fusion gene, included (300206). katanin, p60 subunit, a-like protein 2; katnal2 (614697). kiaa0442 gene; kiaa0442 (607270). kiaa2022 gene; kiaa2022 (300524). low density lipoprotein receptor-related protein 2; lrp2 (600073). lubs x-linked mental retardation syndrome; mrxsl (300260). lysine-specific demethylase 5c; kdm5c (314690). macrocephaly/autism syndrome (605309). mage-like 2; magel2 (605283). map/microtubule affinity-regulating kinase 1; mark1 (606511). mediator complex subunit 12; med12 (300188). megalencephalic leukoencephalopathy with subcortical cysts 1; mlc1 (604004). megalencephalic leukoencephalopathy with subcortical cysts 2a; mlc2a (613925). megalencephalic leukoencephalopathy with subcortical cysts 2b, remitting, with or without mental retardation; mlc2b (613926). mental retardation with language impairment and with or without autistic features (613670). mental retardation, autosomal dominant 1; mrd1 chromosome 2q23.1 deletion syndrome, included (156200). mental retardation, autosomal dominant 20; mrd20 chromosome 5q14.3 deletion syndrome, included (613443). mental retardation, autosomal dominant 23; mrd23 (615761). Mental retardation, autosomal dominant 26; mrd26 (615834). mental retardation, autosomal dominant 5; mrd5 (612621). mental retardation, autosomal dominant 6; mrd6 (613970). mental retardation, autosomal dominant 7; mrd7 (614104). mental retardation, autosomal dominant, 28; mrd28 (615873). mental retardation, autosomal recessive 34; mrt34 (614499). mental retardation, autosomal recessive 38; mrt38 (615516). mental retardation, x-linked 21; mrx21 (300143). mental retardation, x-linked 72; mrx72 (300271). mental retardation, x-linked 98; mrx98 (300912). mental retardation, x-linked, syndromic, claes-jensen type; mrxscj (300534). met protooncogene; met (164860). methyl-cpg-binding domain protein 1; mbd1 methyl-cpg-binding protein 1 complex, included (156535). methyl-cpg-binding domain protein 5; mbd5 (611472). methyl-cpg-binding protein 2; mecp2 (300005). microphthalmia, isolated 3; mcop3 (611038). microphthalmia, isolated 8; mcop8 (615113). microphthalmia, syndromic 1; mcopsl (309800). microtubule-associated protein 2; map2 (157130). mlc1 gene; mlc1 (605908). modifier, x-linked, for neurofunctional defects (309840). momo syndrome (157980). monoamine oxidase a; maoa antisocial behavior following childhood maltreatment, susceptibility to, included (309850). mucopolysaccharidosis, type iiib; mps3b (252920). myhre syndrome; myhrs (139210). n-acetylglucosaminidase, alpha-; naglu (609701). nance-horan syndrome; nhs (302350). necdin-like gene 2; ndnl2 (608243). netrin g1; ntng1 (608818). neurexin i; nrxn1 (600565). neurexin ii; nrxn2 (600566). neurexin iii; nrxn3 (600567). neurobeachin; nbea fragile site fra13a, included (604889). neuroligin 1; nlgn1 (600568). neuroligin 3; nlgn3 (300336). neuroligin 4, y-linked; nlgn4y (400028). neuroligin 4; nlgn4 (300427). nevoid hypermelanosis, linear and whorled; lwnh hyperpigmentation, progressive cribriform and zosteriform, included; pczh, included (614323). nuclear receptor subfamily 1, group i, member 3; nr1i3 (603881). opioid receptor, mu-1; oprm1 (600018). ossified ear cartilages with mental deficiency, muscle wasting, and bony changes (259050). paired box gene 6; pax6 (607108). patched domain-containing protein 1; ptchd1 (300828). peroxisome biogenesis disorder 9b; pbd9b peroxisome biogenesis disorder, complementation group 11, included; cg11, included (614879). phelan-mcdermid syndrome (606232). phosphatase and tensin homolog; pten pten hamartoma tumor syndrome, included; phts, included (601728). potassium channel tetramerization domain-containing protein 3; kctd3 (613272). potassium channel, voltage-gated, subfamily h, member 5; kcnh5 (605716). potassium voltage-gated channel, shal-related subfamily, member 2; kcnd2 (605410). potocki-lupski syndrome; ptls (610883). prader-willi-like syndrome; pwls (615547). protein phosphatase 2, regulatory subunit b, gamma isoform; ppp2r2c (605997). protocadherin 10; pcdh10 (608286). rap guanine nucleotide exchange factor; rapgef4 (606058). ras-associated protein rab39b; rab39b (300774). retina and anterior neural fold homeobox gene; rax (601881). rett syndrome, congenital variant (613454). rett syndrome; rtt rett syndrome, zappella variant, included (312750). ribosomal protein l10; rpl10 (312173).

richieri-costa/guion-almeida syndrome (268850). ma-binding protein fox1, c. elegans, homolog of, 1; rbfox1 (605104). schizophrenia 13; sczd13 schizophrenia, neurophysiologic defect in, included (613025). schizophrenia 15; sczd15 (613950). schizophrenia 4; sczd4 (600850). schizophrenia; sczd (181500). semaphorin 5a; sema5a (609297). sh3 and multiple ankyrin repeat domains 1; shank1 (604999). sh3 and multiple ankyrin repeat domains 2; shank2 (603290). sh3 and multiple ankyrin repeat domains 3; shank3 (606230). siderius x-linked mental retardation syndrome; mrxssd (300263). slit-robo rho gtpase-activating protein 2c; srgap2c (614704). smith-lemli-opitz syndrome; slos (270400). sodium channel, neuronal type i, alpha subunit; scn1a (182389). sodium channel, voltage-gated, type ii, alpha subunit; scn2a (182390). sodium channel, voltage-gated, type viii, alpha subunit; scn8a (600702). solute carrier family 25 (mitochondrial carrier, aralar), member 12; slc25a12 (603667). solute carrier family 35 (udp-n-acetyl-glucosamine transporter), member 3; slc35a3 (605632). solute carrier family 6 (neurotransmitter transporter, serotonin), member 4; slc6a4 (182138). solute carrier family 9 (sodium/hydrogen exchanger), member 9; slc9a9 (608396). specific language impairment 3; sli3 (607134). specific language impairment 4; sli4 (612514). specific language impairment 5; sli5 (615432). spectrin repeat-containing nuclear envelope protein 1; syne1 cpg2 isoform, included; cpg2, included (608441). speech-language disorder 1; spch1 (602081). succinic semialdehyde dehydrogenase deficiency; ssadhd (271980). suppressor of tumorigenicity 7; st7 (600833). synapsin i; syn1 (313440). synaptic ras-gtpase-activating protein 1; syngap1 (603384). syndecan 2; sdc2 (142460). temtamy syndrome; temtys (218340). thioredoxin reductase 2; txnrd2 (606448). timothy syndrome; ts (601005). topoisomerase, dna, i; top1 top1/nup98 fusion gene, included (126420). topoisomerase, dna, ii, beta; top2b (126431). tsc1 gene; tsc1 (605284). tsc2 gene; tsc2 (191092). tuberous sclerosis 1; tsc1 (191100). tuberous sclerosis 2; tsc2 tsc2 angiomyolipomas, renal, modifier of, included (613254). tyrosine hydroxylase; th (191290). ubiquitin-protein ligase e3a; ube3a (601623). upf3, yeast, homolog of, b; upf3b (300298). van maldergem syndrome 1; vmlds1 (601390). velocardiofacial syndrome (192430). waardenburg syndrome, type 2e; ws2e (611584). wfs1 gene; wfs1 (606201). williamns-beuren region duplication syndrome wbs triplication syndrome, included (609757). williams-beuren syndrome; wbs (194050). wingless-type mmtv integration site family, member 2; wnt2 (147870). wolfram-like syndrome, autosomal dominant; wfsl (614296). xeroderma pigmentosum, complementation group c; xpc (278720). xpc gene; xpc (613208). zinc finger protein 407; znf407 (615894)

OMIM Categories Related to Schizophrenia:
schizophrenia; sczd (181500). schizophrenia 12 (608543). schizophrenia 16; sczd16 (613959). schizophrenia 15; sczd15 (613950). schizophrenia 13; sczd13 schizophrenia, neurophysiologic defect in, included (613025). schizophrenia 14 (612361). schizophrenia 10; sczd10 (605419). disrupted in schizophrenia 2; disc2 (606271). schizophrenia 11 (608078). schizophrenia 8; sczd8 (603206). schizophrenia 5; sczd5 (603175). schizophrenia 7; sczd7 (603176). schizophrenia 18; sczd18 schizoaffective disorder, included (615232). schizophrenia 1; sczd1 (181510). schizophrenia 6; sczd6 (603013). schizophrenia 2; sczd2 (603342). schizophrenia 3; sczd3 (600511). schizophrenia 4; sczd4 (600850). schizophrenia 9; sczd9 (604906). disrupted in schizophrenia 1; disc1 (605210). chromosome 2p16.3 deletion syndrome schizophrenia 17, included; sczd17, included (614332). proline dehydrogenase; prodh (606810). synapsin ii; syn2 (600755). dopamine receptor d3; drd3 (126451). catechol-o-methyltransferase; comt catechol-o-methyltransferase activity, low, in red cells, included (116790). 5-hydroxytryptamine receptor 2a; htr2a (182135). reticulon 4 receptor; rtn4r (605566). solute carrier family 1 (neuronal/epithelial high affinity glutamate transporter), member 1; slc1a1 (133550). d-amino acid oxidase activator; daoa (607408). neurexin i; nrxn1 (600565). sh3 and multiple ankyrin repeat domains 3; shank3 (606230). dystrobrevin-binding protein 1; dtnbp1 (607145). chromosome 1q21.1 duplication syndrome (612475). chitinase 3-like 1; chi3l1 (601525). apolipoprotein l-iv; apol4 (607254). chromosome 1q21.1 deletion syndrome, 1.35-mb (612474). d-amino acid oxidase; dao (124050). neuregulin 1; nrg1 glial growth factor 2, included; ggf2, included (142445). apolipoprotein l-ii; apol2 (607252). chromosome 17q12 deletion syndrome (614527). 5,10-methylenetetrahydrofolate reductase; mthfr (607093). v-akt murine thymoma viral oncogene homolog 1; akt1 (164730). digeorge syndrome; dgs digeorge syndrome chromosome region, included; dgcr, included (188400). mental retardation, x-linked 30; mrx30 (300558). cholinergic receptor, neuronal nicotinic, alpha polypeptide 7; chrna7 (118511). hyperprolinemia, type i; hpi (239500). wolfram-like syndrome, autosomal dominant; wfsl (614296). darier-white disease; dar darier disease, acral hemorrhagic type, included (124200). zinc finger dhhc domain-containing protein 8; zdhhc8 (608784). fxyd domain-containing ion transport regulator 6; fxyd6 (606683). daoa antisense ma; daoaas (607415). atp-binding cassette, subfamily a, member 13; abca13 (607807). deafness, autosomal recessive 47; dfnb47 (609946). brain-derived neurotrophic factor; bdnf (113505). trace amine-associated receptor 6; taar6 (608923). dopamine receptor d4; drd4 (126452). apolipoprotein e; apoe apolipoprotein e, deficiency or defect of, included (107741). synapsin iii; syn3 (602705). protein phosphatase 3, catalytic subunit, gamma isoform; ppp3cc (114107). potassium channel, calcium-activated, intermediate/small conductance, subfamily n, member 3; kcnn3 (602983). serine racemase; srr (606477). chromosome 16p13.3 duplication syndrome (613458). chromosome 16p13.3 deletion syndrome, proximal (610543). n-ethylmaleimide-sensitive factor; nsf (601633). clathrin interactor 1; clint1 (607265). translin-associated factor x; tsnax (602964). glutamate-cysteine ligase, modifier subunit; gclm (601176). kiaa0513 gene; kiaa0513 (611675). notch, drosophila, homolog of, 4; notch4 mouse mammary tumor virus integration site 3, included (164951). v-erb-b2 avian erythroblastic leukemia viral oncogene homolog 4; erbb4 (600543). dopamine receptor d2; drd2 (126450). heat-shock 70-kd protein 6; hspa6 (140555). vasoactive intestinal peptide receptor 2; vipr2 (601970). chromosome 15q11-q13 duplication syndrome autism, susceptibility to, 4, included; auts4, included (608636). cholinergic receptor, muscarinic, 1; chrm1 (118510). neuregulin 3; nrg3 (605533). chromosome 15q13.3 deletion syndrome (612001). heat-shock 70-kd protein 7; hspa7 (140556). chromosome 16p11.2 duplication syndrome autism, susceptibility to, 14b, included; auts14b, included (614671). chromosome 22q11.2 duplication syndrome (608363). gephyrin; gphn mll/gphn fusion gene, included (603930). swi/snf-related, matrix-associated, actin-dependent regulator of chromatin, subfamily a, member 2; smarca2 (600014). kiaa0391 gene; kiaa0391 (609947). g protein-coupled receptor 50; gpr50 (300207). neuronal pas domain protein 3; npas3 (609430). oligodendrocyte lineage transcription factor 2; olig2 (606386). velocardiofacial syndrome (192430). major affective disorder 1; mafd1 (125480). glutamate-cysteine ligase, catalytic subunit; gclc (606857). reelin; rein (600514). fasciculation and elongation protein zeta 1; fez1 (604825). chromosome 16p11.2 deletion syndrome, 593-kb autism, susceptibility to, 14a, included; auts14a, included (611913). digeorge syndrome critical region gene 8; dgcr8 (609030). tyrosine 3-monooxygenase/tryptophan 5-monooxygenase activation protein, epsilon isoform; ywhae (605066). mlc1 gene; mlc1 (605908). dopamine receptor d1; drd1 (126449). guanine nucleotide-binding protein, alpha-activating activity polypeptide, olfactory type; gnal (139312). phosphodiesterase 4b, camp-specific; pde4b (600127). glutamate receptor, metabotropic, 3; grm3 (601115). nitric oxide synthase 1 (neuronal) adaptor protein; nos1ap (605551). glutamate receptor, ionotropic, n-methyl-d-aspartate, subunit 1; grin1 (138249). paired-like homeobox 2b; phox2b (603851). calcium/calmodulin-dependent protein kinase ii-beta; camk2b (607707). neurexin ii; nrxn2 (600566). line retrotransposable element 1; lre1 (151626). nde1-like 1; ndel1 (607538). tryptophan hydroxylase 1; tph1 (191060). nitric oxide synthase 1; nos1 nitric oxide synthase, neuronal, included (163731). hand skill, relative; hsr (139900). monoamine oxidase b; maob (309860). quaking, mouse, homolog of; qki (609590). chromosome 3q29 deletion syndrome (609425). ataxin 1; atxn1 atxn1, alternative reading frame, included (601556). abelson helper integration site 1; ahi1 (608894). congenital anomalies of kidney and urinary tract, susceptibility to; cakut (610805). dna methyltransferase 1; dnmt1 (126375). rel-silencing transcription factor; rest (600571). v-src avian sarcoma (schmidt-ruppin a-2) viral oncogene; src (190090). autism autism, susceptibility to, 1, included; auts1, included (209850). drug metabolism, poor, cyp2d6-related drug metabolism, ultrarapid, cyp2d6-related, included (608902). metachromatic leukodystrophy pseudoarylsulfatase a deficiency, included (250100). major depressive disorder; mdd seasonal affective disorder, included; sad, included (608516). pericentriolar material 1; pcm1 pcm1/ret fusion gene, included (600299). potassium channel, voltage-gated, subfamily h, member 2; kcnh2 (152427). muscular dystrophy, becker type; bmd (300376). apolipoprotein 1-i; apol1 (603743). retinoic acid-induced gene 1; rai1 (607642). solute carrier family 6 (neurotransmitter transporter, serotonin), member 4; slc6a4 (182138). dopamine beta-hydroxylase, plasma; dbh (609312). ciliary neurotrophic factor; cntf (118945). proopiomelanocortin; pomc melanotropin, included (176830). amyloid beta a4 precursor protein; app (104760). methyl-cpg-binding protein 2; mecp2 (300005). tardive dyskinesia (272620). 5-hydroxytryptamine receptor 4; htr4 (602164). regulator of g protein signaling 4; rgs4 (602516). mental retardation, x-linked, syndromic, raymond type; mrxsr (300799). chma7/fam7a fusion gene; chrfam7a (609756). major affective disorder 2; mafd2 (309200). branched-chain ketoacid dehydrogenase kinase deficiency; bckdkd (614923). frizzled, *drosophila*, homolog of, 3; fzd3 (606143). neurochondrin; ncdn (608458). epilepsy, nocturnal frontal lobe, 2; enfl2 (603204). phospholipase c, beta-1; plcb1 plcb1a, included (607120). ubiquitin-specific protease 14; usp14 (607274). 5-hydroxytryptamine receptor 2c; htr2c (312861). epidermal growth factor; egf (131530). protein phosphatase 1, regulatory subunit 1b; ppp1r1b (604399). twinning, monozygotic (276410). 5-hydroxytryptamine receptor 3a; htr3a (182139). cholecystokinin a receptor; cckar (118444). leukoencephalopathy with ataxia; lkpat (615651). parkinson disease 17; park17 (614203). glutamate receptor, metabotropic, 2; grm2 (604099). novelty seeking personality trait risk-taking behavior, included (601696). retinoid x receptor, gamma; rxrg (180247). parvalbumin; pvalb (168890). transcription factor sp4; sp4 (600540). autism, susceptibility to, x-linked 5; autsx5 (300847). conotruncal heart malformations; cthm truncus arteriosus communis, included (217095). glutamate receptor, ionotropic, kainate 1; grik1 (138245). calcitonin/calcitonin-related polypeptide, alpha; calca calcitonin gene-related peptide, included; cgrp, included (114130). nadph oxidase 1; nox1 (300225). retinoid x receptor, beta; rxrb (180246). chromosome 16p12.1 deletion syndrome, 520-kb fragile site 16p12, included (136570). zinc finger dhhc domain-containing protein 9; zdhhc9 (300646). basal ganglia calcification, idiopathic, 1; ibgc1 (213600). chromosome xq28 duplication syndrome (300815). ossified ear cartilages with mental deficiency, muscle wasting, and bony changes (259050). retinoic acid receptor, beta; rarb (180220). dishevelled 1; dvl1 (601365). glutamate decarboxylase 1; gad1 (605363). neurodegeneration with brain iron accumulation 3; nbia3 (606159). medullary cystic kidney disease 1; mckd1 (174000). dopamine receptor d5; drd5 dystonia, primary cervical, included (126453). synaptic ras-gtpase-activating protein 1; syngap1 (603384). colony-stimulating factor 2 receptor, alpha; csf2ra (306250). saethre-chotzen syndrome; scs saethre-chotzen syndrome with eyelid anomalies, included (101400). synaptosomal-associated protein, 25-kd; snap25 (600322). hashimoto thyroiditis thyroid autoantibodies, included (140300). gamma-aminobutyric acid receptor, gamma-2; gabrg2 (137164). frontotemporal dementia; ftd pick complex, included (600274). neuropeptide y; npy (162640). t-box 1; tbx1 (602054). phelan-mcdermid syndrome (606232). solute carrier family 6 (neurotransmitter transporter, dopamine), member 3; slc6a3 (126455). ataxin 8 opposite strand; atxn8os (603680). circadian locomotor output cycles kaput; clock (601851). ferritin light chain; ftl (134790). orofacial cleft 1; ofc1 (119530). wfs1 gene; wfs1 (606201). arylsulfatase a; arsa (607574). nuclear receptor subfamily 0, group b, member 1; nr0b1 (300473). huntington disease; hd (143100). alzheimer disease; ad alzheimer disease, familial, 1, included; ad1, included (104300). apolipoprotein 1-vi; apol6 (607256). apolipoprotein 1-v; apol5 (607255). heparan sulfate 6-o-sulfotransferase 3; hs6st3 (609401). micro ma 130b; mir130b (613682). trace amine-associated receptor 5; taar5 (607405). breast carcinoma amplified sequence 1; bcas1 (602968). apolipoprotein 1-iii; apol3 (607253). coiled-coil domain-containing protein 141; ccdc141 (616031). arginine/serine-rich coiled-coil protein 1; rsrc1 (613352). daz-interacting protein 1; dzip1 (608671). rho gtpase-activating protein 18; arhgap18 (613351). g protein-coupled receptor 85; gpr85 (605188). homer, *drosophila*, homolog of, 3; homer3 (604800). rogdi, *drosophila*, homolog of; rogdi (614574). homer, *drosophila*, homolog of, 2; homer2 homer2a, included (604799). kohlschutter-tonz syndrome; ktzs (226750). membrane-associated guanylate kinase, ww and pdz domains-containing, 1; magi1 (602625). brachydactyly-mental retardation syndrome; bdmr chromosome 2q37 deletion syndrome, included (600430). myelin-associated glycoprotein; mag (159460). solute carrier family 25 (mitochondrial carrier, citrate transporter), member 1; slc25a1 (190315). coiled-coil domain-containing protein 88a; ccdc88a (609736). homer, *drosophila*, homolog of, 1; homer1 homer1a, included (604798). tata box-binding protein; tbp (600075). traf3-interacting protein 2; traf3ip2 (607043). homocystinuria due to deficiency of n(5,10)-methylenetetrahydrofolate reductase activity mthfr deficiency, thermolabile type, included (236250). nude, *a. nidulans*, homolog of, 1; nde1 (609449). coffin-lowry syndrome; cls (303600). glycogen synthase kinase 3-beta; gsk3b (605004). proteolipid protein 1; plp1 dm20, included (300401). spinocerebellar ataxia 1; sca1 (164400)

The present findings, exemplified using as a model the WBS and 7dupASD conditions, may be extrapolated to any autistic and schizophrenia pathology. In fact, although ASD and SZ may be caused by CNV and or point mutations in a large number of genes or loci (currently adding up to the 275 loci or genes listed above), the core symptoms of ASD and SZ are very similar regardless of the causing CNV/mutation. This suggests a high degree of molecular convergence in the pathological mechanism and supports much current effort in defining nodes of dysregulation that, while originally identified in a specific ASD or SZ subset, may obtain also in other forms of either ASD or SZ even when caused by a different genetic lesion[17-20].

In the present invention a cortical neural progenitor cell means a cell derived from human iPSC upon differentiation into the neural lineage, and expressing at least one of the following defining markers: PAX6, SOX2, FOXG1, OTX2, CDC42, RAC1, ZO1.

In the present invention a neural crest stem cell means a cell derived from human iPSC upon differentiation into the neural crest lineage, and expressing at least both of the following defining markers: HNK1 and NGFR.

In the present invention a mesenchymal stem cell means a cell derived from human iPSC upon differentiation into the mesenchymal lineage, and expressing at least both of the following defining markers: CD44 and CD73.

In the method of screening of the invention, the step c) of measuring the level of expression of at least one gene as defined in the claim may be performed by measuring mRNA by qRT-PCR or by high throughout, barcode-enabled RNA sequencing or by any other method known in the art.

In the method of screening of the invention the control level may be the level of expression of said gene in: i) a neuronal cell derived from an iPSC reprogrammed from a healthy individual (ie. not carrying 7q11.23 CNV); ii) an isogenic control neuronal cell; iii) a mock treated 7dupASD or WBS iPSC.

In the present invention "analyzing neural differentiated iPSC-derived cells for morphology and/or function" means quantitatively assessing neuronal networks, dendritic spine density, synapses, soma size, neuronal excitation, or calcium signaling, electrophysiological parameters. Neurodevelopmental disorders encompass a wide range of human diseases characterized by abnormal development of the nervous system, especially the cortex. Autism Spectrum Disorders (ASD), Schizophrenia (SZ) and intellectual disability (ID) are the main neurodevelopmental disorders, displaying specific as well as shared domains of deficit.

In the present invention a LSD1 inhibitor is any known LSD1 inhibitor, for instance described in WO2013057322, WO2011131576, WO2014086790, WO2012135113 and applications EP 14170656.4, EP14193312.7 and EP 14183755.9, included by reference. In particular the general formula and the various definition of substituent, including preferred embodiments disclosed in such documents are part of the present application.

In the present invention a HDAC2 inhibitor is any known HDAC2 inhibitor, for instance those described in Dokmanovic M et al.[21] and Kim H J et al.[22].

The invention will be illustrated by means of non limiting examples in reference to the following figures.

FIG. 1 Patient cohort and expression of 7q11.23 gene interval according to genotype (a) Cohort of recruited patients including the number of independent iPSC clones derived per patients and a diagram showing the repertoire of clinical symptoms and cognitive behavioural traits. Mi stands for mild, Mo stands for moderate. Each genetic condition and the type of genetic rearrangement are represented with specific colors: typical WBS deletion (WBS, red), atypical deletion (AtWBS, orange) and 7q11.23 microduplications (7dupASD, blue). iPSC lines derived from healthy individual are also shown (CTL, green; R stands for relative), as well as external controls (EXT) added for differential expression analysis. (b) Schematic representation of the WBS genetic interval and boundaries of the CNVs detected by aCGH. (c) Nanostring quantification of the expression of genes included in the WBS genomic interval at the iPSC stage. For each gene, 4 bins (1 per genotype) are shown. 1st bin: AtWBS; 2nd bin: WBS; 3rd bin: CTL; 4th bin: 7dupASD. Error bars represent the standard deviation in each genetic condition, while the horizontal bars above the respective comparisons indicate statistical significance. FOV stands for Fields Of View. Two close-by genes outside the CNV were also included (see FIG. 13a for immediately flanking genes).

Figure 2:
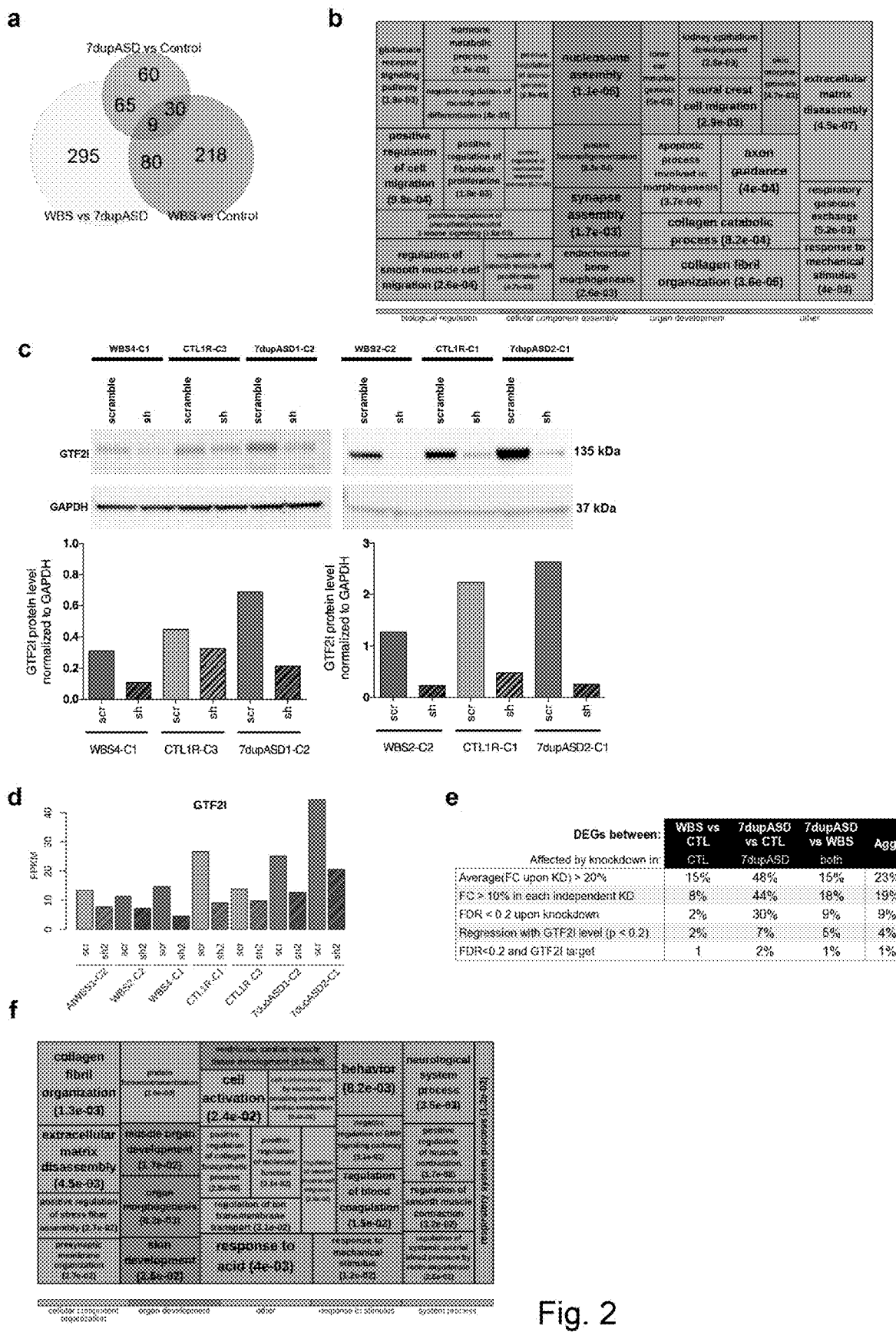

FIG. 2 Analysis of the transcriptomic changes caused by 7q11.13 CNVs and identification of the transcriptional contribution of GTF2I. (a) Number and distribution of differentially-expressed genes (DEGs) among the three comparisons. (b) Top most-specific enrichments for GO biological processes among DEGs. Parent categories with enriched children categories were filtered out; the color code indicates parent categories that have been selected approximating the best non-overlapping combination of parents. DEGs show enrichment for categories recapitulating all aspects of the diseases. (c-d) Validation of GTF2I levels in GTF2I knocked-down (KD) cell lines at both mRNA (RNAseq) (FPKM stands for fragments per kilobase of exon per million fragments mapped) (d) and protein level, including densitometry analysis. (c). The effect of infection on GTF2I mRNA and protein levels was statistically significant according to two-tailed paired T-test. Scr stands for scramble hairpin; sh stands for short hairpin against GTF2I. (e) Proportion of DEGs that are attributable to GTF2I, considering either the (concordant) foldchange (FC) upon KD, differential expression analysis of the KD lines, or linear regression with the GTF2I expression levels across the KD dataset. FDR stands for false discovery rate (f) Top most-specific biological processes enriched in the subset of DEGs attributable to GTF2I (average foldchange above 20%).

Figure 3:
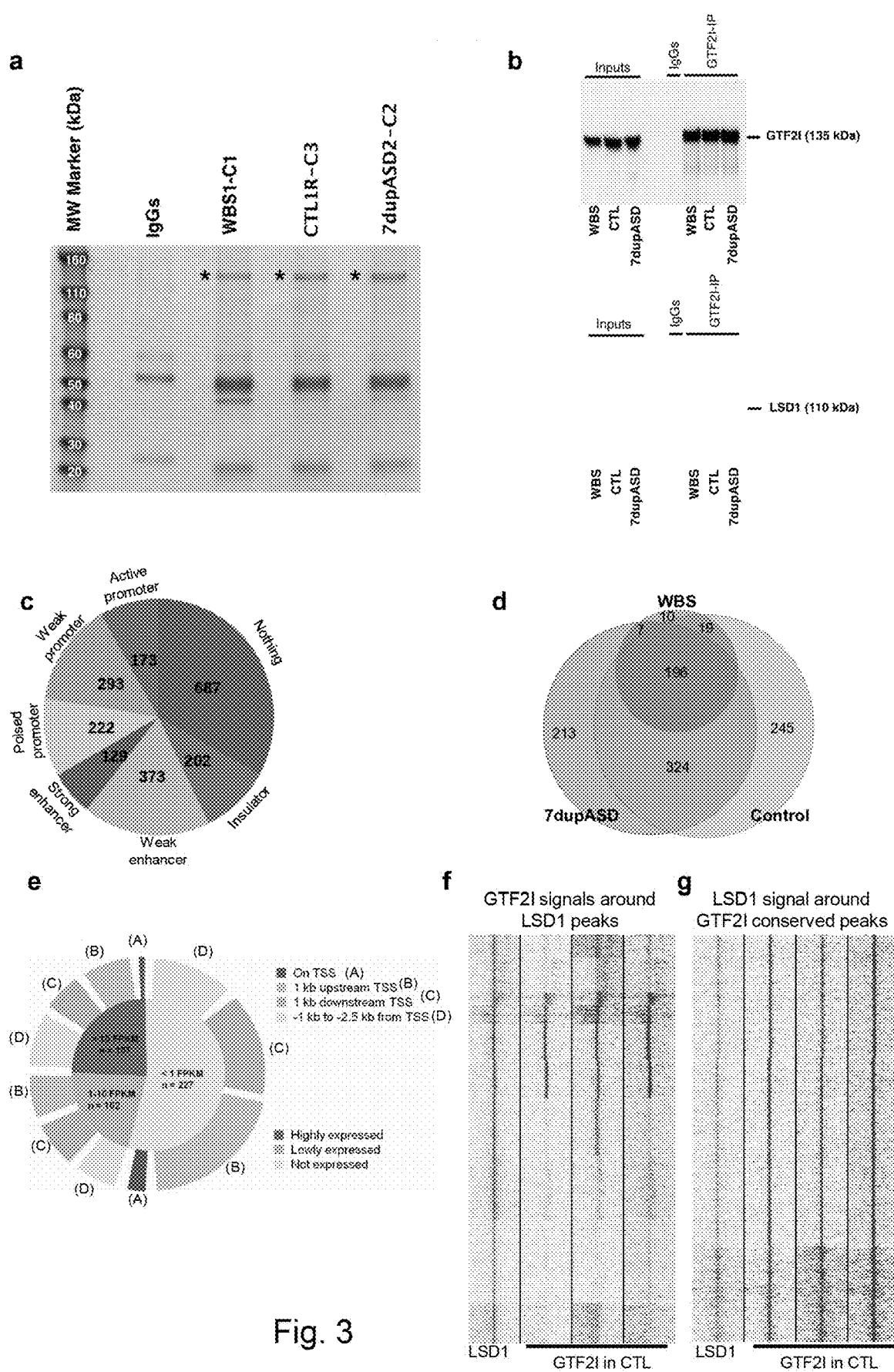

FIG. 3 GTF2I protein complex and its genome-wide occupancy (a) Blue-comassie staining of immuno-precipitated GTF2I complex in representative WBS, control and 7dupASD iPSC lines (one per genotype). Asterisks (*) indicate the bands corresponding to GTF2I. MW stands for molecular weight; IgG stands for immunoglobulin G. (b) Validation of the interaction of GTF2I with LSD1. (c) Distribution of conserved GTF2I peaks on functional elements identified in ENCODE's combined segmentation of the H1 genome. IP stands for immunoprecipitation. (d) GTF2I distribution across all genes that are bound in all samples of a given genotype. (e) Distribution of GTF2I core targets according to their expression level, showing for each expression range the position of the peak relative to Transcription Start Site (TSS). (f) Heatmap of LSD1 (first column) and GTF2I signals (in three control lines) in a +/−5 kb window around LSD1 peaks. (g) Heatmap of LSD1 and GTF2I signals in a +/−5 kb window around conserved GTF2I peaks.

Figure 4:
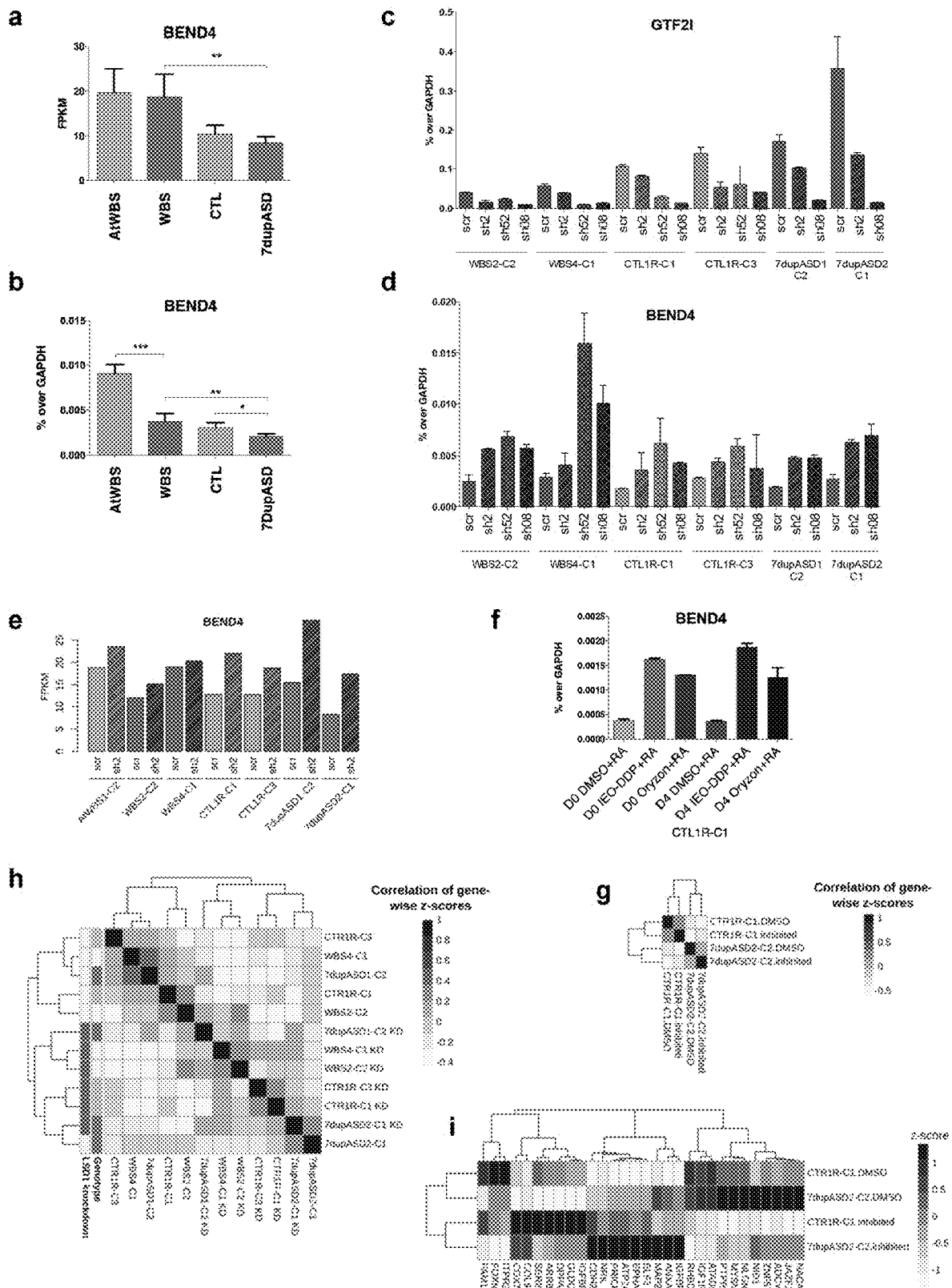

FIG. 4 GTF2I represses BEND4 in a dosage-dependent manner. (a) BEND4 expression in iPSC measured by RNAseq. (b) BEND4 expression in all iPSC lines measured by RT-qPCR. Error bars represent variation between lines of each genotype, and stars indicate statistical significance according to a two-tailed T-test (*: p<0.05, : p<0.01, *: p<0.001). (c) RT-qPCR validation of GTF2I knockdowns using different short hairpins (sh2, sh52 and sh08) on at least two lines per genotype. (d) RT-qPCR validation of BEND4 mRNA levels in the sh2, sh52, sh08-GTF2I knock-down cell lines. (e) RNA-seq measurement of BEND4 expression in the same cell lines. (f) RT-qPCR measurement of BEND4 upon irreversible LSD1 inhibition starting at day 0 (D0) and day 4 (D4) of embryoid body formation in a control iPSC line, showing that in both stages, both inhibitors lead to the upregulation of BEND4. All RT-qPCR levels are reported as percentages of GAPDH. RA stands for retinoic acid. IEO-DDP stands for IEO Drug Discovery Program. In panels c-d-f, error bars represent variation between 2 technical replicates. Similar results were obtained with the Vimentin gene (see FIG. 10). (g) The global correlation of gene-wise z-scores clusters samples according to genetic background rather than whether they were treated with DMSO or the inhibitor, indicating that the LSD1 inhibition is very specific in its effect. (h) Instead, upon LSD1 knockdown using a short hairpins, samples according to treatment, indicating that the LSD1 knockdown has a much more dramatic effect. (i) Among the genes dysregulated in the diseases and attributable (directly or indirectly) to GTF2I, 30 show statistically significant differential expression (using a paired T-test) upon treatment with LSD1.

Figure 5:
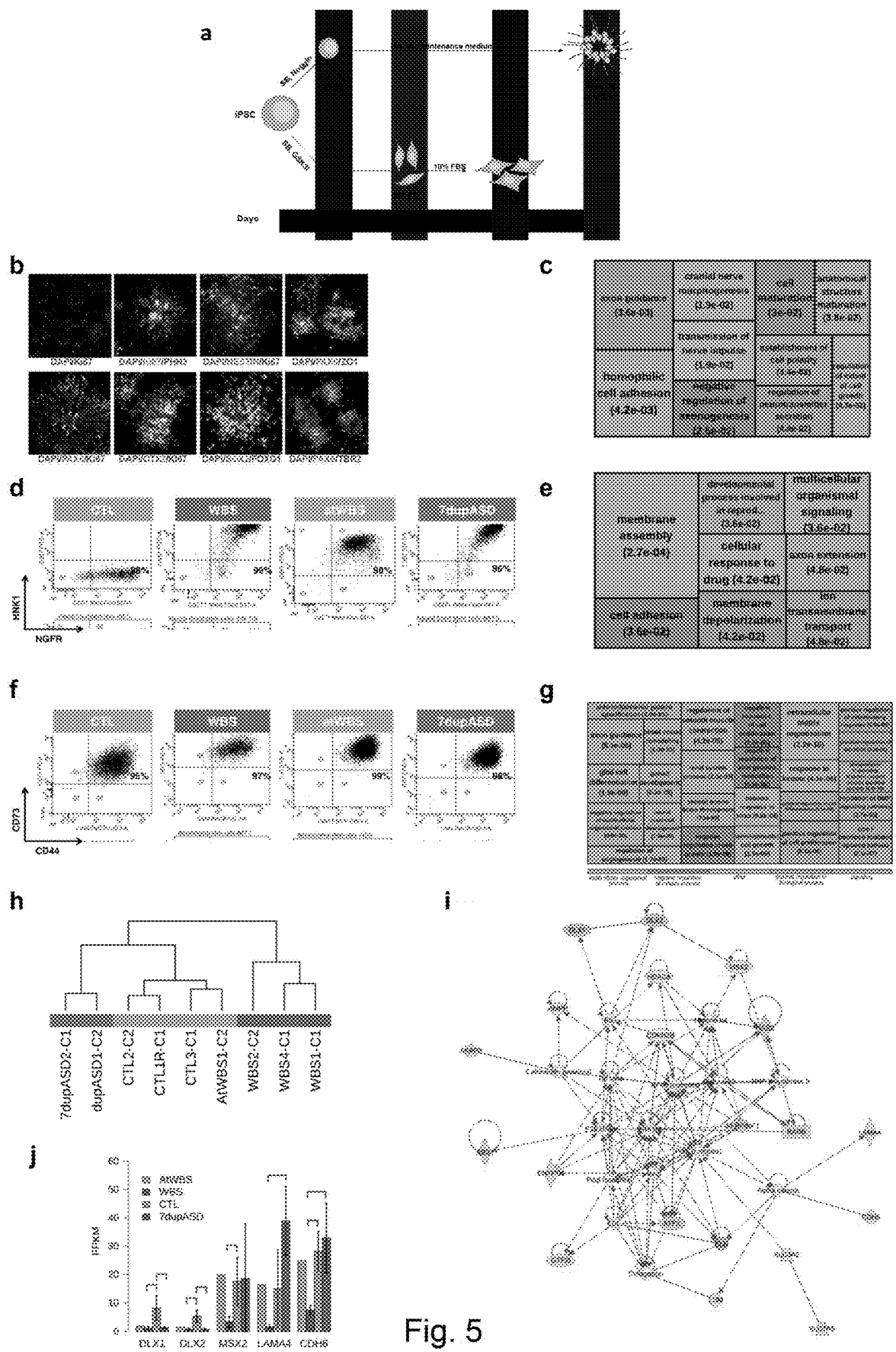

FIG. 5 Derivation and transcriptional characterization of disease-relevant lineages (a) Scheme of iPSCs differentiation protocols toward polarized rosettes (above) or neural crest (NCSC) and mesenchymal stem cells (MSC) (below). FBS stands for Fetal Bovine Serum. (b) iPSC-derived cortical stem/progenitor cells recapitulate the emergence of stem cell populations in human corticogenesis. Rosettes were stained for proliferating (Ki67), mitotic (phospho-histone H3) and neural stem cell (NESTIN, ZO1, and PAX6) markers (above). Default forebrain specification is evidenced by the expression of OTX2, FOXG1 and SOX2 markers (below). (c) Top enrichments for GO biological processes among NPC DEGs. (d-e-f-g) Characterization of patient-specific neural crest stem cells and mesenchymal stem cells. (d) Flow cytometry analysis of NCSC for HNK1 and NGFR markers. Four representative lines for each genotype are shown. (e) Top enrichments for GO biological processes among NCSC DEGs. (f) Flow cytometry analysis of MSCs for CD73$^+$ and CD44$^+$ cells at day 10 of differentiation. (g) Top most specific enrichments for biological processes among the MSC DEGs. (h) Unsupervised hierarchical clustering of correlations between MSCs whole transcriptomes, showing that samples cluster according to their genotype. (i) Ingenuity Pathway Analysis on MSC DEGs reveals a molecular network enriched for cardiovascular system development. (j) Expression of key members of the network in MSC. For each gene, 4 bins (1 per genotype) are shown. 1st bin: AtWBS; 2nd bin: WBS; 3rd bin: CTL; 4th bin: 7dupASD. Error bars represent the standard deviation, while the horizontal bars represent statistical significance.

FIG. 6 Lineage-specific retention of iPSC DEGs. (a) Overlap of DEGs identified in each lineage. (b-c-d) For each differentiated lineage, the treemap of enrichments that had been found among iPSC DEGs (FIG. 2b) is reproduced, plotting as a heatmap the proportion of iPSC DEGs in each category retained through differentiation.

Figure 7:
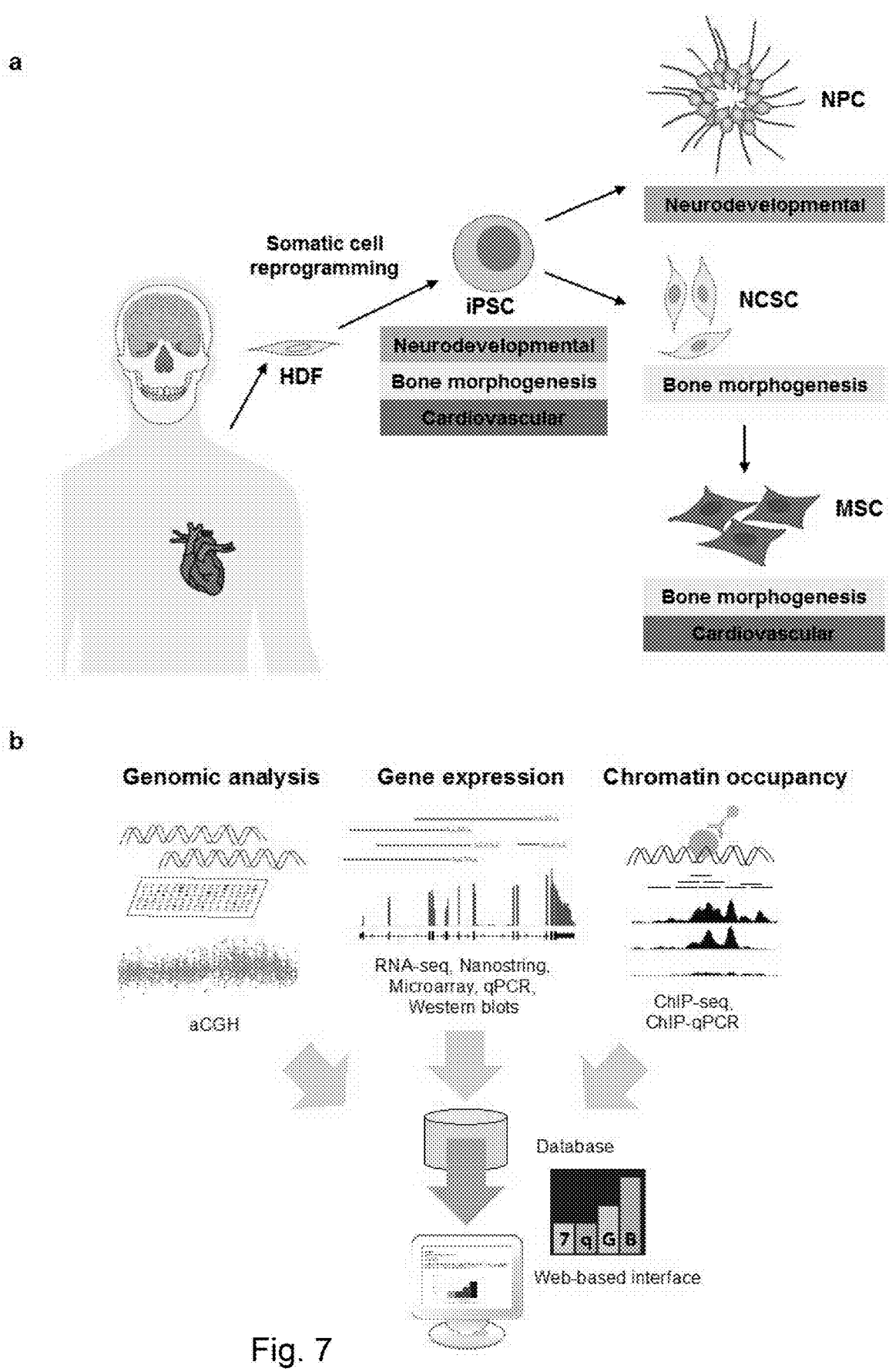

FIG. 7 (a) Graphical representation of the lineage specific retention of DEGs. HDF: Human Derived Fibroblast. (b) Schematic representation of the data gathered in the open-access WikiWilliams/7qGB.

Figure 8:
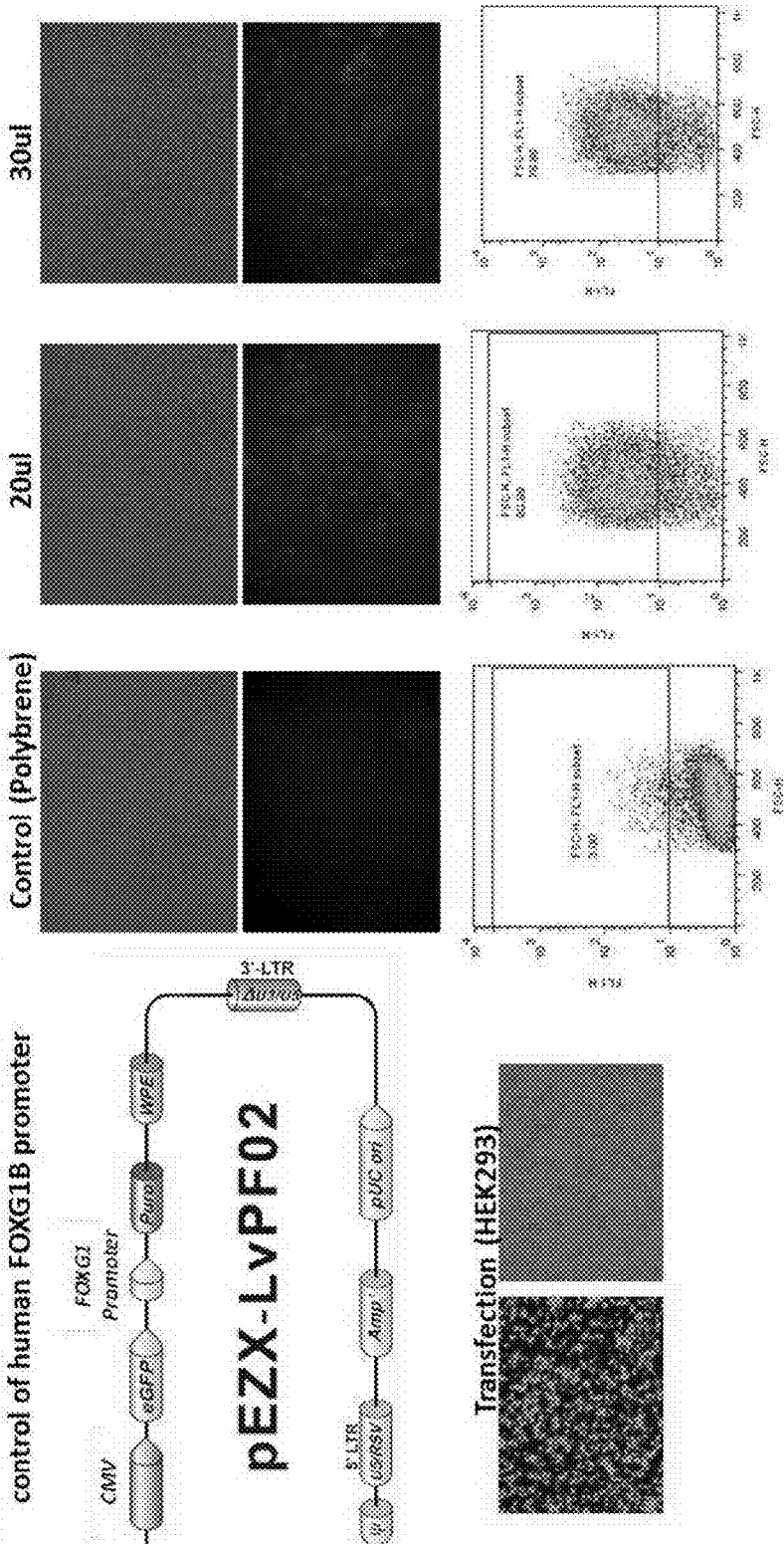

FIG. 8 An approach to isolate iPSC-derived FOXG1-expressing cortical progenitors. The figure describes the proof of principle of experiments aimed at isolating cortical progenitors by selection and FACS sorting. Briefly, the inventors designed a lentiviral construct (upper left scheme) that expresses GFP from a ubiquitous promoter and the puromycinr esistance gene under the control of the FOXG1 promoter. The panels on the right show the infection of a control iPSC line (reprogrammed from a WBS patient relative) with different concentrations of this lentiviral vector, and the assessment of infection efficiency by GFP fluorescence (both by immunofluorescence and FACS, respectively upper and lower panels).

Figure 9:
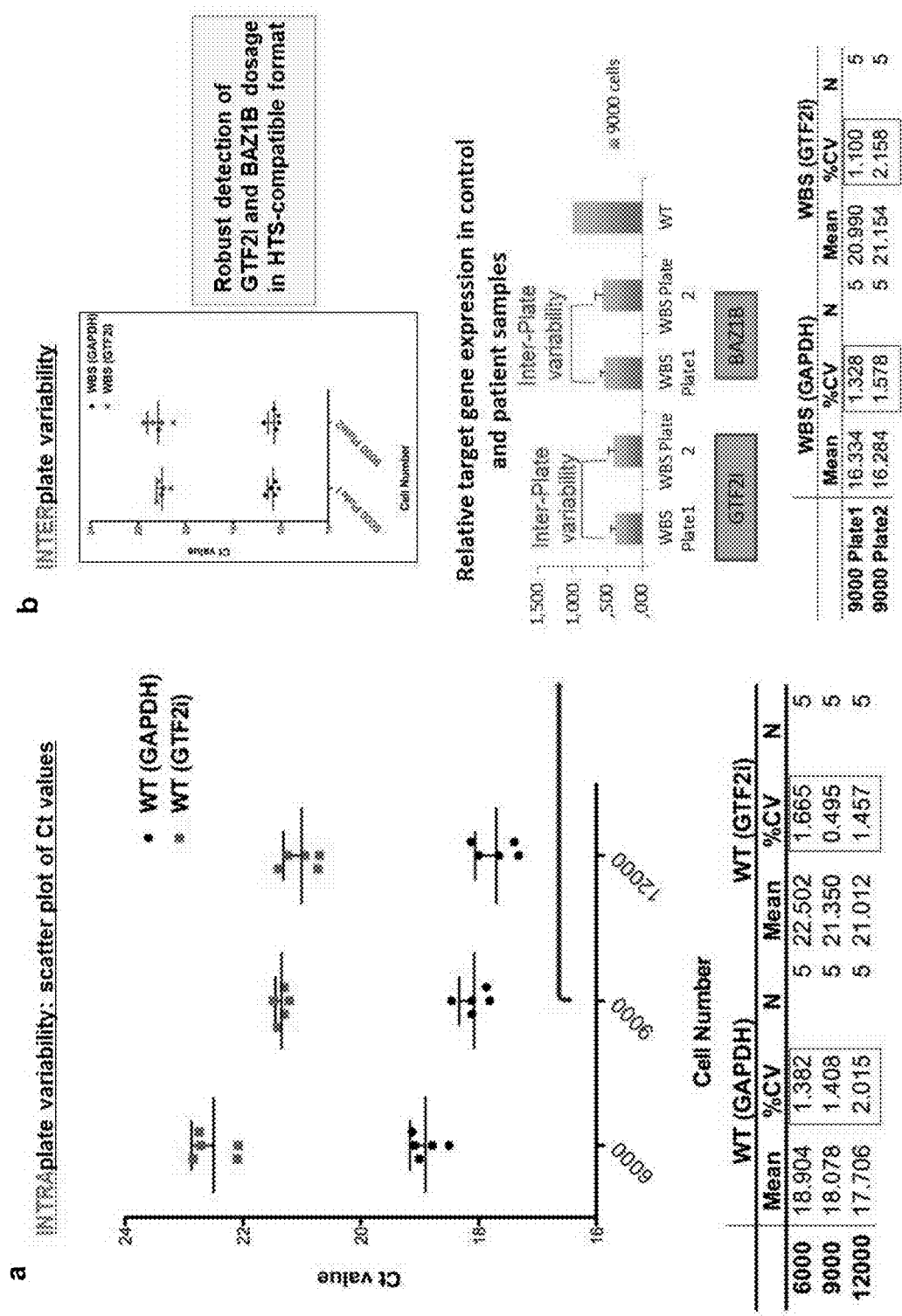

FIG. 9 qRT-PCR-based scoring assay for HTS screening. The figure shows the automated workflow the inventors already validated, for the scoring of the expression of GTF2I and BAZ1B (by multiplex qRT-PCR) in iPSC grown on a 96-well format. This is the format in which the screening will be conducted. (a) The upper left panel shows that, with a very robust 5 replicates test, the inventors were able to measure consistently the levels of GTF2I across 3 different concentrations of seeded iPSC (from 6.000 to 12.000), finding the expected linear relationship between number of cells and GTF2I expression, with excellent consistency across different wells of the same plate. (b) The upper right panel shows that even across wells from different plates qRT-PCR measurements are extremely consistent. The middle right panel shows that expression of both GTF2I and BAZ1B can be very reproducibly measured across 2 different plates seeded with iPSC reprogrammed from WBS patients. Expression levels were compared to those from wild type control iPSC cells and confirmed reproducible halving of expression dosage in WBS iPSC for both GTF2I and BAZ1B. The tables below display the quantification of these data, showing minimal coefficient of variation (CV) across both intra- and inter-plate measurements.

FIG. 10 (a) GTF2I-mediated BEND4 regulation is dependent on LSD1. (upper panel) BEND4 levels are increased upon LSD1 inhibition using two LSD1 irreversible inhibitors to a final concentration of 5 uM (Oryzon) and 10 uM (DDP26095). Treatments were performed for 5 days at day 0 and day 4 of a Embryoid Bodies (EBs) formation assay. Similar results were obtained for ICAM1 and VIM (vimentin) without (Lower panel left) or in the presence of Retinoic Acid (RA), added to a final concentration of 10 uM for 5 days (Lower panel right). (b) GTF2I and LSD1 negatively regulate target genes expression. Proposed model representing the mechanism of action of the GTF2I/LSD1 complex on target genes (BEND4 is shown as a representative target). The GTF2I-LSD1 complex represses target genes by binding to their promoter regions, as exemplified in the upper panel when a control scrambled sh RNAi hairpin is administered to the cells. The middle panel shows relief from transcriptional repression upon GTF2I knock-down accomplished with a specific sh RNAi hairpin targeting GTF2I. The lower panel shows the same result obtained by chemical LSD1 inhibition with the two inhibitors shown in FIG. 10a.

FIG. 11 Establishment of clonal NGN2-transduced inducible iPSC lines. (a) Schematic representation of the strategy to establish clonal lines in which the NGN2 transgene and its coactivator are stably integrated by lentiviral transduction. Infected iPSC lines are expanded, sorted as single cells to create clones, and subsequently 3-5 clones per line are tested for GFP activation. GFP-positive clones are then expanded and frozen for subsequent large-scale differentiation experiments. Genomic DNA can be extracted to quantify the number of integration events across clones by digital PCR. (b) The GFP signal can be seen from day 2 after induction, whereas at day 21 induced clonal NGN2-transduced lines express mature neuronal markers such as MAP2, TUJ1 and the glutamatergic marker VGLUT.

Figure 12:
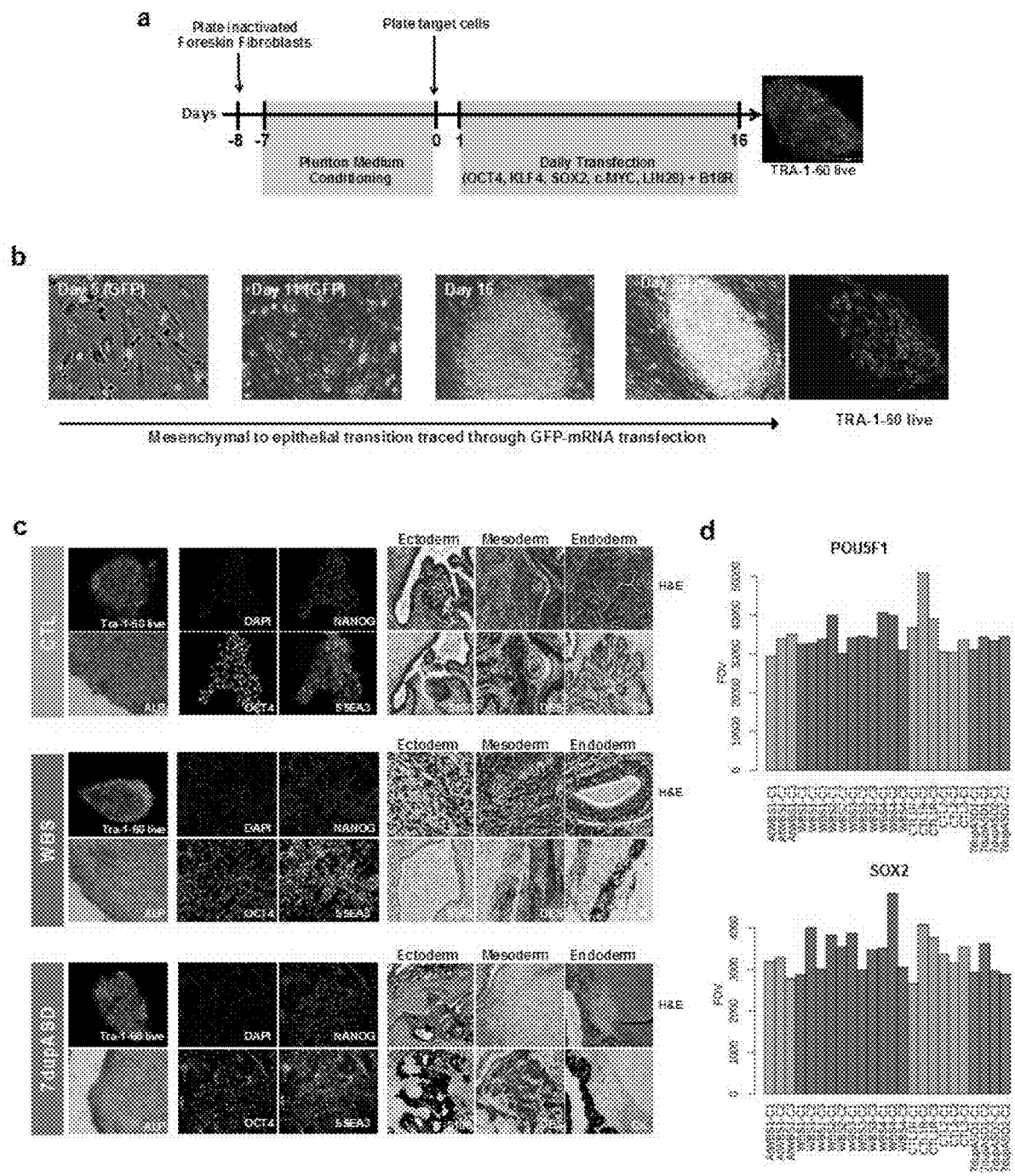

FIG. 12 iPSC lines derivation. (a) Schematic representation of mRNA mediated reprogramming. (b) GFP tracking of mesenchymal-to-epithelial transition. (c) For each genetic condition, expression of alkaline phosphatase (ALP) by immunohistochemistry, immunofluorescence for pluripotency markers, and staining of three representative iPSC-derived teratomas expressing markers specific for the three germ layers (right). H&E: Hematoxylin&Eosin. DES: desmin. CK: cytokeratin. (d) Nanostring measurements for pluripotency markers. FOV: field of view.

Figure 13:
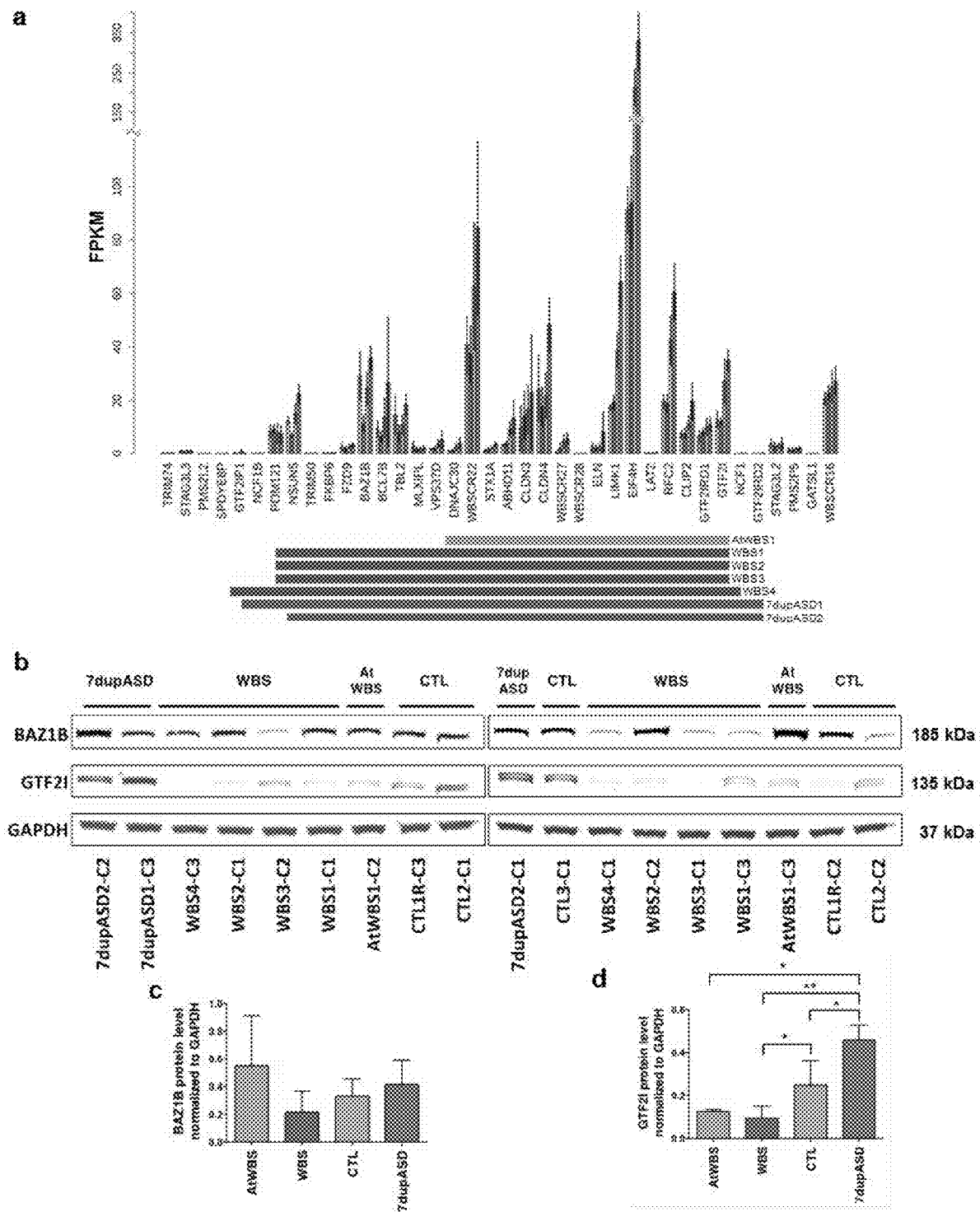

FIG. 13 Expression of genes of the WBS region in iPSC. (a) Expression of genes included in and directly flanking the CNVs as measured by RNA-seq (see Nanostring validation in FIG. 1c). For each gene, 4 bins (1 per genotype) are shown. $1^{st}$ bin: AtWBS; $2^{nd}$ bin: WBS; $3^{rd}$ bin: CTL; $4^{th}$ bin: 7dupASD. The order of genes reflects their relative chromosomal position, and the horizontal color bars indicate which genes are included in the CNVs. (b-c-d) Western blot (b) and densitometry analyses (c-d) of GTF2I and BAZ1B protein levels in a representative subset of iPSC lines. Changes in GTF2I protein levels are statistically significant according to a two-tailed t-test (*: p<0.05, **: p<0.01); differences in BAZ1B protein levels, although showing a clear trend, are not statistically significant in this assay. FPKM: Fragments Per Kilobase Of Exon Per Million Fragments Mapped.

Figure 14:
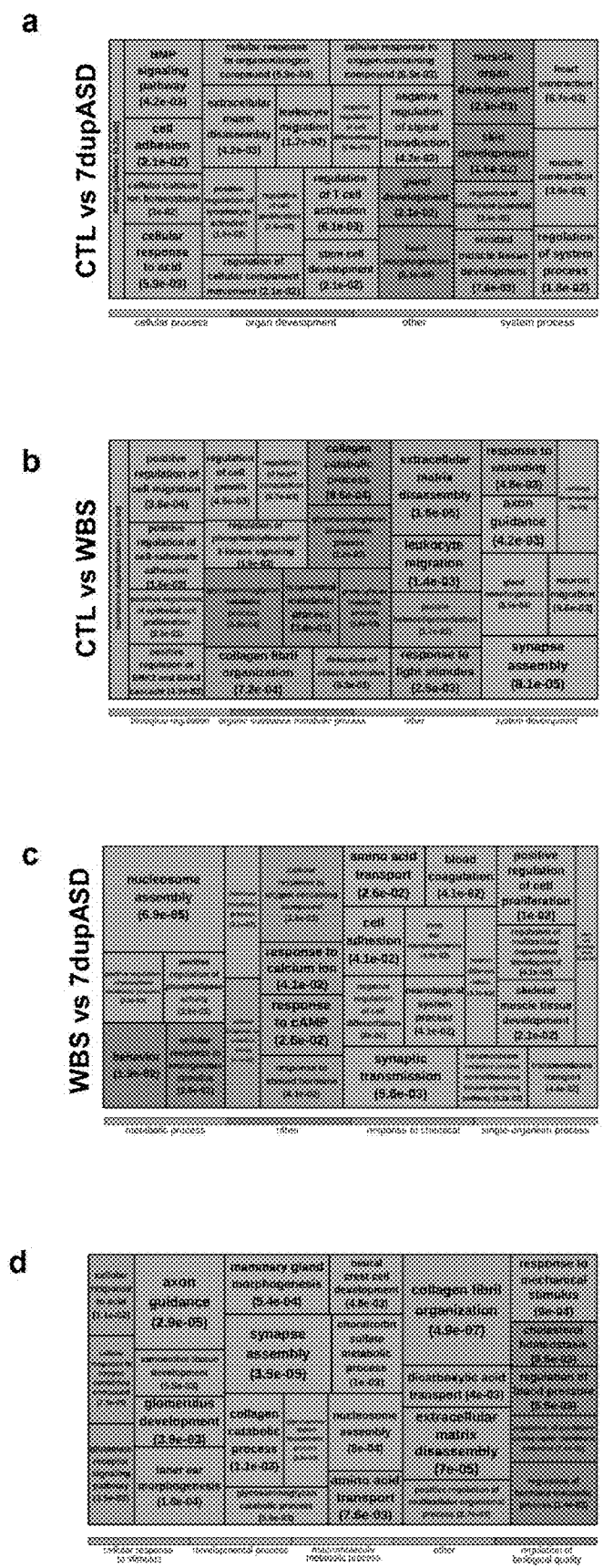

FIG. 14 Transcriptional profiling of patient- and control-derived iPSCs. (a-b-c) GO biological processes enriched among DEGs between Control vs 7dupASD (a), WBS vs Control (b) and WBS vs 7dupASD (c). (d) Enrichment for GO biological processes among the union of DEGs when excluding the external control lines from the analysis.

Figure 15:
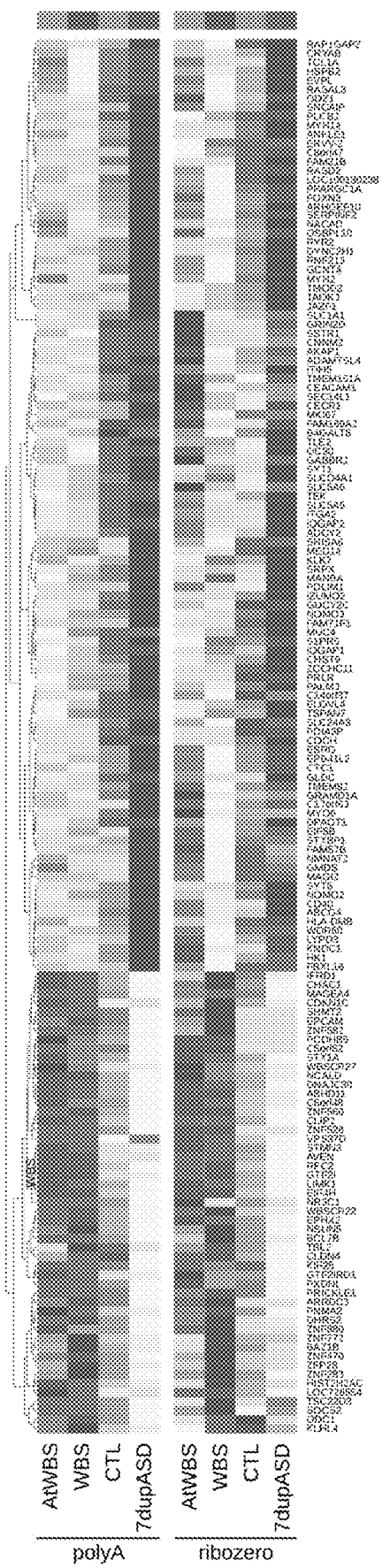

FIG. 15 Genes differentially expressed in a symmetrical manner in WBS and 7dupASD iPSC.

Figure 16:
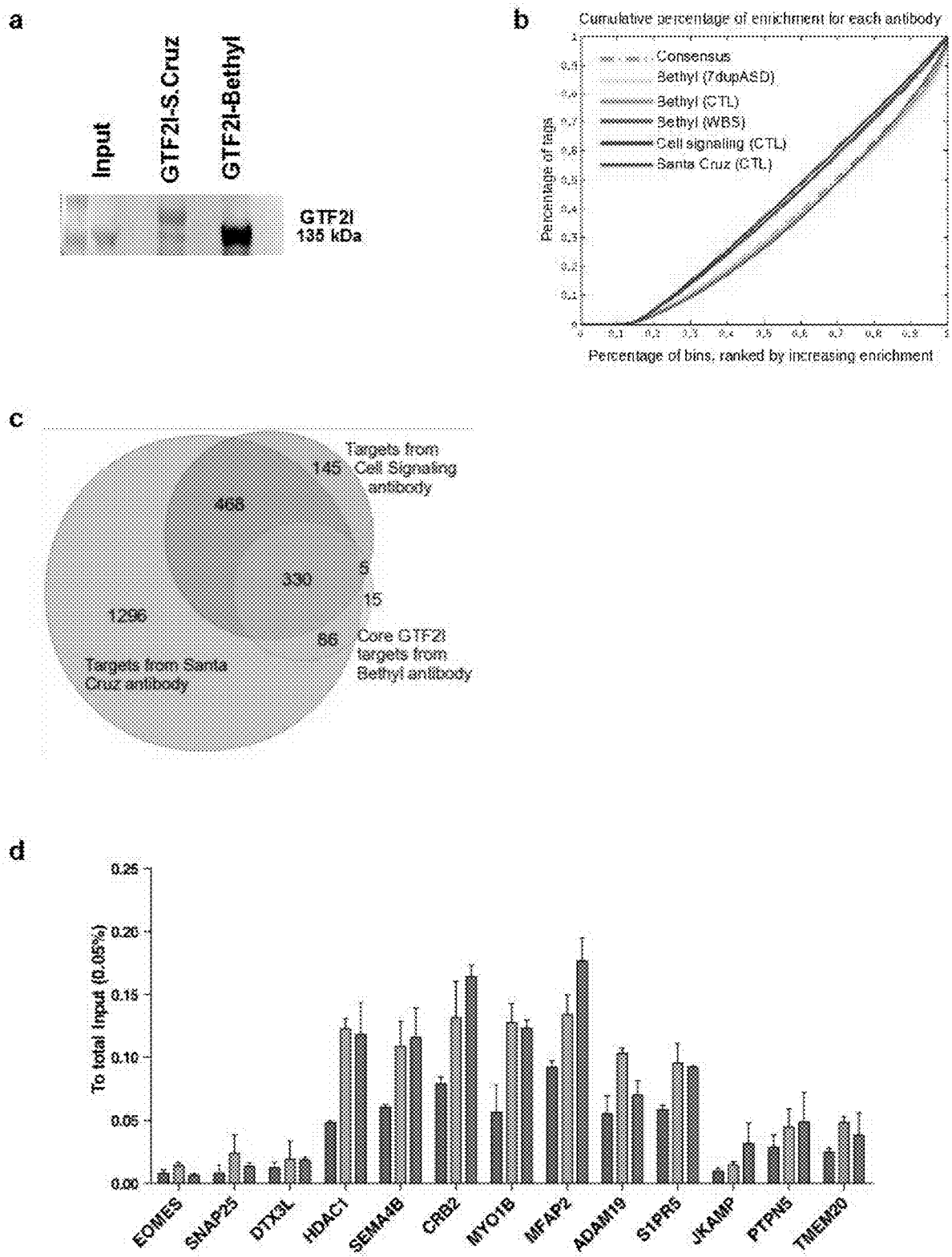

FIG. 16 Comparison of different antibodies assayed for ChIP-Seq and Immunoprecipitation assays. (a) Western blot validation of immunoprecipitation efficiency of two different GTF2I antibodies in a control iPSC line. (b) Most gene targets identified with the Bethyl antibody are also identified with the other antibodies. (c) Enrichment plot showing the distribution of reads across the genome; the samples using the Bethyl antibodies have a distinctively greater degree of enrichment compared with the other samples. (d) ChIP-qPCR validation of core and dosage-sensitive GTF2I targets. EOMES and SNAP25 promoters have been used as negative controls.. For each gene, 3 bins (1 per genotype) are shown. $1^{st}$ bin: WBS; $2^{nd}$ bin: CTL; $3^{rd}$ bin: 7dupASD.

Figure 17:
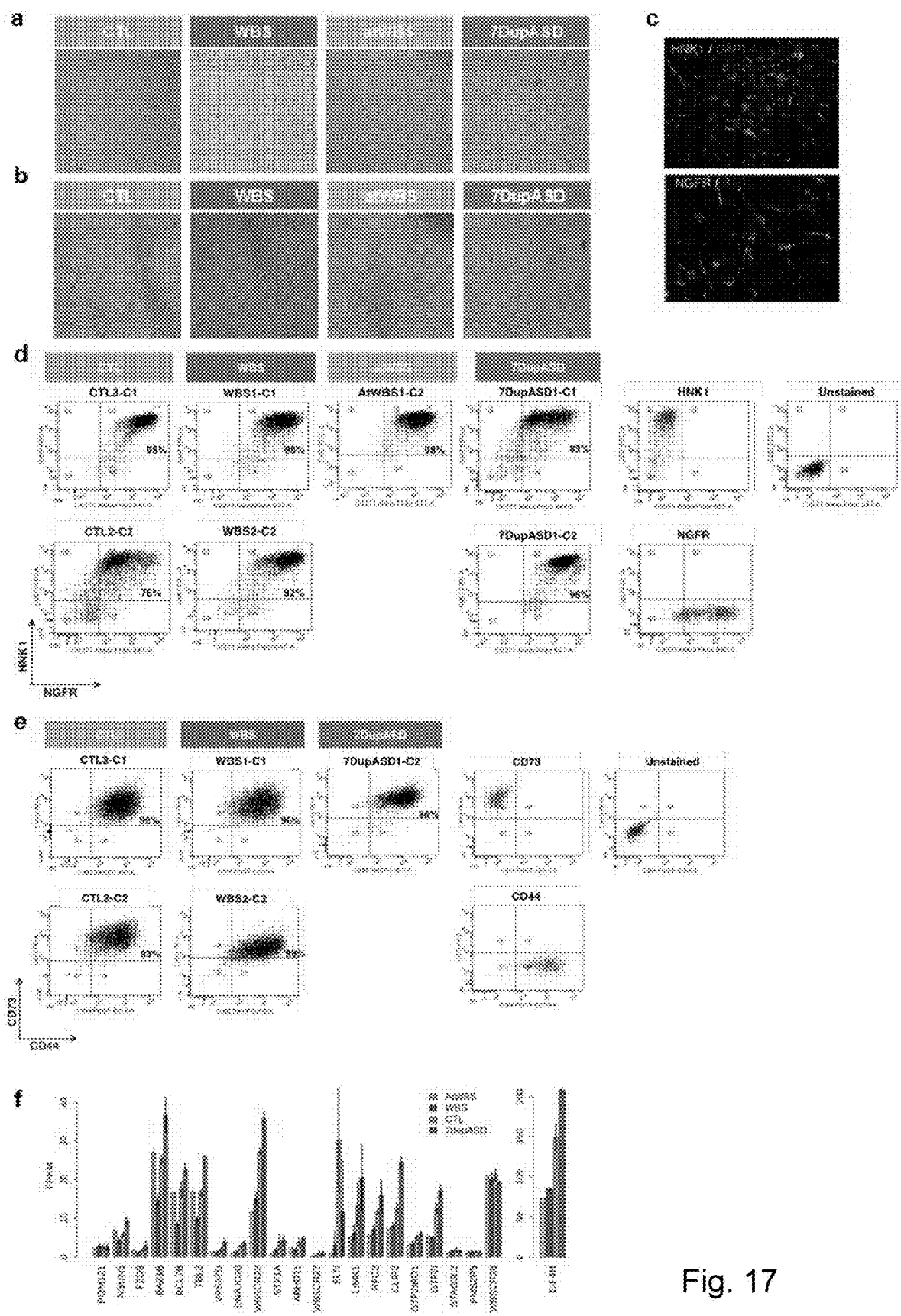

FIG. 17 Characterization of NCSC and MSC lines derived from WBS, atWBS, 7dupASD and control iPSC lines. NCSC (a) and MSC (b) phase contrast microscopy shows a similar morphology between the four genotypes. (c) Immunofluorescence analysis indicates positivity for two NCSC markers (HNK1 and NGFR) in a representative iPSC-derived NCSC line. DAPI stains nuclei, HNK1 and NGFR stain cytoplasm. (d-e) Flow cytometry analysis indicates a high percentage of HNK1-NGFR and CD73-CD44 double positive cells respectively in NCSC (d) and MSC lines (e). (f) Plot of RNAseq expression levels of genes included in the WBS genomic interval at the MSCs stage. For better visualization, genes were separated into low/medium (right panel) and high expression (left panel). For each gene, 4 bins (1 per genotype) are shown. $1^{st}$ bin: AtWBS; $2^{nd}$ bin: WBS; $3^{rd}$ bin: CTL; $4^{th}$ bin: 7dupASD.

Figure 18:
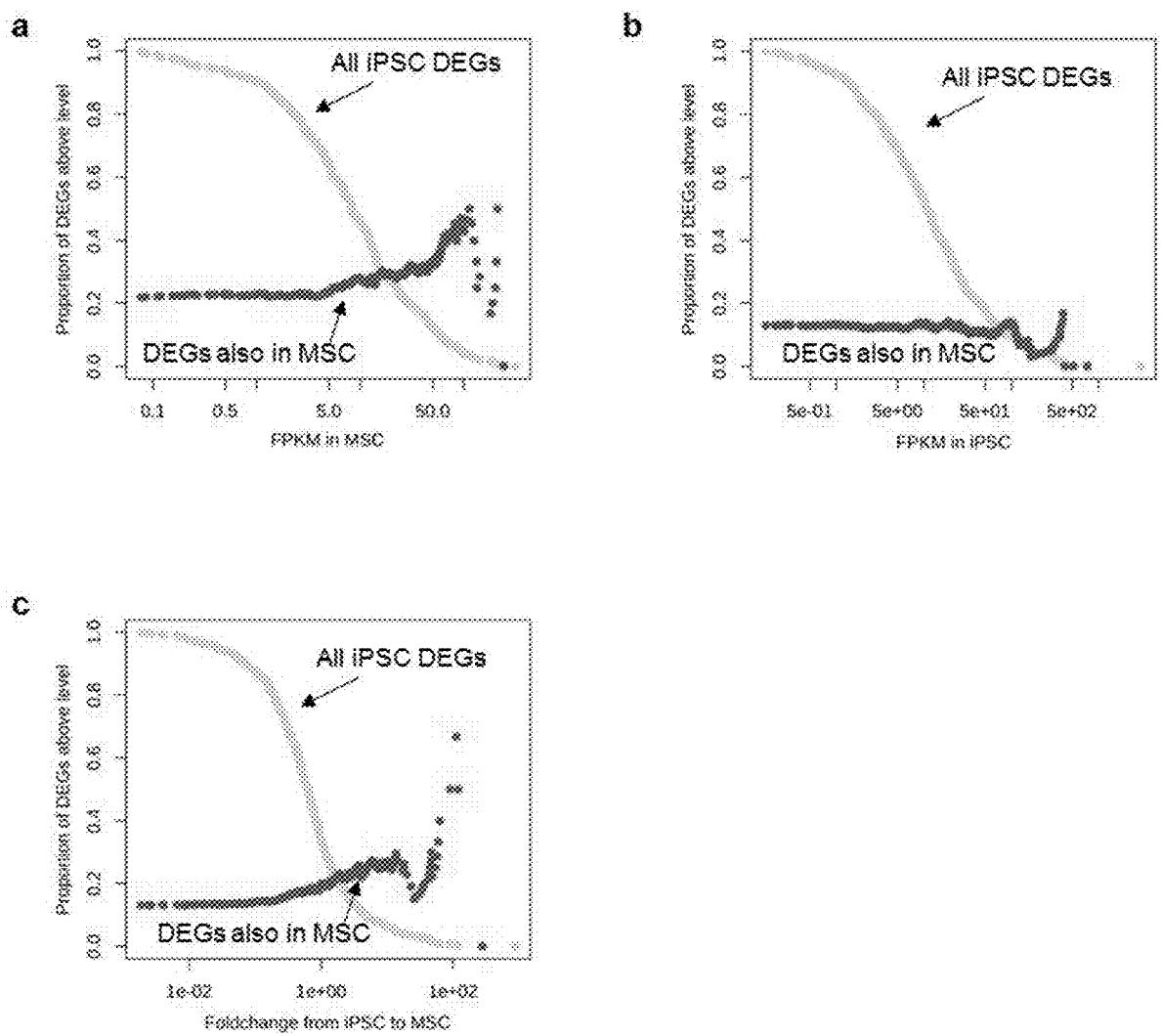

FIG. 18 Characterization of DEGs found in both iPSC and MSC. (a) MSC DEGs that are also DEGs in iPSC have higher expression. (b) The proportion of overlapping DEGs in MSCs does not correlate with expression levels in iPSC. (c) The vast majority of DEGs at the iPSC stage is down-regulated in differentiated MSCs and the overlap between iPSC and MSC DEGs increases with higher fold changes from iPSC to MSC.

Figure 19:
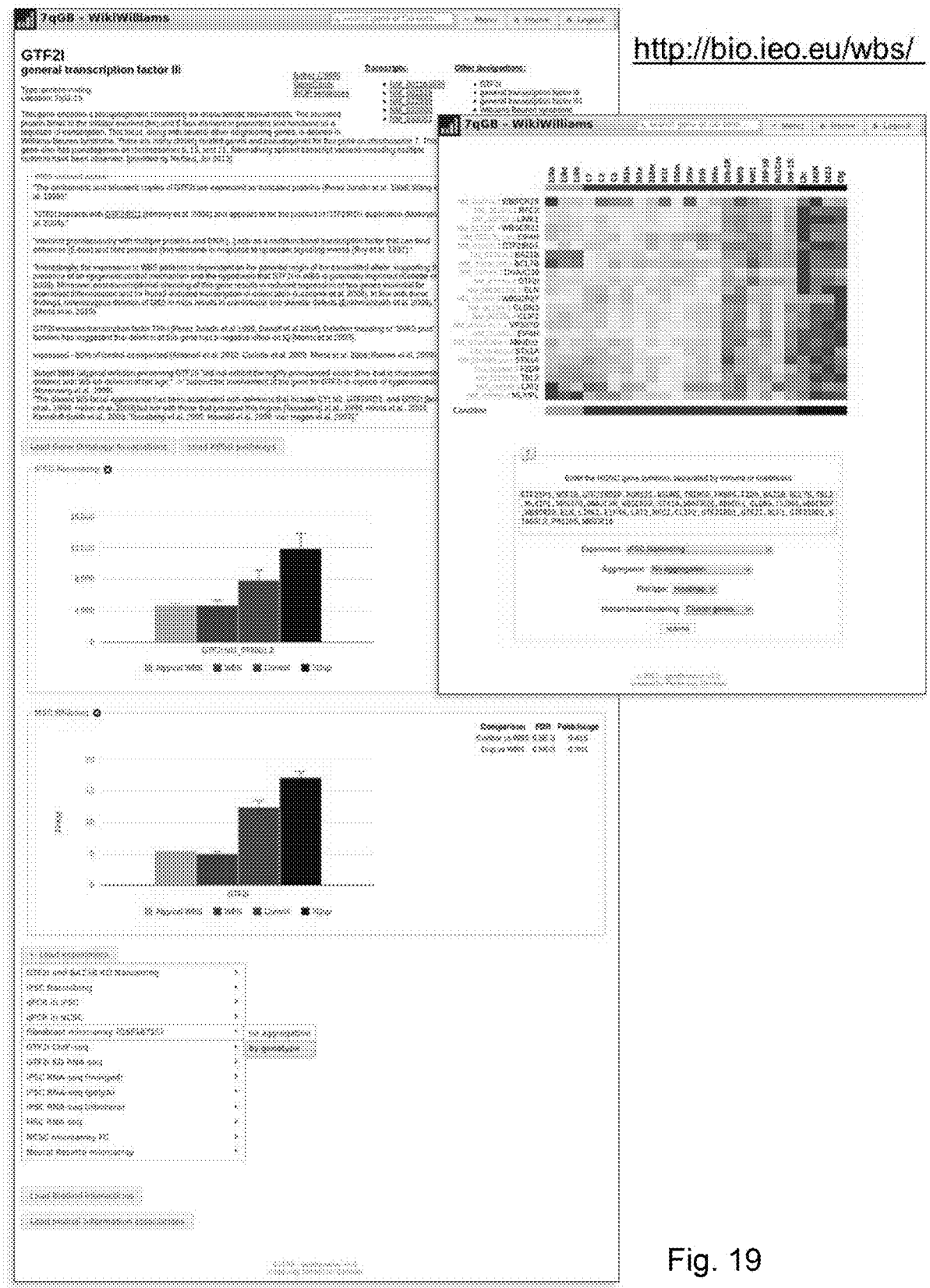

FIG. 19 The WikiWilliams/7q11GB web platform. Representative screenshot of the WikiWilliams/7q11GB database as it appears to users searching for a specific gene of interest. All transcriptomic and genomic data presented in this paper as well as previously published datasets can be easily interrogated in a multi-layered format integrated with several biological databases.

DETAILED DESCRIPTION OF THE INVENTION

Methods

A summary of which experiments were performed on which cell line is given in Table 1.

TABLE 1 list of performed experiments

| Lines | Single cell adaptation | RNA-seq (Ribozero) | RNAseq (PolyA) | CGH array | Nano-string | ChIP-seq | Neural progenitors | Neural crest stem cell | Mesenchymal stem cell | GTF2I scramble interfered iPSC & RNAseq | GTF2I sh2 interfered iPSC & RNAseq |
|---|---|---|---|---|---|---|---|---|---|---|---|
| WBS1 | | | | X | | | | | | | |
| WBS1-C2 | X | X | | X | X | | X | | | | |
| WBS1-C3 | X | X | X | X | X | X | | X | | | |
| WBS1-C1 | X | X | X | X | X | X | X | X | X | | |
| WBS2 | | | | X | | | | | | | |
| WBS2-C3 | | X | | | | | | | | | |
| WBS2-C1 | X | X | | X | X | | | | | | |
| WBS2-C2 | X | X | X | X | X | X | X | X | X | X | X |
| WBS3 | | | | X | | | | | | | |
| WBS3-C3 | X | X | | X | X | | X | | | | |
| WBS3-C1 | X | X | | X | X | | | | | | |
| WBS3-C2 | X | X | X | X | X | X | | | | | |
| WBS4 | | | | X | | | | | | | |

TABLE 1-continued list of performed experiments

| Lines | Single cell adaptation | RNA-seq (Ribozero) | RNAseq (PolyA) | CGH array | Nano-string | ChiP-seq | Neural progenitors | Neural crest stem cell | Mesenchymal stem cell | GTF2I scramble interfered iPSC & RNAseq | GTF2I sh2 interfered iPSC & RNAseq |
|---|---|---|---|---|---|---|---|---|---|---|---|
| WBS4-C3 | X | X | | X | X | | | | | | |
| WBS4-C2 | X | X | | X | X | | | | | | |
| WBS4-C1 | X | X | X | | X | X | X | X | X | X | X |
| AtWBS1 | | | | X | | | | | | | |
| AtWBS1-C2 | X | X | X | X | X | X | X | X | X | X | X |
| AtWBS1-C3 | X | X | X | X | X | | X | X | | | |
| AtWBS1-C1 | X | X | | X | X | | | | | | |
| CTL2-C1 | X | X | | | X | | X | | | | |
| CTL2-C2 | X | X | X | | X | X | X | X | X | | |
| CTL3-C1 | X | | | X | X | | X | X | X | | |
| CTL3-C2 | | X | | X | | | | | | | |
| CTL1R | | | | | | | | | | | |
| CTL1R-C1 | X | | | X | | | X | | X | X | X |
| CTL1R-C2 | X | | X | X | X | X | X | | | | |
| CTL1R-C3 | X | | X | X | X | | | X | | X | X |
| 7dupASD1 | | | | X | | | | | | | |
| 7dupASD1-C1 | X | X | | | X | | X | X | | | |
| 7dupASD1-C3 | | X | | X | | | | | | | |
| 7dupASD1-C2 | X | X | X | X | X | X | X | X | X | X | X |
| 7dupASD2 | | | | X | X | | | | | | |
| 7dupASD2-C4 | | | | X | | | | | | | |
| 7dupASD2-C2 | X | | X | X | X | X | X | | | | |
| 7dupASD2-C3 | | | | X | | | | | | | |
| 7dupASD2-C5 | X | | X | X | X | X | X | X | X | X | X |
| 7dupASD2-C1 | | | | | | | | | | | |

Human Samples

Participation in this study by patients and relatives along with skin biopsy donations and informed consent procedures were approved by the Ethics Committee of the Genomic and Genetic Disorder Biobank (Casa Sollievo della Sofferenza, San Giovanni Rotondo, Italy) and the University of Perugia (Azienda Ospedaliera-Universitaria "S. Maria della Misericordia", Perugia, Italy).

Fibroblast Culture and Reprogramming

Primary fibroblast cell lines WBS1-2-3-4, 7Dup-ASD2, AtWBS1, CTLR were obtained from Genetic Disease Biobank. 7Dup-ASD1 primary fibroblast was obtained from Azienda Ospedaliera-Universitaria "S. Maria della Misericordia", Perugia, Italy. Fibroblasts were cultured in HF medium composed as follows: RPMI 1640, 1% L-Glutamine, 1% Pen-Strep, 15% FBS for few passages before reprogramming.

WBS1-2-3-4, 7Dup-ASD1-2, AtWBS1, CTL1R, and CTL2 fibroblast lines were reprogrammed using mRNA Reprogramming Kit (Stemgent). For reprogramming 7Dup-ASD2 and CTL1R lines microRNA Booster Kit (Stemgent) were used to enhance the reprogramming. CTL3 line was reprogrammed using STEMCCA polycistronic lentiviral vector followed by successful cre-mediated excision of the integrated polycistron. For mRNA-mediated reprogramming epithelial-to-mesenchymal transition was monitored from day 5 by tracing GFP-positive cells. Successfully reprogrammed colonies were assayed for pluripotency at day 20 using a live TRA-1-60 antibody (Stemgent) and selected for further expansion as detailed below.

iPSC Culture iPSC lines were cultured on mitomycin C-inactivated mouse embrionic fibroblasts (MEFs) as previously described[23] in a medium composed as follows: DMEM-F12 (Gibco) in a 1:1 ratio supplemented with 20% KSR, 1% Non Essential Amino Acids, 1% Pen-Strep, 1% Glutamine, 0.1% beta-mercaptoethanol, 10 ng/ml basic fibroblast growth factor (bFGF, Gibco). Colonies were passed and expanded twice by physical fractionation with a sterile needle and replated onto newly seeded MEFs for line establishment. After few passages iPSCs were adapted to grow in feeder-free condition on plates coated with human-qualified Matrigel (BD Biosciences) diluted 1:40 in DMEM-F12 and in mTeSR-1 (StemCell Technologies) medium and were passed by physical fractionation upon a 2 minutes treatment with Dispase (Sigma) at 37° C. Feeder-free iPSCs were also adapted to grow in single cell culture by dissociating them by a 3 minutes treatment with Accutase (Sigma) at 37° C. and finally resuspended in a suitable volume of mTeSR-1 supplemented with 5 μM Y-27632 (Sigma).

Teratoma Assay and Immunohistochemistry

Teratoma assay was performed by subcutaneously injecting 1-3×10⁶ iPSCs in human-qualified Matrigel (BD Biosciences) into the dorsal flanks of NOD-SCID IL2RG male mice. Teratomas were isolated when the diameter reached >1.5 cm and fixed in 4% buffered formalin. Samples were then OCT embedded, sectioned and stained for H&E and germ layer specific antibodies: desmin (Dako), S-100 (Dako) and cytokeratin (Dako).

Immunocytochemistry

Cells were fixed in 4% PFA for 20' and subsequently blocked in 10% FBS+0.1% Triton for 30' at room temperature. Cells were incubated with primary antibodies overnight at 4° C. and then with secondary antibodies for one hour at room temperature. Primary and secondary antibodies were resuspended in 10% FBS. Primary antibodies used were OCT3/4 (SantaCruz), NANOG (Everest Biotech), SSEA3 (Invitrogen), Tra1-60 (Stemgent), TBR2 (Abcam), SOX2 (R&D), PAX6 (HBDS), NESTIN (Abcam), FOXG1 (StemCulture), ZO1 (Invitrogen), OTX2 (Millipore), Ki67 (Abcam), PHH3 (Millipore) HNK1 (SIGMA), NGFr (p75, Advanced Targeting Systems). Alkaline phosphatase staining was performed using Alkaline Phosphatase Detection Kit (Sigma).

Images were acquired at an Olympus AX70 microscope.

DNA, RNA and Protein Extraction

Genomic DNA was extracted from fibroblasts and feeder-free iPSC lines using the DNeasy Blood and Tissue Kit (Qiagen) according to manufacturer specifications. RNA was extracted from iPSC lines using the RNeasy Micro Plus Kit (Qiagen) according to manufacturer specifications, substituting the genomic DNA elimination column by needle and Dnase treatment (Qiagen). Quality and concentration of DNA and RNA was assessed using a NanoDropSpectrophotometer (NanoDrop Technologies).

Proteins were extracted as follows: cells were scraped from the plate and centrifuged at 1100 g at 4° C. for 3 minutes, then washed in PBS and lysed in RIPA buffer plus protease inhibitors cocktail (Sigma) on a spinning wheel at 4° C. for 30 minutes. Lysates were sonicated using the Bioruptor Sonication System (UCD200) for 3 cycles of 30 seconds with 60 seconds breaks at high power. Lysates were centrifuged at 13000 g for 15 minutes and supernatants were transferred to a new tube. Protein quantification was performed using the Bradford protein assay (BioRad) and following manufacturer instructions.

Immunoblotting

For immunoblotting 20 to 40 µg of protein extract per sample were run on a precast Nupage 4-12% Bis-tris Gel (Life Technologies), transferred on a nitrocellulose membrane and blocked in TBS-T and 5% milk. Antibodies used for detection were GTF2I (Cell signalling), BAZ1B (Abcam) and GAPDH (Abcam). Blots were scanned using a LI-COR Odyssey Infrared Imaging System and bands were quantified using ImageJ software.

Nanostring

Nanostring quantification was performed according to manufacturer instructions and data normalization was performed with the nSolver Analysis Software 1.1, using GAPDH, TUBB, and POLR1B as normalizers.

RNAseq

Library preparation for RNA sequencing was performed using Poly-A, RiboZero and Single Stranded kits (Illumina) according to manufacturer instructions.

For the purpose of differential expression analysis, the inventors complemented their polyA dataset with the transcriptomic profiles of three control iPSC lines available from the literature (GEO samples GSM1153507, GSM1153512, and GSM1153513, from cell lines ADRC40, WT-9 and WT-126 respectively), which were selected on the basis of the similarity of their culture conditions and sequencing protocols to ours. The inventors excluded from the analysis genes (292, of which 43 would otherwise be DEGs between genotypes) that were found differentially-expressed between controls from theircohort and external controls.

Reads were aligned to the hg19 transcriptome using TopHat 2.0.10. The alignment was first performed on the RefSeq transcriptome and all the reads that had an edit distance≥1 were realigned on the genome, allowing a maximum read edit distance of 3 and 3 (100 bp reads) and 2 (50 bp reads) maximum mismatches. 50 bp stranded reads (MSC transcriptomes, as well as transcriptomes of the knockdown and inhibited lines) were analyzed using the "fr-firststrand" option. Quantification of reads over the RefSeq transcriptome was performed with Cufflinks 2.2.1 using sequence-bias and multi-read corrections. Differential gene expression was estimated using Cufflinks 2.2.1, using per-condition dispersion models (except for the knockdown experiment in which a global model was used due to the low number of replicates). For the iPSC stage, given the presence of both polyA and Ribo-zero samples, the inventors considered the union of DEGs identified through a global analysis of all samples (FDR<0.05) with those identified through independent analysis of the polyA and Ribo-zero samples. In the latter case, the inventors considered as differentially expressed genes that had a FDR<0.2 in both datasets (comparing the same genotypes), and for which the change was in the same direction.

Downsampling Test

The vast majority of differentially-expressed genes identified in this study were still found when removing the external controls, and most of the remaining DEGs were close to significance, arguing against the introduction of a major bias through the use of external controls.

In order to assess the effect, on the transcriptional analysis, of having fewer samples, the inventors repeated the analysis of their polyA dataset (focusing on the comparison for which the inventors had the most samples, i.e. the global analysis of WBS vs CTL iPSC), using only subsets of the samples. Random removal of 1 clone per patient lead to a dramatic reduction in the number of DEGs (48 to 76% lost), and to the identification of DEGs that are falsified by the discarded data. The impact of removing all clones from one patient per condition (amounting to fewer samples than removing one clone per patient) was even greater. In contrast, depth of sequencing appeared to make little difference: reducing coverage by half led to the loss of 11% of DEGs and to very few false positives.

Shuffling Tests

To assess the possibility that the observed differential expression might arise due to random variations, the inventors performed a series of differential expression analysis between randomly-selected samples, discarding comparisons in which the two groups were not balanced for sex and/or genotype. A minimum of 3 such combinations were tested per tissue, and the resulting genes were pooled for the purpose of enrichment analysis.

At the iPSC stage (using the polyA dataset), the inventors first randomly assigned all patients to two groups, but could the inventors obtain statistically significant genes in none of the combinations. The inventors therefore gradually removed patients until significant genes were obtained, which did not happen until a comparison involving 6 vs 6 samples (in each group, 3 samples from 2 patients). In contrast, when clones were selected and assigned to groups in a way that maximized the number of patients represented in each group, the inventors had to go down to 3 vs 3 (3 samples per group, coming from 3 different patients) to get statistically significant genes (18 DEGs, showing no significant GO enrichment). Similarly, random allocation of the control samples (including external controls, balanced across groups) yielded very few DEGs (maximum 17) and no significant GO enrichment.

These results suggest that the primary source of "spurious" differential expression is genetic variation between individuals, which only gets mitigated using lines derived from several patients.

Finally, it is interesting to note that despite yielding very few DEGs (maximum 78), some of the 6 vs 6 comparisons showed statistically significant enrichment for the GO categories of extracellular matrix organization and extracellular structure organization (FDR 2.5E-7 in the shuffling test, versus 2.3E-10 in the comparison between genotypes), pointing to these genes as particularly varying in expression between lines and/or individuals.

In differentiated cell types, shuffling tests using (3 combinations of) 3vs3 samples yielded either no significant differential expression (NCSC), or very few genes (NPC) that displayed no significant enrichments, with the exception of the MSC dataset. The union of genes found significant from random combinations of the MSC samples showed several GO enrichments, including (albeit at a lower level) some categories that were found significant between the genetic conditions. However, removal of these genes did not significantly alter the main categories enriched among the DEGs between genetic conditions (Table 2).

mM Tris-HCl, pH 8.1) and TE. Immunocomplexes were eluted in ChIP elution buffer (0.1% SDS, 1% Triton-X100, 2 mM EDTA, 20 mM Tris-HCl pH 8.1, 500 mM NaCl) and the decrosslinking was performed overnight at 65° C. DNA was purified using Qiaquick PCR Columns (Qiagen) according to manufacturer instructions.

DNA libraries were prepared according to Blecher-Gonen et al.[24] and DNA was sequenced on an Illumina HiSeq 2000 platform.

Validation of ChIPseq results has been performed through qPCR analysis using the following oligo pairs: EOMES (F:

TABLE 2

Gene Ontology category enrichments for differentially expressed genes

| category | term | Log10(Fdr) DEGs | Enrichment DEGs | Log10(Fdr) random | Enrichment random | Enrichment over random | Enrichment without random |
|---|---|---|---|---|---|---|---|
| GO:0001974 | blood vessel remodeling | 4.90022987 | 9.57 | 1.59670852 | 6.23 | 1.59 | 5.88 |
| GO:0014706 | striated muscle tissue development | 8.74816715 | 4.22 | 2.74824703 | 3.21 | 1.56 | 3.00 |
| GO:0050877 | neurological system process | 5.02609321 | 2.27 | 2.80372131 | 2.59 | 1.56 | 1.81 |
| GO:0070371 | ERK1 and ERK2 cascade | 5.13988542 | 5.04 | 1.39744502 | 3.19 | 1.55 | 4.02 |
| GO:0001655 | urogenital system development | 9.4144022 | 4.70 | 2.43853353 | 3.13 | 1.54 | 3.58 |
| GO:0072001 | renal system development | 9.41840026 | 5.03 | 2.5979742 | 3.35 | 1.52 | 3.93 |
| GO:0030510 | regulation of BMP signaling pathway | 4.4263336 | 6.70 | 1.54487389 | 4.71 | 1.42 | 3.94 |
| GO:0048514 | blood vessel morphogenesis | 7.50827453 | 3.46 | 3.37609005 | 3.09 | 1.34 | 2.32 |
| GO:0051216 | cartilage development | 5.47172473 | 4.74 | 1.94938905 | 3.44 | 1.30 | 3.18 | cDNA Preparation and qPCR

Retrotranscribed cDNAs have been obtained from 1 µg of total DNA-depleted RNA using the superscript VILO retrotranscription kit from Life Technologies according to manufacturer instructions.

For real time q-PCR analysis a total amount of cDNA corresponding to 10-50 ng of starting RNA has been used for each reaction. FAST SYBR green master mix from Life Technologies and 10 µM primers pair have been used. The qPCR reactions have been performed on an Applied Biosystems® 7500 Real-Time PCR machine following the standard amplification protocol.

The pair oligos used for qPCR were: GAPDH (F: GCACCGTCAAGGCTGAGAAC (SEQ ID No. 1), R: AGGGATCTCGCTCCTGGAA (SEQ ID No. 2)), BEND4 (F: GGAAAAGGAAAAGGTCAGTGC (SEQ ID No. 3), R: GTITATCTGCTCTTCCGAGGG (SEQ ID No. 4)) and GTF2I (F: GATCTTGCAACCCTGAAATGG (SEQ ID No. 5), R: CACCTGGAGATAGTATITGACCTG (SEQ ID No. 6)).

Chromatin Immunoprecipitation Coupled with Sequencing (ChIPseq)

$10^8$ iPSCs were used for each immunoprecipitation. Cells were detached using accutase, resuspended in PBS containing 1% formaldehyde for fixation and quenched with 125 mM glycine. Cells were lysed using ChIP lysis buffer (1% SDS, 10 mM EDTA, 50 mM Tris-HCl, pH 8.1) and sonicated using the Covaris Sonicator to generate 250 bp DNA fragments. Soluble chromatin was diluted 10 times in ChIP dilution buffer (0.01% SDS, 1.1% Triton-X100, 1.2 mM EDTA, 16.7 mM Tris-HCl pH 8.1, 167 mM NaCl). Chromatin was incubated overnight at 4° C. with the antibody and recovered the day after using Dynabeads Protein G (Life Technologies). Beads were washed sequentially with Low Salt Wash Buffer (0.1% SDS, 1% Triton X-100, 2 mM EDTA, 20 mM Tris-HCl, pH 8.1, 150 mM NaCl), High Salt Wash Buffer (0.1% SDS, 1% Triton X-100, 2 mM EDTA, 20 mM Tris-HCl, pH 8.1, 500 mM NaCl), LiC Wash Buffer (0.25M LiC, 1% NP40, 1% deoxycholate, 1 mM EDTA, 10

GCTGCCATCTTCCTCTGGTAA (SEQ ID No. 7), R: GCTGCCATCTCCTCTGGTAA (SEQ ID No. 8)), SNAP25 (F: CCTCCTGCATAGCTTCAACAAA (SEQ ID No. 9), R: GGTCAGAGGGCAACACAGA (SEQ ID No. 10), DTX3L (F: CACCAGCCCTTGACATCAG (SEQ ID No. 11), R: TCCCTCCAACTCTACCCTAG (SEQ ID No. 12)), HDAC1 (F: TGATGTGGAGAGTTGAGTGG (SEQ ID No. 13), R: GAAAAGATGAGGAAGGGACGG (SEQ ID No. 14)), SEMA4B (F: ATGITAAGGGAGCAGTGAGC (SEQ ID No. 15), R: ATGGTCAGCTCTCAAGAATGG (SEQ ID No. 16)), CRB2 (F: GAACCCAGATCTCTTACGCTG (SEQ ID No. 17), R: CATCTTTAATCCCCTGCCTCTC (SEQ ID No. 18)), MYO1B (F: GGAAACCAGATTAGAGACGGG (SEQ ID No. 19), R: GTTTGTAGTTACCTCTCCAGCG (SEQ ID No. 20)), MFAP2 (F: GAAATCAAGCCTCCCAAAGTG (SEQ ID No. 21), R: TGGAGAGGCAGAAGGAAAAC (SEQ ID No. 22)), ADAM19 (F: AAGCCTTCTCCGGTCATAATG (SEQ ID No. 23), R: TGATGTCCGTGTTCTCAGG (SEQ ID No. 24)), S1PR5 (F: CCTGTGAACTGAGGTTCCTG (SEQ ID No. 25), R: CCACTGAAGACTCCTGCTAAG (SEQ ID No. 26)), JKAMP (F: ACAAGCCCGAAGTCCAAAG (SEQ ID No. 27), R: TCCTGTTCCTGCACAACG (SEQ ID No. 28)), PTPN5 (F: CCTCAACCAGAAACAAGCAG (SEQ ID No. 29), R: CCACCGACCCTTTAGCTTTAG (SEQ ID No. 30)), TMEM20 (F: GCTCCTGTAATTAGTGTCGGG (SEQ ID No. 31), R: GGGATCACTTTCAGGGTCAG (SEQ ID No. 32)).

ChIPseq Analysis

Reads were trimmed for adapter contamination using Scythe 0.981 with a minimum match of 3 before being aligned to the HG19 genome using BowTie 1.0, allowing 2 mismatches and discarding multiply aligning reads. Peaks were called using Macs 2.0.9 with default settings and ignoring duplicated reads. For GTF2I ChIPseq, given the variability between samples, the inventors used two complementary approaches to identify GTF2I binding sites. The inventors considered peaks (independently of FDR) that overlapped between all control and 7dupASDsamples (2079 peaks; 436 target genes) as "conserved peaks", from which the inventors inferred the core GTF2I targets genes. In addition, the inventors called peaks on the pooled reads from all samples (against the pooled inputs) to identify a broader set of putative binding sites, considering only regions with a fold enrichment over input of at least 5 and FDR <0.001 (10691 peaks; 1554 target genes). In all cases, target genes were identified as genes with a peak in a −2.5 /+1 kb around their TSS.

Bivalent domains were defined as regions having H3K4me3 and H3K27me3 peaks within 1 kb of each other in ENCODE's data from the H9 human embryonic stem cell (hESC) line. To assess the quality of the LSD1 ChIPseq, the inventors compared it to ENCODE's ChIPseq for H3K4me2 in H1 hESC line. As expected, 95% of the LSD1 peaks defined by the inventors overlap with a H3K4me2 peak.

Finally, associations between TSS and distal enhancers were inferred from strong correlation, across ENCODE datasets, between the enhancer chromatin signature and expression at the putative target TSS; more specifically, the inventors considered only associations with a FDR<0.001 and a minimum Pearson correlation of 0.5 with H3K27ac, H3K4me1, and −0.5 with DNA methylation, for a total of 5996 enhancer-TSS associations.

Immunoprecipitation and MS Analysis of the GTF2I Complex

About 25-35 millions of cells were harvested and lysed in low stringency lysis buffer (50 mMTris-HCl, pH 7.5, 120 mMNaCl, 0.5 mM EDTA, 0.5% Nonidet P-40) and sonicated using a Branson 250 digital sonifier.

3 mg of protein extract are used for the immunoprecipitation with 10 μg of GTF2I antibody (Bethyl) and with unspecific IgG immunoglobulin O.N rotating at 4° C. The day after, 50 μL of NovexDynabeads Protein G (Life Technologies) are added to each sample and incubated rotating for 2 hours at 4° C. After three washing steps using the washing buffer (50 mMTris-HCl, pH 8, 150 mMNaCl, 0,1% Triton, 5% glycerol) the beads are treated with one volume of 4× Novex LDS sample buffer (50 mM DT) (Life Technologies) and the same volume of sample is loaded on a precast 12%-4% Novex gel (Life Technologies) for SDS-PAGE. Gels were stained using Colloidal Blue Coomassie (Fermentas). 7 discrete bands were cut and analyzed via liquid chromatography-tandem MS.

Liquid Chromatography-Tandem MS (LC-MS/MS) Analysis

Bands of interest were cut from gels and trypsinized as previously described by Shevchencko et al[25]. Peptides were desalted and concentrated on a homemade stage Tip[26] dried in a Speed-Vac and resuspended in 10 μL of 0.1% formic acid. LC-ESI-MS/MS of 5 μL of each sample was performed on a Fourier transformed-LTQ mass spectrometer (FT-LTQ, Thermo Electron, San Jose, Calif.). Peptides separation was achieved on a linear gradient from 100% solvent A (5% ACN, 0.1% formic acid) to 20% solvent B (acetonitrile, 0.1% formic acid) over 30 min and from 20% to 80% solvent B in 20 min at a constant flow rate of 0.3 μL/min on Agilent chromatographic separation system 1100 (Agilent Technologies, Waldbronn, Germany) where the LC system was connected to a 15 cm fused-silica emitter of 75 μm inner diameter (New Objective, Inc. Woburn, Mass. USA), packed in-house with ReproSil-Pur C18-AQ 3 μm beads (Dr. MaischGmbh, Ammerbuch, Germany) using a high-pressure bomb loader (Proxeon, Odense, Denmark).

Survey MS scans were acquired in the FT from m/z 350-1650 with 100 000 resolution. The five most intense doubly and triply charged ions were automatically selected for fragmentation.

Target ions already selected for the MS/MS were dynamically excluded for 60 s.

Data Processing and Analysis

DATABASE SEARCHING: Raw MS files were converted into peaklist (.msm files) via Raw2msm ver 1.10_2007.06.14. All MS/MS samples were analyzed using Mascot (Matrix Science, London, UK; version 2.3.02) set up with the following parameters: Database UniProt_CP_Human_20130724 database (unknown version, 88378 entries), Taxonomy Homo sapiens, enzyme Trypsin, Max missing cleavage 2, fixed modification carbamidomethyl (C), variable modification oxidation (M), acetyl (protein N-terminus) peptide tolerance 10 ppm, MS/MS tolerance 0.5 Da.

CRITERIA FOR PROTEIN IDENTIFICATION: Scaffold (version Scaffold_4.3.4, Proteome Software Inc., Portland, Oreg.) was used to validate MS/MS based peptide and protein identifications. Peptide identifications were accepted if they could be established as greater than 95.0% probability by the Peptide Prophet algorithm[27] with Scaffold delta-mass correction. Protein identifications were accepted if they could be established as greater than 99.0% probability and contained at least 2 identified peptides. Protein probabilities were assigned by the Protein Prophet algorithm[28]. Proteins that contained similar peptides and could not be differentiated based on MS/MS analysis alone were grouped to satisfy the principles of parsimony. Proteins sharing significant peptide evidence were grouped into clusters.

Lentivirus Production

GTF2I knock-down were performed using validated pLKO.1 TRC vector (TRCN0000019315 referred as sh2, TRCN0000364552 referred as sh52 and TRCN0000369208 referred as sh08). A previously described pLKO.1 TRC containing a scrambled short hairpin was used as a negative control[29]. Viral particles were produced using psPAX2 and pMD2.G packaging vectors in 293T cells. Viral particles were harvested at 24 and 36 hours post-transfection and concentrated 250× by ultracentrifugation at 24000 g for 2 hours at 16° C. iPSC lines were infected with different amounts of viral particles, and the amount that gave rise to 50% of survival upon 1 μg/mL puromycin treatment for 72 hours was selected for following experiments.

Infected cells were kept in puromycin-containing mTeSR for the whole duration of the experiments.

Differentiation

Differentiation into the dorsal telencephalic lineage was accomplished by dual Smad inhibition in the presence of SB431542 (Tocris) and Noggin (R&D)[30,31]. Differentiation of NCSC and MSC was performed as previously described[32], through the activation of Wnt signalling and Smad pathway blockade by administering the small molecules GSK3i (Calbiochem) and SB431542 (Tocris).

Embryoid Bodies (EBs) Production and LSD1 Inhibitors Treatments.

In a differentiation experiment about 1.5×10$^4$ cells/well (CTR1R-C3) have been plated on a 96 wells conic plate in mTeSR medium containing 10 mM of a LSD1 inhibitor: N-[4-[trans-2-aminocyclopropyl]phenyl]-3-(2-oxooxazolidin-3-yl)benzamide hydrochloride

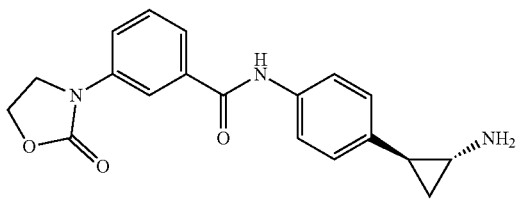 [SMILES: N[C@@H]1C[C@H]1c1ccc(NC(=O)c2cccc(N3CCOC3=O)c2)cc1]

or Example 5 as disclosed in WO2013057322: (trans)-N1-((1R,2S)-2-phenylcyclopropyl)cyclohexane-1,4-diamine hydrochloride 96 well plates were centrifuged at 850 g for 10 minutes at room temperature and the forming EBs have been incubated at 37 degree for 24 hours. 10 uM RA has been added at day 0 or at day 4. At day 1 EBs have been plated on a low attachment dish and media was replaced with KO-DMEM (+P/S+Glut)(EB media) 20% FBS containing. Media, RA, inhibitors and vehicle have been changed every other day for the following 6 days. Next, RNA extraction and cDNA preparation has been performed as described above.

LSD1 inhibitor has been also tested in non-differentiating condition according to the following experimental procedure: about $2.5 \times 10^5$ cells were seeded at day 0 in feeder-free condition on a 6 cm (diameter) plate coated with diluted human-qualified Matrigel (BD Biosciences) and in mTeSR-1 (StemCell Technologies) medium supplemented with 5 μM Y-27632 (Sigma). mTeSR-1 was replaced at day 1 and day 2. At day 3 medium was replaced with mTeSR-1 containing 10 mM of a LSD1 inhibitor N-[4-[trans-2-aminocyclopropyl]phenyl]-3-(2-oxooxazolidin-3-yl)benzamide hydrochloride and incubated at 37 degree for 24 hours. Next, cells were first dissociated by a 3 minutes treatment with Accutase (Sigma) at 37° C. and then harvested for RNA extraction, cDNA and library preparation as described above.

Flow Cytometry $1 \times 10^6$ cells were fixed in 4% PFA and subsequently blocked in 10% BSA. Cells were incubated for one hour with primary conjugated antibody resuspended in 1-2% BSA. The primary conjugated antibody used were CD57-FITC (HNK1, BD), CD271-647 (NGFR, BD), CD44-APC (EBIOS) and CD73-PE (BD). Analysis were performed on FACSCalibur (BD Biosciences) and data were analyzed with FCS express software (Tree Star inc.).

CGH Array

DNA was isolated from parental fibroblast and iPSC using Qiagen kit as described above. DNA concentration and purity were determinate with a ND-1000 spectrophotometer (NanoDrop Technologies, Berlin, Germany) while whole-genome copy number variations (CNVs) analysis was carried out using the CytoScan HD array platform (Affymetrix, Santa Clara, Calif.). The CytoScan HD assay was performed according to the manufacturer protocol, starting with 250 ng of DNA. Briefly, total genomic DNA was digested with a restriction enzyme (NspI), ligated to an appropriate adapter for the enzyme and subjected to PCR amplification using a single primer. After digestion with DNase I, the PCR products were labeled with a biotinylated nucleotide analogue, using terminal deoxynucleotidyl transferase (TdT) and hybridized to the microarray. Hybridization was carried out in the Hybridization Oven 645 while subsequent washing and staining were performed using the Fluidics Station 450.

CGH Array Analysis

Each array was then scanned with the Scanner 3000 7G and both quality control step and copy number analysis were performed using the Chromosome Analysis Suite Software version 2.0: i) the raw data file (.CEL) was normalized using the default options; ii) an unpaired analysis was performed using as baseline 270 HapMap samples in order to obtain Copy numbers value from .CEL files while the amplified and/or deleted regions were detected using a standard Hidden Markov Model (HMM) method.

Microarray

Microarrayanalysis was performed with the Affy package using Marc Carlson's Hugene 2.1st RefSeq annotation file, version 18. Background normalization was performed using the RMA method, whereas between-sample normalization was performed using the quantile normalization method. Quantification of expression was obtained using perfectly matching probes only with median polish summarization, averaging probesets to obtain gene-level expression. Probesets not assigned to known genes or having $\log_2$ fold changes<0.5 were discarded and differential expression was assessed using a 2-tailed t-test. For the purpose of enrichment analyses, DEGs with a FDR<0.2 were considered.

Gene Ontology Enrichment Analysis

For RNAseq data, enrichment analysis was performed using the R package GOseq in order to correct for transcript length bias considering only categories with at least 10 annotated genes and discarding categories that had less than 8 significant genes. For genes measured by other methods, the enrichment analysis was performed with the package TopGO using the classic algorithm and Fisher's test with the same cutoffs described above. In order to create enrichment treemaps, parent categories that had enriched children were first removed and then maps were created with the package Treemap, using as colors the combination of non-overlapping parent categories accounting for the largest proportion of plotted categories. All reported FDR values were calculated using the Benjamini-Hochberg method.

NGN2 Clonal Line Establishment and Characterization

1) Prepare lentiviral particles from UbC-rtTA and FUW-TetO-NGN2-EGFP-Puro or FUW-TetO-NGN2-Puro as in Pang et al.[33] and concentrate by ultracentrifugation, 2) Plate $3 \times 10^6$ iPSCs per well in a 24-well plate in mTeSR medium, 1 day before the infection and replace exhausted medium with fresh mTeSR and infect cells by adding from 0.5 to 1.5 ul of UbC-rtTA lentiviral concentrate and the same amount of FUW-TetO-NGN2-EGP-Puro/FUW-TetO-NGN2-Puro lentiviral concentrate to each well, 3) Split confluent, infected and uninduced iPSCs from a 24-well plate well to a 12-well plate well 1:1, 4) Split cells from a 12-well plate wells to a 6-well plate well 1:1, 5) Split cells from a 6-well plate to 3 6-cm dish 1:3, 6) upon daily medium change, exhausted medium is not discarded but is kept at 4° C. It is then filtered and mixed 1:1 with fresh medium, making up the "recovery medium". This medium is necessary to sustain single cell survival after sorting, 7) upon reaching confluence in 6-cm dishes, 1 dish is frozen as "unsorted bulk population". The other 2 dishes are split using Accutase and resuspending in 800 ul PBS with 1% Pen-Strep per dish, 8) Cells in PBS are sorted as DAPI-negative single cells, each cell in a 96-well plate well and containing 150 ul of "recovery medium" supplemented with 5 uM Rock Inhibitor, using a BD FACSAria II. DAPI-negative cells are alive; the recovery medium with rock inhibitor favors survival of single iPSCs, 9) Cells grow in the incubator for an average of 10-12 days. Medium is changed by replacing 50% with fresh medium and only after 5 days (changing it before can damage small clusters of cells). Medium is then changed daily until colonies emerge. Colonies are scored by eye under a brightfield microscope for a pluripotent morphology of cells and a round shape of the colony, so as to rule out the presence of two cells in the same well. 3 to 5 wells are chosen to establish new lines; each of these wells gives rise to a stable cell lines which arise from a single iPSC with its own transgene integration profile, hence the term "clonal" lines, 10) Colonies occupying approximately half of the surface of the 96 well are split by washing cells with 100 ul PBS and then incubating them with 30 ul of Gentle dissociation reagent for 3 minutes at 37° C. Gentle dissociation reagent is discarded and cells are roughly resuspended in 200 ul mTeSR. Resuspension is very brief so as to avoid breaking colony clumps into single cells. Resuspended clumps are then plated in 48-well plate wells, in a total volume of 300 ul of mTeSR without Rock Inhibitor per well, 11) Cells are subsequently passaged in order to reach 24-, 12- and 6-well plates. This step takes approximately 15 to 20 days as it is important to split cells without diluting them more than 1:5. Each split is done using Gentle dissociation reagent and without Rock inhibitor. Upon passaging cells from the 24-well to 12-well format, cells are split in 2 wells. Two days after splitting, mTeSR is swapped in one of the two wells with Medium 1 with doxycycline, 12) after doxycycline induction of the single 12-well plate well (preferably after 24 hours), GFP-positivity is scored. GFP-positive clones are then further expanded to 6-well and 6 cm dishes starting from the uninduced well, 13) Confluent 6 cm dishes of clonal, GFP-positive cell lines are frozen as stocks and can be readily thawed and expanded at will as iPSC lines.

To induce neuronal differentiation it is sufficient to substitute mTeSR with medium 1+doxycycline as follows:

14) change medium from mTeSR to "Medium 1" as detailed in Zhang et al.[34]:
N2/DMEM/F12/NEAA
Human BDNF (10 mg/l)
human NT-3 (10 mg/l)
mouse laminin (0.2 mg/l)

Doxycycline (2 mg/l) is added preferably on the same day to induce NGN2 and retained in the medium until the end of the experiment, 15) after induction (preferably one day), puromycin is added to the medium (1 mg/l) for 24 hours.

16) after puromycin administration (preferably one day), $6 \times 10^5$ mouse astrocytes are added to each wells, and the medium is changed to "Medium 2" as detailed in Zhang et al. 2013:
Neurobasal supplemented with B27/Glutamax
Human BDNF (10 mg/l)
human NT-3 (10 mg/l)
Ara-C (2 g/l)

17) 8 days after glia addition, FBS (2.5%) is added to the medium to support astrocyte viability.

18) Cells are assayed by immunofluorescence at day in a range between 14 and 31 after induction.

All plates are coated with hESC-qualified matrigel (diluted 1:40 in DMEM/F12/Gln/Pen-Strep) unless otherwise specified. Cells are always incubated at 37° C. with 3% O2 and 5% CO2. Cells are always split using accutase and plated in mTeSR supplemented with 5 uM Rock Inhibitor, which is then removed after the first media change.

The method optionally comprises extraction of genomic DNA from each stable cell line to quantify by digital PCR or TaqMan the exact amount of UbC-rtTA and TetO-NGN2-EGFP-Puro transgene copy numbers.

The present method allows to:
avoid preparing viral particles to infect iPSC lines (an advantage especially if large amounts of iPSCs need to be infected)
avoid infecting iPSCs for every differentiation experiment
conduct large-scale differentiation experiments—iPSCs can grow as such virtually indefinitely and can then be differentiated simultaneously
obtain a homogeneous population as all stable lines come from single integration events
obtain reproducible differentiation experiments as two important sources of variability (virus production and iPSC infection) have been suppressed

EXAMPLES

Example 1: Establishment of a Large Cohort of Transgene-Free Induced Pluripotent Stem Cell Lines from WBS and 7dupASD Patients The inventors selected a highly informative cohort of WBS and 7dupASD patients, whose fibroblast biopsies were deposited in the Genomic and Genetic Disease Biobank (http://www.telethon.it/en/scientists/biobanks) and who were assessed by a multidisciplinary team of specialists for a detailed clinical record (FIG. 1a and Table 3).

TABLE 3

Clinical features of patients.

| Clinical features | | GDB192/ WBS154 AtWBS1 | GDB306/ WBS276 WBS4 | GDB316/ WBS301 WBS2 | GDB361/ WBS309 WBS3 | GDB339/ WBS302 WBS1 | GDB CF 7dupASD1 | GDB242/ WBS202 7dupASD2 |
|---|---|---|---|---|---|---|---|---|
| Intellectual disability | | Moderate | Moderate | Moderate | Moderate | Moderate | Moderate | Moderate |
| Cardiovascular | Supravalvular aortic stenosis | − | + | − | − | + | NA | NA |
| | Peripheral pulmonary stenosis | − | − | − | + | − | NA | NA |
| | Valvular pulmonic stenosis | − | + | − | − | − | NA | NA |
| | Hypertension | − | − | NA | − | + | NA | NA |
| | Others | − | − | − | left ventricular hypertrophy: interatrial septal defect | − | NA | NA |

TABLE 3-continued

Clinical features of patients.

| Clinical features | | GDB192/ WBS154 AtWBS1 | GDB306/ WBS276 WBS4 | GDB316/ WBS301 WBS2 | GDB361/ WBS309 WBS3 | GDB339/ WBS302 WBS1 | GDB CF 7dupASD1 | GDB242/ WBS202 7dupASD2 |
|---|---|---|---|---|---|---|---|---|
| Craniofacial | Wide mouth | + | − | + | − | + | NA | NA |
| | Prominent ear lobes | − | − | − | + | + | NA | + |
| | Dolicocephaly | − | + | + | − | − | NA | NA |
| | Broad forehead | − | + | + | − | + | − | NA |
| | High narrow forehead | − | − | − | − | − | + | NA |
| | Microcephaly | − | + | + | + | + | − | NA |
| | Macrocephaly | − | − | − | − | − | + | NA |
| | Bitemporal narrowing | + | + | + | + | + | NA | NA |
| | Periorbital fullness | + | + | + | + | + | NA | NA |
| | Epicanthal folds | − | − | + | + | + | NA | NA |
| | Long eyelashes | NA | NA | NA | NA | NA | + | NA |
| | Stellate Irides | + | + | + | + | + | NA | NA |
| | Malar flattening | + | + | + | − | + | NA | NA |
| | High broad nose | − | − | − | − | − | + | NA |
| | Short upturned nose | − | + | + | + | + | − | NA |
| | Bulbous nasal tip | + | − | + | + | + | NA | NA |
| | Bridge nose flattened | − | − | + | + | + | NA | NA |
| | Long philtrum | + | + | + | + | + | − | − |
| | Short philtrum | − | − | − | − | − | + | + |
| | Full lips | + | + | + | − | + | NA | NA |
| | Full cheeks | + | + | + | − | + | NA | NA |
| | High arched palate | − | − | − | − | − | + | NA |
| | Dental abnormalities/ malocclusion | − | + | + | NA | + | + | NA |
| | Small or unusually shaped primary teeth | − | + | NA | NA | + | NA | NA |
| | Hypodontia | − | NA | NA | NA | + | NA | NA |
| | Small mandible | NA | NA | NA | NA | NA | + | NA |
| | Retrognathia | NA | NA | NA | NA | NA | + | NA |
| Endocrine | subclinical hypothyroidism | − | + | + | NA | + | NA | NA |
| | Precocious puberty | − | NA | NA | NA | − | NA | NA |
| | Hypercalcemia | − | + | − | − | + | NA | NA |
| | Glucose Intolerance or diabetes mellitus | − | − | NA | NA | − | NA | NA |
| Gastrointestinal | Feeding difficulties | − | + | − | + | + | NA | NA |
| | Abnormal weight gain | − | + | − | − | + | NA | NA |
| | Celiac disease | − | − | − | NA | NA | NA | NA |
| | Constipation | + | + | − | − | − | NA | NA |
| | Gastroesophageal reflux | − | − | − | − | − | NA | NA |
| | Abdominal pain (unclear cause) | − | NA | − | NA | NA | NA | NA |
| | Rectal prolapse | − | NA | − | NA | NA | NA | NA |
| | Diverticular disease | − | − | − | NA | − | NA | NA |
| Genitourinary | Congenital anomalies | − | + | − | + | − | NA | NA |
| | Enuresis | − | − | − | + | + | NA | NA |
| | Nephrocalcinosis | − | − | − | − | − | NA | NA |
| Ocular | Strabismus | + | − | + | + | + | NA | NA |
| | Hypermetropia | − | + | − | NA | − | NA | NA |
| | Narrowing of lacrimal duct | − | − | − | + | − | NA | NA |
| Muscoloskeletal | Kyphosis | + | − | − | − | − | NA | NA |
| | Lordosis | − | − | − | − | − | NA | NA |
| | Scollosis | + | − | − | − | NA | NA | NA |
| | Joint laxity | − | + | − | + | + | NA | NA |
| | Radiouinar synostosis | − | − | + | − | − | NA | NA |
| | Umbilical hernia | − | − | − | − | − | NA | NA |
| Neurological and neuropsychatric features (including ASD hallmarks) | Hypotonia | − | + | + | + | + | + | + |
| | Hyperrelexia | − | − | − | NA | − | NA | NA |
| | Cerebellar findings | − | − | − | − | − | NA | NA |
| | Type 1 Chlari malformation | − | − | − | − | − | NA | NA |
| | Hoarse voice | − | + | + | + | + | NA | NA |
| | Hyperacusis | + | + | + | NA | + | NA | − |
| | Sensorineural hearing loss | + (mild, right ear) | − | + | NA | − | NA | − |
| | Epilepsy | − | − | − | − | − | NA | + |
| | Sleep dysregulation | − | − | − | NA | NA | NA | − |
| | Speech impairment | − | − | − | − | − | + | + |
| | Social impairment | − | − | − | − | − | + | − |
| | Stereotypies | NA | NA | NA | NA | NA | + | − |
| MRI anomalies | Cortical thickening | NA | NA | NA | NA | NA | + | + |
| | Ventricular dilatation | NA | NA | NA | NA | NA | NA | + |

TABLE 3-continued

Clinical features of patients.

| Clinical features | | GDB192/<br>WBS154<br>AtWBS1 | GDB306/<br>WBS276<br>WBS4 | GDB316/<br>WBS301<br>WBS2 | GDB361/<br>WBS309<br>WBS3 | GDB339/<br>WBS302<br>WBS1 | GDB CF<br>7dupASD1 | GDB242/<br>WBS202<br>7dupASD2 |
|---|---|---|---|---|---|---|---|---|
| | Simplified gyral pattern | NA | NA | NA | NA | NA | + | NA |
| | Increased intracranial volume | NA | NA | NA | NA | NA | NA | + |
| | Decreased amygdala/intracranial volume ratio | NA | NA | NA | NA | NA | NA | + |
| | No activation of emotion-processing areas (fMRI) | NA | NA | NA | NA | NA | NA | + |
| Other | Recurrent otitis media | – | – | – | – | – | NA | NA |
| | Short stature | – | + | – | + | – | NA | NA |
| | Inguinal hernias | – | – | – | – | – | NA | NA |
| Reference | | Fusco et al. EJHG 2014 | | | | | Torniero el al. EJHG 2007 | Prontera et al. JADD 2014 |

NA, data not available.
"+" stands for present; stands for not present; "–" stands for not present.
* bilateral cryptorchidism, penile hypospadia This cohort includes: i) four patients carrying the typical WBS deletion; ii) one patient carrying an atypical WBS deletion that spares several genes including BAZ1B, who exhibits milder craniofacial dysmorphisms[35] and lack cardiovascular abnormalities, supporting a role for BAZ1B in neural crest-derived lineages[36]; iii) two patients carrying the typical duplication of the 7q11.23 interval associated to language impairment, autism spectrum disorder and craniofacial dysmorphisms[37]; and iv) one unaffected relative of a typical WBS patient, chosen as genetically half-matched control (three iPSC lines from two additional unrelated individuals were included as additional controls, FIG. 1a). All patients were diagnosed at the molecular level by a combination of FISH (Fluorescent In Situ Hybridization), MLPA (Multiplex Ligation-dependent Probe Amplification), aCGH (array Comparative Genome Hybridization) and qPCR (quantitative real-time Polymerase Chain Reaction, FIG. 1b).

The inventors succeeded in reprogramming skin fibroblasts from each patient/control into iPSC by daily transfection of synthetic mRNAs encoding the five pluripotency factors OCT4 (also known as POU5F1), SOX2, KLF4, LIN28 and c-MYC[23,38] FIG. 12a-b), indicating that 7q11.23 hemideletion/duplication does not prevent the re-establishment of pluripotency. Besides a higher efficiency in terms of number of reprogrammed colonies and kinetics, this integration-free approach avoids the residual permanence of reprogramming transgenes and its detrimental impact in terms of inter-clones heterogeneity, variability in differentiation proficiency, insertional mutagenesis and reprogramming factors-induced DNA damage[38,39]. The inventors characterized 3 independent iPSC lines from each patient or unaffected relative, along with 2 independent iPSC lines from the unrelated control individual, and one additional iPSC line previously reprogrammed by a conditional lentiviral vector following Cre-mediated excision of the single copy integrant amounting to a total cohort of 27 independent iPSC lines (FIG. 1a). iPSC lines exhibited typical morphology, expressed the full range of pluripotency markers including ALP (alkaline phosphatase), OCT4, NANOG, Tra-1-60, SOX2 and SSEA-4, (FIG. 12c-d) and contributed to the three embryonic germ layers upon teratoma differentiation in vivo (FIG. 12c). iPSC lines were also assessed for genomic integrity by comparison to the respective parental fibroblasts through high density CytoScan Arrays. As shown in Table 4, virtually all iPSC lines carried copy number variants. Several of these were acquired de novo during the reprogramming process, as an inherent aspect of the attending laboratory manipulations (such as the use of reprogramming factors and the trigger of sustained proliferation), and as such distinguish them univocally from the parental somatic cells originally sourced from the research participants. Others instead pre-existed already in parental fibroblasts, consistent with recent evidence of pronounced CNV mosaicism in human skin from which 'de novo' iPSC-specific CNV emerge and become detectable as a result of clonal expansion[40]. In summary, the iPSC from this cohort are clearly distinct both from: i) any other iPSC reported thus far, due to the unique genetic make up that includes reprogramming-induced specific CNVs, and to the method employed for reprogramming; ii) any somatic cell originally sourced from the research participants, due to the specific CNVs that were introduced during reprogramming.

TABLE 4

Copy-number variations (CNVs) identified through aCGH

| iPSC line | Total CNVs | iPSC-specific CNVs (absent in fibroblasts) |
|---|---|---|
| 7dupASD1-C1 | 5 | chr6: 254253-381137 (–), chr20: 29989418-30665270 (+) |
| 7dupASD1-C2 | 4 | chr6: 254175-381137 (–) |
| 7dupASD1-C3 | 5 | chr6: 254253-381137 (–), chr6: 102252826-102423940 (–) |
| 7dupASD2- C1 | 20 | chr4: 93058279-94067253 (+), chr5: 147088797-147206977 (+), chr6: 267501-381118 (–), chr6: 94409405-94683997 (+), chr6: 73864358- |

TABLE 4-continued

Copy-number variations (CNVs) identified through aCGH

| iPSC line | Total CNVs | iPSC-specific CNVs (absent in fibroblasts) |
|---|---|---|
| | | 74468940 (+), chr4: 5525692-5746086 (−), chr7: 121960918-122229095 (+), chr7: 83674322-83967930 (+), chr7: 83043316-83370032 (+), chr11: 125569543-126231307 (+), chr12: 79761650-79874892 (+), chr14: 57301966-57489712 (+), chr14: 37095616-37311723 (+), chr14: 21770209-22001589 (+), chr20: 29652121-32332903 (+) |
| 7dupASD2-C2 | 5 | none significant |
| 7dupASD2-C3 | 5 | none significant |
| 7dupASD2-C5 | 6 | chr10: 53793333-53986201 (+) |
| AtWBS1-C1 | 17 | chr5: 147160867-147211743 (+), chr7: 122088955-122165269 (+), chr10: 53775828-53856760 (+), chr19: 53893835-53991962 (+), chr5: 180378753-180485857 (+), chr19: 54196897-54306189 (+), chr6: 94441864-94581718 (+), chr7: 82958543-83174511 (+), chr7: 121529836-121803926 (+), chr20: 60684625-60960515 (+), chr1: 144081221-144884970 (+), chr1: 147933972-149758028 (+) |
| AtWBS1-C2 | 7 | chr5: 174172854-174216370 (−), chr1: 64098064-64177299 (+), chr5: 180374897-180485857 (+) |
| AtWBS1-C3 | 17 | chr4: 55103916-55159462 (+), chr7: 122088594-122160742 (+), chr7: 121980929-122064412 (+), chr5: 180374483-180485857 (+), chr6: 94445905-94596361 (+), chr7: 83018833-83184441 (+), chr1: 82209385-82379820 (+), chr7: 83435331-83638075 (+), chr19: 54165173-54454992 (+), chr1: 144086896-144884321 (+), chr1: 147831169-149660970 (+) |
| CTL1R-C1 | 5 | chr7: 121960918-122027625 (+), chr7: 122090358-122160742 (+) |
| CTL1R-C2 | 7 | chr8: 1825200-1941407 (+), chr10: 24028502-24165815 (−), chrX: 119999582-120139697 (−), chr6: 33227014-33409781 (+) |
| CTL1R-C3 | 9 | chr5: 147188740-147291626 (+), chr14: 106667034-106931309 (+), chr5: 65445341-66268829 (+), chr1: 237971511-238837154 (+), chr8: 112519123-113612654 (+), chr6: 109789585-111271950 (+) |
| WBS1-C2 | 7 | chr5: 147185452-147246473 (+), chr8: 68346377-68541850 (+), chr7: 137529539-138040330 (+) |
| WBS1-C3 | 7 | chr7: 122017176-122129600 (+), chr3: 77123372-77418651 (+), chr4: 92974531-93517978 (+) |
| WBS2-C1 | 8 | chr4: 93151709-93505123 (+), chr7: 122017096-122293350 (+) |
| WBS2-C2 | 10 | chr4: 93151709-93573786 (+), chr6: 94441864-94817554 (+), chr7: 83018833-83214294 (+), chr7: 121960918-122205630 (+) |
| WBS2-C3 | 5 | chr4: 93099134-94304185 (+), chr7: 121776521-122291289 (+) |
| WBS3-C1 | 4 | none significant |
| WBS3-C2 | 12 | chr6: 294712-381137 (−), chr7: 121695010-121818973 (+), chr20: 15053066-15192669 (−), chr7: 83435331-83607471 (+), chr7: 121962453-122191669 (+), chr7: 82837315-83213300 (+), chr6: 94378742-94822428 (+), chr4: 92992264-93622621 (+) |
| WBS3-C3 | 8 | chr6: 330691-381137 (−), chr7: 83063087-83168747 (+), chr7: 121960918-122148266 (+), chr6: 94478593-94824268 (+) |
| WBS4-C1 | 10 | chr10: 47055847-47149411 (−), chr7: 74507793-74629034 (−), chr12: 124814373-124974860 (−), chr4: 93150773-93389036 (+), chr4: 85917848-86271752 (−) |
| WBS4-C2 | 10 | chr7: 74530357-74621643 (−), chr1: 234083694-234196919 (+), chr7: 110817057-111296229 (−) |
| WBS4-C3 | 11 | chr1: 234083694-234200257 (+), chr7: 121981127-122129600 (+), chr6: 94405746-94592955 (+), chr6: 40846660-41825053 (−) |

Summary of the aCGH data on iPSC lines, indicating the genomic coordinates (in the human reference genome version hg19) of iPSC-specific CNVs. "+" indicates a copy-number gain, while "−" indicates a loss. For example, line 7dupASD1-C1 has lost a copy of the region spanning base pairs 254253 to 381137 of chromosome 6.

Example 2: Expression of 7q11.23 Genes Follows Gene Dosage in the Pluripotent State In order to ascertain whether the pluripotent state represented a meaningful stage at which to probe the effect of 7q11.23 dosage, the inventors first asked whether the mRNA expression of the 7q11.23 genes follows gene dosage. For this the inventors resorted to the high accuracy of Nanostring-based quantitation as well as to RNAseq and found that the expression of all genes of the interval (including those expressed at very low levels) mirrors gene dosage (FIG. 1c and FIG. 13a), thus excluding compensatory effects from the wild type allele. The inventors then confirmed that also at the protein level the expression of both GTF2I and BAZ1B, the genes associated to key traits of WBS and 7DupASD[34,41-45], reflected the symmetrical dosage of the two conditions (FIG. 13b-c-d).

Example 3: 7q11.23 Dosage Imbalance Causes Transcriptional Dysregulation in Disease-Relevant Pathways Already at the Pluripotent State To assess differential expression between genotypes, the inventors profiled by RNAseq the panel of patient- and control-derived iPSC lines, and complemented this dataset also with additional control lines from the literature (hereafter referred to as external controls, see methods), excluding from further analysis the genes that were differentially-expressed between controls from the inventors' cohort and external controls. A pair-wise comparison of the three genotypes identified 757 differentially-expressed genes (DEGs) (FIG. 2a). Strikingly, Gene Ontology (GO) analysis of the union of DEGs revealed significant enrichments for biological processes of obvious relevance for the hallmark phenotypes and target organ systems of the two conditions.

FIG. 2b shows a treemap representation of the most specific enriched biological processes, in which square sizes are proportional to the significance of the enrichment (GO enrichments for each comparison are shown in FIG. 14a-b-c). The top-ranking categories are related to extracellular matrix (EM) organization (FDR~2.3E-15), which appears especially significant in light of the wide range of connective tissue alterations that characterize WBS, and to the nervous system (e.g. neuron differentiation FDR~2.7E-7, neuron projection development FDR~3.6E-6), providing a molecular context for the defining neurodevelopmental features of the two conditions. In addition, further enrichments relate to remarkably specific features of the two diseases. These include:

i) cellular calcium ion homeostasis (FDR~0.0012), a category of potential relevance across disease areas but that acquires particular salience in light of the high prevalence of hypercalcemia in WBS[46] (DEGs in category: ATP1A2, ATP2A2, ATP7B, CACNA1A, CALCR, CAV1, CCDC47, CCKBR, CD40, DIAPH1, EDNRB, EPHX2, GRIK2, GSTO1, GTF2I, HRC, ITPR3, KDR, RYR1, RYR2, SLC30A1, SLC8A3, TACR1, TRDN);

ii) inner ear morphogenesis (FDR~0.0046), consistent with the combination of hyperacusis and sensorineural hearing loss that is virtually always present in WBS[47], as well as with the balance and sensory processing disorders found in ASD[48] (DEGs in category: COL11A1, COL2A1, FZD2, GBX2, MAFB, MYO6, NTN1, SOX9, WNT3A, ZEB1, ZIC1);

iii) a number of categories relevant for the craniofacial phenotype, such as skeletal muscle organ development (FDR~0.0067), migration (FDR~4.2E-8) and neural crest cell differentiation (FDR~0.011) (DEGs in any of the three categories;

iv) categories such as blood vessel development (FDR~0.0068) and cardiovascular system development (FDR~0.0043), that reflect the wide range of cardiovascular problems in WBS;

v) kidney epithelium development (FDR~0.0026), in line with the highly prevalent kidney abnormalities of WBS[49].

Importantly, removal of the external controls did not lead to significant changes in the enrichments the inventors obtained (FIG. 14d), indicating that the cohort of the present invention's in-house reprogrammed lines already sufficed to capture the key features of 7q11.23-dependent transcriptional dysregulation. Furthermore, in order to exclude the possibility that such enrichments could arise by chance, the inventors performed a series of shuffling tests entailing comparisons between randomly assigned groups of samples (see methods). In the rare cases in which these tests yielded any differentially expressed genes, these showed no enrichment with the exception of extracellular matrix structure (see methods and as described above), thus confirming that the enrichments the inventors found are specifically caused by 7q11.23 dosage imbalances.

The inventors found that the majority of DEGs either show a symmetrically opposite pattern in the two conditions or have a fold-change in the same direction over controls, indicating that the symmetrical dosage imbalances mostly affect the same transcriptional programs, either in the same or in symmetrically opposite ways. The inventors thus proceeded to uncover what were the most highly symmetrical genes, taking the DEGs for which the mean expression in control samples was within a 20-80% range between the means of the WBS and 7DupASD (~39% of the DEGs) and that had an absolute Pearson correlation of at least 0.5 with WBS gene dosage. This high-confidence set included 166 symmetrical DEGs (FIG. 15), establishing that, in the pluripotent state, the symmetry in dosage is reflected into at least 22% of transcriptional dysregulation. Notably, this set showed only one significant GO enrichment, namely for the category of synaptic transmission (FDR~0.023; DEGs in category are: ADCY2, CACNA1A, ETV5, GABBR2, GRIN2D, HCN1, ITPR3, KCNK6, KIT, MYO6, NCALD, NPTX1, PCDHB5, PLCB2, RASD2, SLC1A1, SNCAIP, STX1A, STX1B, STXBP1, SYT1). Furthermore, the set of symmetrically dysregulated genes includes genes associated to characterizing phenotypes of the 2 conditions, as in the case of PDLIM1 and MYH14, the former associated to attention-deficit disorder[50], neurite outgrowth[51], cardiovascular defects, and hyperacusis, and the latter involved in hearing impairment[37].

Example 4: GTF2I Dosage Accounts for a Significant Fraction of Transcriptional Dysregulation in the Pluripotent State Convergent evidence from atypical patients and experimental models[13,41,52-54] pointed to general transcription factor GTF2I as a critical gene for the pathogenesis of the cognitive/behavioural deficits of the two conditions. In light of the above findings, the inventors thus asked what quota of 7q11.23 transcriptional dysregulation could be attributed to GTF2I, using lentiviral RNAi to i) revert the GTF2I dosage of 7DupASD to control levels, ii) to model GTF2I haploinsufficiency by knocking-down GTF2I in controls and selecting clones whose residual GTF2I levels were similar to those of WBS lines, iii) to exacerbate the dysregulation of GTFI transcriptional targets that are insensitive to haploinsufficiency by knocking down GTF2I mRNA also in WBS lines (FIG. 2c-d). The inventors selected and profiled by RNAseq two GTF2I-knock down (KD) stable cell lines per genotype and their respective scrambled short hairpin controls. Depending on the approach, the inventors estimate that GTF2I is responsible for 10 to 20% of 7q11.23-dependent transcriptional dysregulation (FIG. 2e). Interestingly, the DEGs imputable to GTF2I show significant enrichments in categories related to most of the disease-relevant spectrum (FIG. 2f). Thus, although previous models have so far emphasized the role of GTF2I in the cognitive and behavioral features of WBS[13], these data indicate for GTF2I a wider role in several disease-relevant pathways already from the onset of development.

Example 5: GTF2I Assembles a Transcriptional Co-Repressor Complex Containing LSD1 and HDAC2

In order to elucidate the mechanism through which GTF2I regulates this significant portion of disease-relevant gene expression, the inventors purified its protein complex and defined its genome-wide occupancy. First, the inventors tested the ability of two GTF2I antibodies to immunoprecipitate GTF2I in its native form (FIG. 16a) and selected the most efficient ones for large-scale IP (immunoprecipitation) on one representative iPSC line for each genotype, followed by Mass Spectrometry (MS) of discrete bands from IP eluates and validation of selected candidates (FIG. 3a-b). Strikingly, the inventors found two transcriptionally repressive chromatin modifiers, the histone demethylase LSD1 (also known as KDM1A) and the histone deacetylase HDAC2 (Q92769), that were sub-stoichiometrically associated to GTF2I. In addition, the inventors identified two transcription factors, ZMYM2 and ZMYM3 (A6NHB5), previously reported as part of LSD1-containing transcriptional complexes (BHC complex)[55-57]. Importantly, the inventors also found the co-repressor RCOR2 (Q8IZ40), recently reported, in place of RCOR1, as the main partner of LSD1 in the pluripotent state[58]. The other proteins identified in the complex are DNMT3B (P11388-4) and FXR1 (P51114).

Example 6: Identification of GTF2I Targets in WBS and 7DupASD Patient-Derived iPSCs The observation that in iPSCs GTF2I associates with transcriptional repressors was unexpected both in light of published reports on its transcriptional effects[59,60] and of inventors' finding that GTF2I-attributable DEGs are evenly distributed among repressed and activated targets. This raises the hypothesis that GTF2I binds directly to only a subset of its imputable targets. Thus, in order to discriminate direct from indirect transcriptional changes, the inventors determined the GTF2I binding profiles by ChIP-seq (Chromatin Immuno-Precipitation coupled with sequencing). The inventors first tested three available antibodies (Cell Signaling, Bethyl and Santa Cruz) on a control iPSC line (FIG. 16b), and selected for further experiments the antibody with the highest signal-to-noise ratio (FIG. 16c) and highest efficiency in immunoprecipitation. The inventors profiled 1-2 iPSC lines from each patient and control, for a total of 12 samples, and identified a total of 1554 genes with a GTF2I binding site in the −2.5 kb/+1 kb region around the transcription start site (TSS). The inventors then concentrated on the peaks that were conserved across all control and 7dupASD samples, and considered the 436 genes with such a high-confidence peak in their promoter as "core GTF2I targets", whose functional annotation is shown in FIG. 3c.

The 436 genes are as follows:
GTF2I Core Targets (Conserved Promoter Peak in all Control Samples):
ABCC3, ACOT12, ACTA2, ACTN3, ADA, ADAM19, ADAMTS10, ADAMTSL5, ADCY3, ADRBK2, AES, AGPAT3, AGXT2L2, AHCY, ALDH18A1, ANO8, APC2, ARAP1, ARF1, ARHGAP40, ARHGEF1, ARHGEF10L, ARHGEF16, ARID3A, ARMC3, ARPC1B, ATE1, ATG16L1, ATG4D, ATP2C2, ATXN10, AVPI1, B3GNT3, B4GALT4, BCL11B, BCL7B, BCL9, BIK, BRF1, BSND, BTBD11, BTBD6, BTBD8, C11orf86, C16orf95, C19orf60, C19orf66, C19orf71, C2orf48, C7orf55, C7orf55-LUC7L2, CACTIN-AS1, CAMK1, CAMK2G, CAND2, CASKIN1, CBFA2T2, CBX3, CCDC34, CCDC71, CCNI2, CCR10, CD209, CD3EAP, CD83, CDC25B, CDH5, CDK9, CEBPG, CELF5, CHST12, CLK3, CNN2, CNTNAP1, COASY, COL16A1, CPA5, CPPED1, CRB2, CREB3L4, CRX, CRYBB1, CRYL1, CSRNP1, CST6, CTDSP1, CYB5B, CYB5R3, DAK, DAPK3, DDB1, DDX17, DEAF1, DEPDC5, DIAPH2, DIRAS1, DOCK6, DPM2, DPP3, DPP4, DPPA2, DRG2, DYRK1A, EARS2, EFHD1, EFNB3, EFR3A, EHD2, EIF4E1B, EIF4G2, ELAVL3, ELL, EMID1, EML2, EPC2, EXOC2, FAM220A, FAM49B, FAM92B, FAS-AS1, FASTKD5, FBLN1, FBLN2, FBN3, FBXO31, FCHO1, FGF22, FHAD1, FOSL2, FOXA3, FSTL5, FUS, FXN, FXYD7, FZD1, FZD2, GADD45B, GALNT10, GALNT11, GAMT, GAREML, GAS2L1, GATSL3, GDPD3, GNA12, GRIP2, GRK6, GRPEL2, GTF2F1, GTPBP3, H6PD, HDAC1, HLA-DPA1, HLCS, HNRNPA2B1, HPS4, ICAM1, IFI30, IQCA1, IQCE, ISOC2, JUNB, JUND, KANK2, KCNK15, KCNS1, KCTD14, KCTD21, KDM4A, KHDRBS3, KIF12, KIF13A, KIF16B, KPTN, KREMEN2, KRTAP10-4, KXD1, L1TD1, LAMC3, LARP1, LDLR, LDLRAP1, LGALS1, LGR6, LINC00620, LINC00862, LINGO1, LMTK3, LOC100128398, LOC100131655, LOC100506082, LOC100506100, LOC100507600, LOC284751, LOC387723, LOC389033, LOXL4, LPAR2, LPIN1, LRRC25, LRRC32, LRRC33, LSR, LUC7L2, MAGI3, MAP1LC3B, MAP4K2, MAPKAP1, MB, MCOLN2, MDS2, MEGF9, MFAP2, MFF, MGAT3, MIAT, MICALL2, MIDN, MIR2861, MIR3188, MIR3190, MIR3191, MIR3529, MIR3960, MIR4281, MIR4497, MIR4632, MIR4736, MKNK2, MMP28, MRPS5, MTFP1, MYO1B, MYOCD, NACC1, NAE1, NAPA-AS1, NCOR2, NDE1, NDUFA3, NEK6, NIPSNAP1, NKD1, NLRX1, NMUR1, NPAS1, NPY4R, NR2F6, NR6A1, NTAN1, NUDT3, NUDT8, NYAP1, OGDHL, OSCAR, PAK4, PAPPA, PASK, PDE4A, PDE8A, PDLIM1, PDLIM7, PEAR1, PEX5, PGPEP1, PHACTR4, PHYH, PIANP, PION, PKN1, PLAUR, PLCD1, PLIN3, PLIN5, PLK5, PLOD1, PNPLA6, POLR3K, PPIA, PPP1R13L, PPP1R16A, PPP1R1A, PPP1R7, PRKCD, PRRT3, PSIP1, PSMG3, PSMG3-AS1, PTGIS, PTPN11, PTPRU, RAB1A, RAB3IL1, RAC1, RAP1GAP, RASGEF1C, RELB, RHPN2, RILPL1, RILPL2, RIN3, RPL18, RPL4, RPS18, RPSAP58, RRM2, SAFB, SAFB2, SCN8A, SCRN1, SEMA4B, SEMA6B, SEPT9, SEPW1, SETD1A, SGSM1, SH2D5, SH3GLB2, SH3PXD2B, SHISA5, SHISA6, SIRPA, SLC12A4, SLC15A3, SLC1A6, SLC29A3, SLC2A1, SLC2A1-AS1, SLC38A10, SLC39A1, SLC39A10, SLC43A1, SLC44A1, SLC52A3, SLC5A5, SLC6A20, SLC6A4, SNORD16, SNORD18A, SNRNP25, SOGA1, SORBS1, SPATA2, SPHK2, SPOCD1, SREBF1, SRPK1, SRPK2, SRRD, SRXN1, SSBP4, ST6GALNAC6, STRBP, STX1B, SWSAP1, SYMPK, SYN1, SYNGR1, SYNJ2, SYT2, TADA1, TAF6L, TAGLN, TBC1D2, TBX6, TBXA2R, TCEA2, TCF3, TCIRG1, TCTN3, TESC, TEX40, TFE3, THUMPD2, TINAGL1, TJP3, TKT, TMC6, TMC7, TMEM120A, TMEM14B, TMEM161A, TMEM194B, TMEM200B, TMEM229B, TMEM80, TNFAIP8L1, TNNT2, TNRC18, TOPORS-AS1, TP53I11, TPM4, TPST2, TRIM26, TRIM59, TRMT1, TRPV4, TSC1, TSPO, TC38, TUB, TVP23A, UBE2Q1, UBFD1, UBOX5, USHBP1, USP35, VAV1, VPS37C, VPS37D, VPS52, VSTM2L, WBSCR27, WDR38, WNT4, WSCD2, XKR7, YIPF1, ZBTB47, ZCCHC14, ZDHHC12, ZDHHC24, ZFAND4, ZMYM6NB, ZNF234, ZNF236, ZNF335, ZNF500, ZNF579, ZNF606, ZNF646, ZNF668, ZNF839, ZNRF4, ZSWIM4, ZWILCH All GTF2I Targets (Significant Promoter Peak in the Merged Analysis):
ABCA7, ABCC3, ABCD4, ABHD3, ABHD8, ACAD10, ACBD4, ACMSD, ACOT12, ACP5, ACTA2, ACTL8, ACTN3, ACVR2B, ADA, ADAM19, ADAM32, ADAMTS10, ADAMTS14, ADAMTSL5, ADAR, ADCY3, ADM5, ADORA2A, ADRBK2, ADSL, AES, AFAP1L2, AFG3L2, AGPAT3, AGT, AGXT2L2, AHCY, AIM1, AIM1L, AIRE, AK1, AK8, AKNA, ALDH18A1, ALDH1B1, ALDH3B1, ALDH4A1, ALG8, ALS2CL, ALX4, ALYREF, AMICA1, AMN, ANAPC1, ANAPC11, ANGPT1, ANKLE2, ANKMY1, ANKRD24, ANKRD9, ANO8, ANO9, AP4S1, APBA3, APC2, APCDD1L, APCDD1L-AS1, APOE, APOO, ARAP1, ARF1, ARHGAP18, ARHGAP22, ARHGAP23, ARHGAP27, ARHGAP40, ARHGEF1, ARHGEF10L, ARHGEF16, ARHGEF19, ARHGEF3, ARID1A, ARID3A, ARID5A, ARL5A, ARL6IP5, ARMC3, ARPC1B, ARPC4, ARPC4-TTLL3, ARRDC3-AS1, ARSI, ASAP3, ASS1, ASTN2, ATAD2, ATCAY, ATE1, ATE1-AS1, ATG16L1, ATG16L2, ATG4D, ATP1A2, ATP2C2, ATP8B3, ATXN10, AVPI1, AVPR1A, B3GALT5, B3GNT3, B3GNT5, B4GALNT3, B4GALT4, B4GALT5, BAIAP3, BAX, BCAS1, BCAT1, BCL11B, BCL2L13, BCL7B, BCL9, BCL9L, BCS1L, BEND4, BFSP1, BIK, BLVRB, BMP7, BNIP3, BPIFB3, BRAP, BRF1, BSND, BSPRY, BST2, BTBD11, BTBD6, BTBD8, BZRAP1, BZRAP1-AS1, C10orf55, C11orf68, C11orf86, C12orf49, C12orf65, C14orf1, C16orf54, C16orf62, C16orf95, C16orf96, C17orf58, C17orf99, C19orf25, C19orf35, C19orf38, C19orf47, C19orf60, C19orf66, C19orf71, C19orf81, C19orf83, C1orf137, C1QC, C1QTNF6, C21orf88, C2orf48, C2orf50, C3orf18, C3orf55, C6orf100, C7orf55, C7orf55-LUC7L2, C7orf61, C9orf40, C9orf9, CABP1, CACNA1F, CACNA1H, CACNB3, CACTIN, CACTIN-AS1, CAGE1, CALCA, CALR, CAMK1, CAMK2G, CAMKK1, CAND2, CAP1, CAPN12, CAPN2, CARD10, CARHSP1, CARNS1, CASC8, CASKIN1, CATIP-AS1, CBFA2T2, CBLN3, CBX1, CBX3, CBX7, CCDC110, CCDC130, CCDC148, CCDC22, CCDC23, CCDC34, CCDC63, CCDC69, CCDC71, CCL2, CCM2L, CCNI2, CCR10, CD19, CD209, CD276, CD3EAP, CD40LG, CD79B, CD83, CD99L2, CDA, CDAN1, CDC25B, CDC42BPG, CDC42EP2, CDC42EP4, CDH5, CDK2AP2, CDK9, CEACAM16, CEBPE, CEBPG, CECR5, CELF5, CEMIP, CENPA, CEP68, CERS4, CFD, CGN, CHADL, CHDH, CHST12, CHST9, CHUK, CILP2, CIZ1, CLASP, CLDN14, CLEC16A, CLEC17A, CLEC2L, CLEC4G, CLEC4GP1, CLIP3, CLK3, CLMP, CLPSL2, CLSTN1, CLU, CLVS1, CMTM3, CNN1, CNN2, CNOT8, CNP, CNPY4, CNTD2, CNTFR, CNTNAP1, COASY, COL16A1, COL9A3, COQ7, COX10, COX10-AS1, COX17, CPA5, CPLX2, CPNE5, CPPED1, CPSF6, CPT1A, CPT1C, CRABP1, CRB2, CREB3L3, CREB3L4, CRLF1, CROCC, CRX, CRYBA2, CRYBA4, CRYBB1, CRYGN, CRYL1, CSF1, CSK, CSRNP1, CST11, CST3, CST6, CSTB, CTD-2270F17.1, CTDSP1, CTF1, CXorf58, CXXC5, CYB5B, CYB5R3, CYGB, CYHR1, CYLD, CYP20A1, CYP26A1, CYP2W1, CYP4F22, DACT3, DACT3-AS1, DAGLB, DAK, DAND5, DAPK3, DCK, DCLK1, DCTN6, DCTPP1, DDB1, DDIAS, DDX17, DDX54, DEAF1, DEGS2, DEPDC5, DFFA, DHRS13, DHRS13, DHX35, DIAPH2, DIRAS1, DLGAP4, DNAAF3, DNAJB8-AS1, DNAJC17, DNMT1, DNMT3B, DOCK11, DOCK6, DOLPP1, DPEP1, DPM2, DPP3, DPP4, DPPA2, DRAP1, DRC1, DRG2, DUS3L, DUSP28, DUSP8, DYRK1A, E4F1, EARS2, ECD, EEF2K, EFCAB6, EFCAB7, EFHD1, EFNA4, EFNB3, EFR3A, EGR4, EHBP1L1, EHD2, EIF2B3, EIF4E1B, EIF4E2, EIF4E3, EIF4G2, ELAVL3, ELF5, ELFN1, ELFN2, ELL, EMID1, EML2, EML3, ENG, EPB41L3, EPC2, EPS15, ERICH2, ERMAP, ERP44, EVA1B, EXOC2, EYA2, F11R, F2R, FAM110A, FAM149A, FAM160B2, FAM166B, FAM167B, FAM174B, FAM178A, FAM179A, FAM188B, FAM193B, FAM199X, FAM220A, FAM222A, FAM222A-AS1, FAM49B, FAM64A, FAM65A, FAM69B, FAM83A-AS1, FAM92A1, FAM92B, FANCA, FAS-AS1, FASTKD5, FBLN1, FBLN2, FBN3, FBXL19, FBXO21, FBXO31, FBXO46, FBXW8, FCER2, FCHO1, FGF22, FGF8, FGFR1, FGFR2, FHAD1, FIBCD1, FKBP11, FLII, FLJ21408, FLJ26850, FLJ33534, FMN1, FOSL2, FOXA3, FOXN1, FRRS1L, FSD1, FSIP1, FSTL5, FURIN, FUS, FUT8, FXN, FXYD5, FXYD7, FZD1, FZD2, GABRP, GABRR3, GADD45B, GALNT10, GALNT1, GAMT, GAPDHS, GAREML, GAS2L1, GAS7, GATA2, GATSL3, GBGT1, GCM2, GDPD3, GDPD5, GEMIN7, GGT1, GHDC, GINS2, GIPR, GKN2, GNA12, GNB5, GOLGA3, GOLGA5, GOLTA, GOT1, GP9, GPAM, GPBP1L1, GPN2, GPR27, GPR64, GPR68, GPX1, GREB1, GRHL3, GRIN3B, GRIP2, GRK5, GRK6, GRPEL2, GSAP, GSC2, GTDC1, GTF2E2, GTF2F1, GTF3C1, GTPBP3, GUCY1B2, GUCY2C, H6PD, HAPLN4, HAUS5, HCK, HDAC1, HDAC11, HEATR5A, HEMK1, HHEX, HIC1, HIF3A, HIRIP3, HLA-DPA1, HLCS, HM13-AS1, HMCN2, HMGN1, HMHA1, HNRNPA2B1, HNRNPM, HPD, HPN-AS1, HPS1, HPS4, HRH2, HS1BP3, HS3ST3A1, HSPB1, HTR6, ICAM1, ICAM3, ID1, IER3IP1, IFI30, IFT122, IFT43, IGSF1, IL12RB1, IL17RA, IL17RB, IL19, ILRL1, IL21R, IL4R, INF2, INHBA, INO80, INO80E, INPP5J, INSR, INSRR, INTS8, INVS, IP09, IP09-AS1, IQCA1, IQCD, IQCE, IQGAP2, IRF2BP1, IRX6, ISM2, ISOC2, ISYNA1, ITGAL, ITGB3BP, JPH3, JUNB, JUND, KANK2, KANK3, KANTR, KAT2B, KAZN, KCMF1, KCND1, KCNH3, KCNIP3, KCNJ12, KCNJ4, KCNK15, KCNK6, KCNMB1, KCNQ4, KCNS1, KCTD14, KCTD2, KCTD21, KCTD21-AS1, KDELR3, KDM4A, KEAP1, KHDRBS3, KIAA0556, KIAA1191, KIAA1279, KIAA1644, KIAA1671, KIAA1755, KIAA1919, KIAA2018, KIF12, KIF13A, KIF16B, KIF3B, KIF6, KLHL17, KLHL21, KLHL35, KLHL4, KPNA1, KPNB1, KPTN, KREMEN1, KREMEN2, KRTAP10-2, KRTAP10-4, KRTAP5-AS1, KXD1, L1TD1, LAMC2, LAMC3, LAMTOR1, LAPTM5, LARP, LDB1, LDHD, LDLR, LDLRAP1, LEFTY2, LGALS1, LGR6, LHPP, LINC00112, LINC00200, LINC00207, LINC00263, LINC00311, LINC00479, LINC00489, LINC00523, LINC00535, LINC00620, LINC00690, LINC00862, LINC00877, LINC00959, LINC01100, LINC01270, LINC01272, LINGO1, LIPC, LITAF, LMNTD2, LMTK3, LOC100128398, LOC100128531, LOC100128568, LOC100129973, LOC100130238, LOC100131655, LOC100288866, LOC100335030, LOC100505622, LOC100505666, LOC100505942, LOC100506082, LOC100506100, LOC100506119, LOC100506700, LOC100506860, LOC100506985, LOC100507501, LOC100507534, LOC100507600, LOC100996351, LOC101926888, LOC101927124, LOC101927272, LOC101927323, LOC101927380, LOC101927954, LOC101928069, LOC101928093, LOC101928107, LOC101928244, LOC101928736, LOC101928737, LOC101929116, LOC101929125, LOC101929384, LOC101929526, LOC101929567, LOC101929657, LOC102503427, LOC102546298, LOC102577424, LOC102723385, LOC102724020, LOC102724827, LOC149684, LOC150381, LOC253044, LOC284751, LOC387723, LOC388282, LOC389033, LOC401177, LOC440028, LOC643770, LOC728743, LOC729966, LOXL4, LPAR2, LPIN1, LPP, LPP-AS2, LPPR2, LRP5, LRRC25, LRRC32, LRRC33, LRRTM3, LSR, LTBP4, LUC7L2, LUZP6, LYPD6B, MAGI1-AS1, MAGI3, MAN2C1, MAP1LC3B, MAP1S, MAP2K3, MAP4K2, MAP7D1, MAPKAP1, MAPRE1, MARK4, MAST1, MATK, MB, MBD4, MCOLN1, MCOLN2, MDS2, MECR, MED12L, MED16, MED17, MED7, MEF2B, MEGF10, MEGF8, MEGF9, MEIS3, MELK, MEOX1, METTL14, MEX3A, MFAP2, MFF, MFHAS1, MFNG, MFSD4, MGAT3, MIAT, MICALL2, MIDN, MIEF2, MIER1, MIIP, MIR1229, MIR1249, MIR135B, MIR1470, MIR219A2, MIR2861, MIR3188, MIR3190, MIR3191, MIR3193, MIR330, MIR3529, MIR3613, MIR365A, MIR3960, MIR4254, MIR4281, MIR4285, MIR4291, MIR4308, MIR4309, MIR4311, MIR4322, MIR4323, MIR4492, MIR4497, MIR4519, MIR4632, MIR4660, MIR4672, MIR4686, MIR4710, MIR4714, MIR4736, MIR4756, MIR4767, MIR4776-1, MIR4783, MIR5001, MIR548Z, MIR5689, MIR5690, MIR6515, MIR6763, MIR6789, MIR6790, MIR6813, MIR6843, MKL1, MKL2, MKNK2, MMP28, MOGAT1, MPHOSPH9, MPI, MPRIP, MPV17L2, MRPL11, MRPL20, MRPL34, MRPL41, MRPL48, MRPL54, MRPS12, MRPS15, MRPS17, MRPS25, MRPS5, MTFP1, MTFR2, MTPN, MTUS1, MTUS2, MUC12, MYBPC2, MYEOV2, MYH11, MYH9, MYL2, MYLK, MYO1B, MYOCD, MYRF, N4BP3, NAA35, NACC1, NACC2, NAE1, NANS, NAPA-AS1, NATD1, NCAN, NCMAP, NCOR2, NDE1, NDRG4, NDUFA3, NDUFA6, NDUFA6-AS1, NDUFA8, NDUFB4, NDUFS4, NEBL, NEBL-AS1, NEDD1, NEIL1, NEK6, NEK9, NEMF, NES, NEURL1B, NEUROG3, NFATC2, NFE2L3, NFIC, NGFRAP1, NIFK-AS1, NINJ1, NIPAL3, NIPAL4, NIPSNAP1, NKD1, NKX3-1, NLRP14, NLRX1, NMUR1, NOC2L, NOSIP, NPAS1, NPHP3, NPHP3-ACAD11, NPHP3-AS1, NPY4R, NR2C2AP, NR2E1, NR2E3, NR2F6, NR6A1, NRGN, NRROS, NRTN, NT5DC3, NTAN1, NTN1, NTN5, NTRK1, NUCKS1, NUDT21, NUDT3, NUDT8, NUP210, NUP210L, NWD1, NXPH3, NYAP1, OACYLP, OAS2, OCEL1, OCIAD2, OCSTAMP, OGDHL, OGFOD1, OLIG2, ONECUT3, OPCML, OPRL1, OR10H3, OR2D3, OR3A1, OSCAR, OSGIN1, OTUB2, OVOL3, P2RY6, PACSIN3, PADI4, PADI6, PAH, PAK4, PALM, PAPL, PAPLN, PAPPA, PAPPA-AS1, PAQR7, PARP15, PASK, PAWR, PC, PCDH12, PCGF6, PCSK4, PDE2A, PDE4A, PDE4C, PDE8A, PDGFD, PDGFRB, PDLIM1, PDLIM7, PEAR1, PEF1, PEX13, PEX5, PFDN4, PFKFB3, PFKFB4, PGAM5, PGAP2, PGLYRP2, PGPEP1, PHACTR3, PHACTR4, PHF19, PHLDA2, PHOSPHO1, PHYH, PHYKPL, PIANP, PIGB, PION, PITPNM1, PKD2L2, PKN1, PLA2R1, PLAGL2, PLAUR, PLCB3, PLCD1, PLCD3, PLD3, PLEKHA2, PLEKHJ1, PLIN3, PLIN5, PLK5, PLOD1, PLTP, PLXDC2, PLXNC1, PLXND1, PMVK, PNKP, PNPLA4, PNPLA5, PNPLA6, PNPLA7, POFUT1, POLG, POLR3K, POMGNT1, PON2, POP5, POU2F2, PPIA, PPM1H, PPP1R13L, PPP1R16A, PPP1R16B, PPP1R1A, PPP1R7, PPP2R1A, PPP2R5D, PPP4R1, PPP5C, PQLC3, PRCP, PRDM11, PRDM13, PRELID2, PRELP, PRKCD, PROCA1, PROSER2, PRPF40B, PRR15, PRR29, PRR5, PRRC1, PRRG2, PRRT3, PRX, PSIP1, PSMB4, PSMD9, PSMG3, PSMG3-AS1, PTGIS, PTGS1, PTP4A3, PTPDC1, PTPN1, PTPN11, PTPN3, PTPRA, PTPRS, PTPRU, PUS10, PVR, PVRL2, PXMP4, PYGM, PYGO1, PYROXD2, QPCT, QSOX2, R3HDML, RAB11FIP1, RAB1A, RAB25, RAB36, RAB39A, RAB3D, RAB3IL1, RAB4B, RAB4B-EGLN2, RAB8A, RABEP1, RABEPK, RAC1, RAC2, RAD21L1, RAI1, RALGAPB, RALY, RANBP3, RAP GAP, RARA, RARB, RARS, RASD2, RASGEF1A, RASGEF1C, RASGRP2, RASGRP4, RASSF7, RAX2, RBPMS, RBPMS2, RCAN2, RCAN3, RCAN3AS, RCC1, RCCD1, RCN3, RDH13, REEP6, RELB, REPIN1, REPS1, REXO1, RFX1, RGAG1, RGCC, RGS19, RHBDF2, RHBDL2, RHOD, RHOH, RHPN2, RILPL1, RILPL2, RIMS2, RIN1, RIN3, RIOK1, RIPPLY3, RITA1, RNF180, RNF187, RNF44, RNF6, RNU6-33P, RNU6-34P, ROM1, ROR1, RPA2, RPL18, RPL27A, RPL29, RPL4, RPN2, RPP25, RPS11, RPS18, RPS7, RPSAP58, RRM1, RRM2, RSPO4, RTBDN, RTDR1, RTN2, RXRA, RYR1, S100A3, S100A4, S1PR5, SAFB, SAFB2, SAMD4B, SARS2, SBF2-AS1, SCAP, SCML1, SCN1B, SCN8A, SCNN1B, SCNN1G, SCOC, SCRN1, SCRN2, SDC4, SDHAP3, SDK1, SEC14L5, SEC31B, SEMA4B, SEMA4G, SEMA6B, SEPT5, SEPT9, SEPW1, SERPINA1, SERPINB1, SERPINH1, SETD1A, SF3A2, SGK3, SGSM1, SGTA, SH2D2A, SH2D3A, SH2D3C, SH2D5, SH3BP2, SH3GLB2, SH3PXD2B, SHANK2, SHD, SHISA5, SHISA6, SHISA8, SIGLEC1, SIPA1L3, SIRPA, SIRT1, SIRT6, SLC12A3, SLC12A4, SLC13A3, SLC15A3, SLC16A6, SLC1A5, SLC1A6, SLC22A15, SLC22A23, SLC22A7, SLC25A17, SLC25A39, SLC25A42, SLC25A47, SLC29A3, SLC2A1, SLC2A10, SLC2A13, SLC2A1-AS1, SLC31A2, SLC35G1, SLC37A1, SLC38A10, SLC39A1, SLC39A10, SLC3A2, SLC43A1, SLC44A1, SLC52A3, SLC5A5, SLC6A1, SLC6A12, SLC6A2, SLC6A20, SLC6A4, SLC7A10, SLC7A2, SMIM2-AS1, SNHG5, SNN, SNORA45A, SNORD16, SNORD18A, SNORD50A, SNORD50B, SNPH, SNRNP25, SNUPN, SNX19, SNX22, SNX31, SOCS7, SOD3, SOGA1, SORBS1, SORBS2, SOWAHD, SOX2, SP6, SPAG1, SPAG9, SPATA2, SPHK2, SPIB, SPOCD1, SPTBN4, SPTBN5, SRC, SREBF1, SREBF2, SRPK1, SRPK2, SRRD, SRRT, SRSF12, SRXN1, SSBP4, SSC5D, SSH1, ST3GAL5, ST5, ST6GALNAC6, STARD4, STARD4-AS1, STPG1, STRA6, STRADA, STRBP, STRN3, STX1B, STXBP1, SULTIC2, SULT2B1, SULT4A1, SUOX, SUPT4H1, SUSD3, SWSAP1, SYCE2, SYCP3, SYMPK, SYN1, SYNE3, SYNGR1, SYNJ2, SYNPO2, SYNRG, SYT12, SYT2, SYT3, TADA1, TADA3, TAF1B, TAF6, TAF6L, TAGLN, TBC1D16, TBC1D2, TBX6, TBXA2R, TCEA2, TCERG1L, TCF3, TCIRG1, TCL1A, TCL1B, TCTA, TCTE1, TCTN3, TESC, TEX40, TFB1M, TFE3, TFF3, TGFB3, TGM6, TH, THEG, ThOP1, THPO, THUMPD2, TICAM1, TIGD1, TIMM10, TINAGL1, TJP3, TKT, TLE2, TLE6, TM9SF4, TMC6, TMC7, TMC8, TMED2, TMEM114, TMEM119, TMEM120A, TMEM147, TMEM14B, TMEM151A, TMEM161A, TMEM194B, TMEM200B, TMEM211, TMEM229B, TMEM30C, TMEM37, TMEM40, TMEM54, TMEM56, TMEM56-RWDD3, TMEM61, TMEM69, TMEM80, TMEM9, TMEM92, TMEM9B, TMEM9B-AS1, TMIGD2, TMPRSS13, TMPRSS2, TMPRSS6, TNC, TNFAIP8, TNFAIP8L1, TNFSF14, TNNT2, TNPO2, TNRC18, TNRC6B, TOPORS-AS1, TOR1AIP2, TOR1B, TP53I11, TP53RK, TPCN1, TPD52L1, TPM4, TPST2, TRAF1, TRAF5, TRAPPC12, TRAPPC3, TRIB3, TRIM26, TRIM32, TRIM56, TRIM59, TRIOBP, TRIT1, TRMT1, TRMT10C, TRPM6, TRPV4, TSC1, TSPO, TSSC1, TrC25, TTC28, TTC33, TTC38, TTC5, TTLL13, TTLL5, TTYH3, TUB, TUFM, TVP23A, TWSG1, TXN, TXNRD1, TYROBP, UBA1, UBA3, UBAC2, UBAC2-AS1, UBE2Q1, UBE2S, UBFD1, UBOX5, UBXN8, UPF1, UPK1A-AS1, UPK1B, USHBP1, USP35, UTP11L, VAT1L, VAV1, VEGFC, VPS37B, VPS37C, VPS37D, VPS52, VSTM2L, VSTM4, VWA8, VWA8-AS1, WARS, WASF2, WBSCR27, WDR25, WDR34, WDR38, WDR52, WDR78, WDR87, WIPF2, WIPF3, WISP1, WNT2B, WNT4, WRB, WSCD2, XKR7, XPO7, YBX2, YIF1A, YIF1B, YIPF1, ZBTB40, ZBTB47, ZCCHC14, ZCCHC18, ZCCHC8, ZDHHC12, ZDHHC24, ZFAND4, ZFP64, ZFYVE19, ZMIZ1, ZMIZ1-AS1, ZMYM6, ZMYM6NB, ZMYND8, ZNF135, ZNF142, ZNF214, ZNF234, ZNF236, ZNF24, ZNF296, ZNF335, ZNF337, ZNF423, ZNF500, ZNF536, ZNF579, ZNF592, ZNF606, ZNF613, ZNF646, ZNF668, ZNF687, ZNF689, ZNF710, ZNF792, ZNF839, ZNRF4, ZSWIM4, ZUFSP, ZWILCH GTF2I Targets Differentially-Expressed in iPSC:

ABCA7, ACTN3, ADAMTS10, ALDH18A1, ARL6IP5, ATP1A2, B3GALT5, B3GNT3, BCL7B, BEND4, BST2, CAPN2, CGN, CHST9, CILP2, CNTFR, CNTNAP1, CPT1C, CRABP1, CRLF1, CYP4F22, DAGLB, DPPA2, FAM65A, FZD2, GUCY2C, IL17RA, IQGAP2, KCNK6,

KLHL4, LAMC3, LITAF, LOC100130238, LTBP4, MEGF10, MEGF8, MEIS3, NTN1, NUP210, PAWR, PDLIM1, PLOD1, PLXND1, RASD2, RCN3, RHBDF2, RHOH, RPSAP58, RRM2, RYR1, S1PR5, SCAP, SEMA4B, SH2D3A, SHISA6, SLC5A5, STX1B, STXBP1, SYT2, TBC1D2, TCL1A, TLE2, TMEM151A, TMEM161A, TMEM92, TRIB3, TRIT1, UBXN8, VAT1L, VPS37D, WBSCR27.

Importantly, as shown in FIG. 3d, WBS lines retain only a subset of these core GTF2I targets, consistent with a progressive dosage-dependent loss of GTF2I occupancy. The inventors next confirmed by ChIP-qPCR (ChIP coupled with quantitative real-time PCR) dosage-dependent occupancy on a subset of core GTF2I targets. Additionally, they validated a generally lower enrichment, in WBS, for dosage sensitive targets, with levels of binding comparable to negative control regions (FIG. 16d).

Furthermore, the inventors found that GTF2I binds preferentially to bivalent domains (p-value<1,58e-03 for core targets and 1.13e-10 for all targets). Interestingly however, as previously reported[60,61], the distribution of GTF2I binding vis-à-vis the TSS does not correlate with expression (FIG. 3e, inner pie). Only a minority of total DEGs the inventors uncovered in iPSC are GTF2I-bound (~9%, with 3% being core GTF2I targets), and in turn only ~5% of the GTF2I targets are differentially expressed. Finally, within the proportion of DEGs that the inventors found attributable to GTF2I upon its knockdown, only 8% appear to be direct targets.

To understand the discrepancy between GTF2I transcriptional impact and occupancy, the inventors first explored the possibility that GTF2I dosage-dependent transcriptional dysregulation could be mediated by distal binding, looking at GTF2I-bound enhancers associated to putative target genes. The inventors found however only one of the 89 GTF2I-bound enhancers associated to a GTF2I-attributable, differentially-expressed TSS (PHC2), thus excluding that GTF2I acts mostly at enhancers, and supporting the alternative model of a largely indirect impact mediated by a minority of GTF2I direct targets. The inventors thus searched, among the direct GTF2I targets, for candidate transcription factors that could mediate its overall transcriptional impact, and identified BEND4, a TF that is both highly expressed in the brain and is part of a large CNV that has been reported in an ASD patient[62]. BEND4 was confirmed to be differentially expressed both between genotypes (FIG. 4a-b) and upon GTF2I knockdown using several independent short-hairpin expressing vectors (FIG. 4c-d-e). Strikingly, BEND4 and GTF2I levels are significantly anti-correlated in the human brain (Pearson coefficient of −0.71 between regional averages) according to a very recent compendium of gene expression across several brain regions from over a hundred individuals[63] (a weaker but significant correlation was also found among the regions of the Allen Brain Atlas)[64].

Next, in order to investigate whether GTF2I exerts its repressive effect on BEND4 through the LSD1 component of its associated repressive complex, the inventors tested the effect of LSD1 inhibition on the expression of BEND4 in differentiating iPSC. As shown in FIG. 4f, the inventors found that inhibition of LSD1 activity using two independent irreversible LSD1 inhibitors caused BEND4 upregulation, underscoring the functional impact of GTF2I-associated co-repressors on its target genes.

Thus, the inventors decided to profile LSD1 occupancy in iPSCs in order to test whether it could discriminate dosage-dependent and independent GTF2I targets. Comparison between the GTF2I and LSD1 profiles revealed that while GTF2I co-occupies only a relatively small fraction of the LSD1 targets (FIG. 3f), the inventors were able to detect significant LSD1 peaks on 53% of the GTF2I conserved peaks (FIG. 3g). Interestingly, although less than 11% of all DEGs are bound by LSD1, this proportion rises to 33% when considering only GTF2I-bound DEGs (p~3e-8) and the vast majority of these (78%) are downregulated upon increased GTF2I dosage, supporting a model in which LSD1 mediates an important part of the repressive activity of GTF2I.

Notably, LSD1-bound GTF2I dosage-sensitive targets include further disease-relevant genes, as in the paradigmatic case of CRB2 (FIG. 16d), which is implicated in cleft palate and lip development[65], and whose dosage sensitivity could provide a molecular link to the symmetrical phyltrum defects (respectively expanded or reduced) that are observed in WBS and 7dupASD patients.

Finally, the inventors extended their observations beyond the specific case of BEND4 (FIG. 4) in order to explore, on a genome-wide level, the potential utility of LSD1 specific inhibitors for reverting at least partially the molecular deficits attributable to increased 7q11.23 dosage. To this end they compared the transcriptomic impact, in their cohort of iPSC lines, of inhibiting LSD1 by stable RNA interference (RNAi) knock down versus irreversible chemical inhibitors. Interestingly, at a transcriptome-wide level, while LSD1 RNAi knock down lines clustered together rather than by genotype (ie. by 7q11.23 CNV), indicating a major global effect of this kind of LSD1 inhibition, iPSC lines treated with the LSD1 inhibitor still clustered with the corresponding cell line treated with vehicle (DMSO) (FIG. 4g). This result indicates that the chemical inhibition of LSD1 has a less dramatic effect on the overall transcriptome compared to the knock down achieved by the stable integration of RNAi vectors (FIG. 4h), preserving the transcriptional identity of individual cell lines by likely effecting more selective transcriptional changes through more specific targets. They thus examined what portion of the differentially expressed genes imputable to GTF2I (as they were identified in the GTF2I knock-down experiment) also changes upon LSD1 inhibition. Analysis from the first 2 inhibited samples uncovered that 30 genes fall into this category (using a false discovery rate "FDR" of 0.07 and a threshold of fold change >1.15) (FIG. 4i), with many of them belonging to highly specific gene ontology categories including: positive regulation of phosphorylation (IGF1R, CDH2, ARRB1, NRK, EPHA4, IGFBP3), nervous system development (IGF1R, CDH2, SERINC5, PRICKLE1, NLGN2, PTPRD, COX7B, ADCY1, MAP2, EPHA4, COL9A1), and neuron projection morphogenesis (IGF1R, PTPRD, ADCY1, MAP2, EPHA4, COL9A1). Importantly, a significant portion of the genes included in this list (about 60%) becomes upregulated upon LSD1 inhibition in accordance with the transcriptional repressive activity of LSD1 on lysine 4 of histone H3 tails. Furthermore, these LSD1-sensitive targets also include critical genes that have already been causally associated to ASD, such as NLGN2, MAP2, and PRICKLE1. Interestingly however, within this subset of LSD1-sensitive targets, only RHBDF2 has a GTF2I peak on its promoter. This may indicate the presence of distal enhancer-based regulation by GTF2I-LSD1 (that escapes a promoter-centered analysis), or the possibility that in addition to its role in GTF2I-containing complexes, chemical LSD1-inhibition can rescue several important genes found differentially-expressed in the diseases, even when they are only indirectly modulated by GTF2I (FIG. 4i).

Example 7: iPSC-Specific Transcriptional Dysregulation is Amplified During Development in a Lineage-Specific Manner That 7q11.23 CNVs trigger disease-relevant transcriptional dysregulation already at the pluripotent state suggests that these initial conditions may prime the accumulation of even greater transcriptional alterations during development. Further, it predicts that the aggregate dysregulation in iPSC across categories spanning several developmental pathways and organ systems will be channeled upon differentiation, resulting in the selective amplification of specific domains of iPSC-specific dysregulation in a lineage-dependent fashion.

In order to test this hypothesis, the inventors differentiated the present invention's iPSC lines into three lineages of cardinal relevance for the two conditions (FIG. 5a): i) Pax6+ telencephalic neural stem cells and progenitors (NPC)[30,31]; ii) neural crest stem cells (NCSC)[32], which originate the craniofacial structures along with several other disease-relevant lineages; iii) mesenchymal stem cells (MSC)[32], hierarchically upstream of osteocytes, chondrocytes, smooth muscle cells, and other physiopathologically meaningful cell types.

The inventors confirmed that patient-derived NPCs expressed key forebrain markers such as FOXG1, OTX2 and ZO1, and were typically arranged in neural rosettes with TBR2+ intermediate progenitors surrounding apical Pax6+ progenitors (FIG. 5b). The inventors profiled 15 patient and control-derived NPC lines and found that most of the differentially expressed genes were enriched in GO categories related to neuronal function such as axon guidance, regulation of transmitter secretion and negative regulation of axonogenesis (FIG. 5c).

In parallel, the inventors differentiated the same cohort of iPSC lines into NCSC that displayed distinct morphology (FIG. 17a), and stained homogeneously positively for HNK1 and NGFR, a defining combination of NCSC markers, both in immunofluorescence (FIG. 17c) and by flow cytometry (FIG. 5d and FIG. 17d). Transcriptional profiling revealed differential expression in 364 genes (GO enrichments shown in FIG. 5e), including key genes linked to craniofacial dysmorphisms (ATP2C1, HHAT, LMNB1, MAPK8, PTCH1 and SATB2)[66-73] and RhoA Signalling/Signalling by Rho Family GTPases (WASF1, GFAP, ACTR2, STMN1, MAPK8, ARHGEF11 and PLXNA1)[74, 75]. Importantly, small GTPase RhoA signalling has been recently showed to rescue SM-actin filament bundle formation of smooth muscle cells in a model of WBS[76].

Finally, to define the impact of iPSC-primed transcriptional dysregulation upon further differentiation, the inventors induced patient-derived NCSC towards the MSC fate, characterized by a typical MSC-like morphology (FIG. 17b) and the expression of key MSC markers CD44 and CD73 (<95%) (FIG. 5f and FIG. 17e). Transcriptomic profiling confirmed that, with the notable exception of ELN, also in MSC expression of 7q11.23 genes recapitulated dosage (FIG. 17f), and yielded 422 DEGs showing enrichment for several GO categories related to tissue morphology (FIG. 5g). Although shuffling tests (see methods) yielded enrichments in some of these categories, removal of these potentially spurious genes left unchanged the main categories enriched among DEGs (Supplementary Table 7). Remarkably, samples clustered by genotype at the whole transcriptome level (FIG. 5h), indicating that 7q11.23 dosage imbalances have an especially high penetrance at this developmental stage. Strikingly, the atypical sample (AtWBS1-C2) clustered with the controls, suggesting that spared genes are particularly important in this lineage, in line with recent reports of the role of BAZ1B in neural crest migration[36]. Moreover, an Ingenuity Pathway Analysis (IPA) on DEGs between WBS and CTL revealed a molecular network (the highest ranking network) enriched for genes related to cardiovascular system development (FIG. 5i) and including key regulators of cardiovascular development (FIG. 5j).

Given the physiopathological significance of the transcriptional dysregulation in MSC, the inventors next asked what proportion of MSC-specific DEGs were also impacted at the iPSC state. As shown in FIG. 6a, 18% of MSC DEGs were already differentially-expressed in iPSC (25% when excluding external control iPSC), and the overlap steadily increases as the inventors considered MSC DEGs with a higher expression in MSC, with 45% of the MSC DEGs expressed above 50 FPKM (Fragments Per Kilobase of exon per Million fragments mapped) being found affected also in iPSC (FIG. 18a). Interestingly however, the proportion of overlapping DEGs did not correlate with expression at the iPSC stage (FIG. 18b), arguing against the hypothesis of greater accuracy at higher expression levels. The inventors therefore hypothesized that genes that are dysregulated both in iPSC and MSC would be preferentially those that are specifically activated upon differentiation to MSC. Indeed, the inventors found that of the iPSC DEGs that are down-regulated upon differentiation to MSC (over 60%), very few remain differentially expressed also in MSC (FIG. 18c). In contrast, as the inventors consider iPSC DEGs that increase expression upon differentiation to MSC, the proportion of DEGs maintained also in MSC rises to nearly 30%. On the basis of this analysis, the inventors next hypothesized that the subset of iPSC DEGs that is conserved upon differentiation in each given lineage should be preferentially enriched in lineage-relevant categories. The inventors thus evaluated, for each of the three differentiated lineages under study, the proportion of DEGs conserved for the GO categories that had been found enriched already in iPSC. As shown in FIG. 6b-c-d and schematically represented in FIG. 7a, upon differentiation iPSC DEGs are preferentially retained by category in a lineage-appropriate manner so that, for each target lineage, the proportion of conserved iPSC DEGs is much greater in categories relevant to that lineage (such as axonogenesis and axon guidance in the neural lineage, synapse-related categories in NCSC that will originate the peripheral nervous system and smooth muscle related categories in MSC).

Finally, the inventors noted that the proportion of symmetrically dysregulated genes is significantly higher among the DEGs that are in common between iPSC and differentiated lineages (average odd ratio~1.75, p~5e-03 evaluated from lineage-specific Chi-squared tests compounded through Fisher's method), supporting the notion that symmetrical patterns, likely under more direct control by 7q11.23 dosage, are particularly relevant for the quota of disease-relevant transcriptional dysregulation that is seeded already in the pluripotent state.

Example 8: A Web Platform for 7q11.23 CNV Syndromes

Finally, the inventors designed a new web platform called WikiWilliamns-7qGeneBase to make their data accessible to the community of scientists and practitioners working on these two diseases, through a user-friendly, gene-centered interface. Besides integrating, in a multi-layered manner, all their results with data from the literature, WikiWilliamns is open to contributions by other groups through submission to the database's curators, with the aim of assembling in one site all molecular data on 7q11.23 syndromes (FIG. 7b and FIG. 19). The platform is openly accessible at http://bio.ieo.eu/wbs/.

Example 9: An Approach to Isolate iPSC-Derived FOXG1-Expressing Cortical Progenitors The proof of principle of experiments aimed at isolating cortical progenitors by selection and FACS sorting is described in FIG. 8. Briefly, the inventors designed a lentiviral construct that expresses GFP from a ubiquitous promoter and the puromycinr esistance gene under the control of the FOXG1 promoter. The figure shows the infection of a control iPSC line (reprogrammed from a WBS patient relative) with different concentrations of this lentiviral vector, and the assessment of infection efficiency by GFP fluorescence (both by immunofluorescence and FACS).

Example 10: The Screening Assay Based on qRT-PCR

The inventors have already validated the automated workflow for the scoring of the expression of GTF2I and BAZ1B (by multiplex qRT-PCR) in iPSC grown on a 96-well format (FIG. 9). This is the format in which the screening will be conducted. The inventors were able to measure consistently the levels of GTF2I across 3 different concentrations of seeded iPSC (from 6.000 to 12.000), finding the expected linear relationship between number of cells and GTF2I expression, with excellent consistency across different wells of the same plate. Even across wells from different plates, qRT-PCR measurements are extremely consistent. The quantification shows a minimal coefficient of variation (CV) across both intra- and inter-plate measurements.

Example 11: Establishment of NGN2-Transduced Clonal Cell Lines

The inventors modified the protocol for the direct differentiation of iPSCs towards the cortical glutamatergic lineage via induction of a lentivirally transduced factor, NGN2[34]. Briefly, the original protocol employs two lentiviral vectors to integrate i) the inducible tetracyclin transactivator (rtTA) constitutively expressed under the UbC promoter and ii) an NGN2-EGFP-Puro polypeptide-encoding cDNA whose transcription is driven by the transactivator in the presence of doxycylin. The advantage in the use of this protocol lies in its simplicity, its rapidity and the homogeneity of the resulting differentiated population. To further enhance these characteristics and enable for scaling up neuronal production (for high throughput screenings that require large amounts of homogeneous neurons) the inventors have devised a strategy to establish clonal cell lines that are readily inducible by the addition of doxycylin in the medium. Clones are established by: i) sorting a co-infected iPSC population into a 96-well plate; ii) selecting and expanding colonies with an ES-like (undifferentiated) morphology; iii) splitting selected colonies in two wells and testing one for GFP expression upon induction; iv) expanding and stocking 3-5 GFP positive iPSCs lines.

Such lines have been tested for differentiation (up until day 21 from induction) and display the same mature neuronal markers, including glutamatergic markers, regardless of the genotype (FIG. 11).

Discussion

The inventors chose the paradigmatic pair of genetic syndromes caused by symmetrical 7q11.23 CNV 7q11.23 in order to test the potential of iPSCs for defining how gene dosage impacts disease-relevant pathways in early developmental lineages. Their findings have broad significance for the molecular pathogenesis of WBS and 7dupASD as well as for the reprogramming-based disease modeling field as a whole.

First, variability has been recently recognized as a key concern for iPSC-based disease modeling, inviting caution in the interpretation of results from few lines that do not adequately sample variability either across individuals or across lines reprogrammed from the same individual[1]. Thus, by presenting the largest cohort of iPSC lines characterized so far for any single genetic condition, combined to the first large scale use of mRNA-based integration-free reprogramming, the present invention benchmarks the possibility of detecting robust dosage-dependent alterations in transcriptional programs, even when these are caused by subtle dosage imbalances.

Second, the size and quality of the present invention's iPSC cohort permitted two key observations on the molecular impact of 7q11.23 CNV: i) that these caused significant transcriptional dysregulation in disease-relevant pathways already in the pluripotent state; and ii) that this dysregulation was selectively amplified in a lineage-specific manner, with disease-relevant pathways preferentially and progressively more affected in differentiated lineages matching specific disease domains. The significance of this observation for the iPSC modeling field lies in the fact that the pluripotent state is by far the best characterized and most standardized one among the human developmental stages captured in vitro. Importantly, it is also the most amenable to high-throughput upscaling. Hence, the observation that the pluripotent state is not only a viable stage in which to measure disease-relevant transcriptional effects of genetic alterations, but that these effects are also predictive of further dysregulation in differentiated lineages, grounds the feasibility of middle-to-high-throughput iPSCs characterization in order to functionally annotate human genomes, prior to selecting lines and assays for more labor-intensive differentiation courses.

In terms of the molecular pathogenesis of WBS and 7dupASD, besides uncovering the impact of 7q11.23 dosage already in the pluripotent state, these results also provide a first entry point for the molecular dissection of the outstanding feature that characterizes these two conditions, namely the coexistence, in the face of symmetrically opposite CNV, of both shared and symmetrically opposite phenotypes. By analyzing many samples from both conditions, the inventors were in fact able to define a subset of DEGs that follows a symmetrically opposite dosage-dependent trend. Importantly, the inventors found that this quota is significantly retained upon differentiation, indicating that symmetrically opposite patterns of gene expression seeded already in the pluripotent state, likely under direct control of 7q11.23 dosage, become increasingly prominent in disease-relevant differentiated lineages, thus providing a strong rationale for studying these two diseases (and by implication other CNV-based symmetric disease pairs) together. Importantly, inventors' analysis of symmetrically dsyregulated targets also uncovered the following genes as prime candidates for mediating the molecular pathogenesis of defining aspects of the two conditions: i) PDLIM1, which has been associated to attention-deficit disorder, neurite outgrowth, cardiovascular defects, and hyperacusis; ii) MYH14, which was involved in hearing impairment; iii) BEND4, a transcription factor harboring the BEN domain that distinguishes a recently characterized family of neural repressors, and that was sensitive to both GTF2I dosage and its LSD1-mediated repressive activity, a finding that resonates also with the inversely correlated pattern of GTF2I and BEND4 gene expression in the human brain.

Third, both epidemiological data from atypical patients as well as mouse studies had pointed to GTF2I as one of the key genes mediating the phenotypes of the two conditions, especially as far as the cognitive behavioral aspects are concerned. By selectively rescuing GTF2I levels in the background of the three 7q11.23 genotypes and profiling GTF2I genome-wide occupancy across the heterogeneity of human samples, the inventors provide a mechanistic dissection of its contribution, finding that GTF2I accounts, mostly indirectly, for a significant and specific proportion of 7q11.23 dosage-dependent transcriptional impact. Importantly, the inventors found that in the human pluripotent state GTF2I assembles a chromatin repressive complex with LSD1 and HDAC2 and binds preferentially to bivalent chromatin promoters, whose timed resolution has been shown by us and several other groups to be essential for normal development, especially along the neural lineage$^{77\text{-}80}$. This provides the conceptual and experimental framework to investigate the epigenetic and transcriptional impact on GTF2I dosage-dependent targets through development. This result also confirm that LSD1 inhibitors and/or HDAC2 inhibitors may be used for the prevention and/or treatment of a neurodevelopmental disorder entailing intellectual disability (ID) and/or belonging to the Autism Spectrum Disorder (ASD) and/or Schizophrenia (SZ).

Finally, the inventors provide a user-friendly, open source web platform in which the inventors assembled the multi-layered datasets from this first cohort of WBS and 7dupASD samples, and which was designed to integrate ongoing contributions from the entire scientific community working on these two diseases, thus serving also as a first template for data sharing from iPSC-based functional genome annotation.

REFERENCES

1. Cahan, P. & Daley, G. Q. Origins and implications of pluripotent stem cell variability and heterogeneity. *Nat Rev Mol Cell Biol* 14, 357-68 (2013).
2. Prilutsky, D. et al. iPSC-derived neurons as a higher-throughput readout for autism: promises and pitfalls. *Trends Mol Med* 20, 91-104 (2014).
3. Ghosh, A., Michalon, A., Lindemann, L., Fontoura, P. & Santarelli, L. Drug discovery for autism spectrum disorder challenges and opportunities. *Nat Rev Drug Discov* 12, 777-90 (2013).
4. Marchetto, M. C. et al. A model for neural development and treatment of Rett syndrome using human induced pluripotent stem cells. *Cell* 143, 527-39 (2010).
5. Pasca, S. P. et al. Using iPSC-derived neurons to uncover cellular phenotypes associated with Timothy syndrome. *Nat Med* 17, 1657-62 (2011).
6. Chailangkarn, T., Acab, A. & Muotri, A. R. Modeling neurodevelopmental disorders using human neurons. *Curr Opin Neurobiol* 22, 785-90 (2012).
7. Kim, K. Y., Jung, Y. W., Sullivan, G. J., Chung, L. & Park, I. H. Cellular reprogramming: a novel tool for investigating autism spectrum disorders. *Trends Mol Med* 18, 463-71 (2012).
8. Sanders, S. J. et al. Multiple recurrent de novo CNVs, including duplications of the 7q11.23 Williams syndrome region, are strongly associated with autism. *Neuron* 70, 863-85 (2011).
9. Pober, B. R. MEDICAL PROGRESS Williams-Beuren Syndrome (vol 362, pg 239, 2010). New England *Journal of Medicine* 362, 2142-2142 (2010).
10. Somerville, M. J. et al. Severe expessive-language delay related to duplication of the Williams-Beuren locus. *N Engl J Med* 353, 1694-701 (2005).
11. Merla, G., Brunetti-Pierri, N., Micale, L. & Fusco, C. Copy number variants at Williams-Beuren syndrome 7q11.23 region. *Human Genetics* 128, 3-26 (2010).
12. Van der Aa, N. et al. Fourteen new cases contribute to the characterization of the 7q11.23 microduplication syndrome. *Eur J Med Genet* 52, 94-100 (2009).
13. Osborne, L. R. Animal Models of Williams Syndrome. *American Journal of Medical Genetics Part C-Seminars in Medical Genetics* 154C, 209-219 (2010).
14. Mervis, C. B. et al. Duplication of GTF2I results in separation anxiety in mice and humans. *American journal of human genetics* 90, 1064-70 (2012).
15. O'Leary, J. & Osborne, L. R. Global analysis of gene expression in the developing brain of Gtf2ird1 knockout mice. *PLoS One* 6, e23868 (2011).
16. Campuzano, V. et al. Reduction of NADPH-oxidase activity ameliorates the cardiovascular phenotype in a mouse model of Williams-Beuren Syndrome. *PLoS Genet* 8, e1002458 (2012).
17. Pinto, D. et al. Convergence of genes and cellular pathways dysregulated in autism spectrum disorders. *Am J Hum Genet* 94, 677-94 (2014).
18. Jeste, S. S. & Geschwind, D. H. Disentangling the heterogeneity of autism spectrum disorder through genetic findigs. *Nat Rev Neurol* 10, 74-81 (2014).
19. Spooren, W., Lindemann, L., Ghosh, A. & Santarelli, L. Synapse dysfunction in autism: a molecular medicine approach to drug discovery in neurodevelopmental disorders. *Trends Pharmacol Sci* 33, 669-84 (2012).
20. Krumm, N., O'Roak, B. J., Shendure, J. & Eichler, E. E. A de novo convergence of autism genetics and molecular neuroscience. *Trends Neurosci* 37, 95-105 (2014).
21. Dokmanovic, M., Clarke, C. & Marks, P. A. Histone deacetylase inhibitors: overview and perspectives. *Mol Cancer Res* 5, 981-9 (2007).
22. Kim, H. J. & Bae, S. C. Histone deacetylase inhibitors: molecular mechanisms of action and clinical trials as anti-cancer drugs. *Am J Transl Res* 3, 166-79 (2011).
23. Takahashi, K. et al. Induction of pluripotent stem cells from adult human fibroblasts by defined factors. *Cell* 131, 861-72 (2007).
24. Blecher-Gonen, R. et al. High-throughput chromatin immunoprecipitation for genome-wide mapping of in vivo protein-DNA interactions and epigenomic states. *Nat Protoc* 8, 539-54 (2013).
25. Shevchenko, A., Wilm, M., Vorm, O. & Mann, M. Mass spectrometric sequencing of proteins silver-stained polyacrylamide gels. *Anal Chem* 68, 850-8 (1996).
26. Rappsilber, J., Ishihama, Y. & Mann, M. Stop and go extraction tips for matrix-assisted laser desorption/ionization, nanoelectrospray, and LC/MS sample pretreatment in proteomics. *Anal Chem* 75, 663-70 (2003).
27. Keller, A., Nesvizhskii, A. I., Kolker, E. & Aebersold, R. Empirical statistical model to estimate the accuracy of peptide identifications made by MS/MS and database search. *Anal Chem* 74, 5383-92 (2002).

28. Nesvizhskii, A. I., Keller, A., Kolker, E. & Aebersold, R. A statistical model for identifying proteins by tandem mass spectrometry. *Anal Chem* 75, 4646-58 (2003).

29. Adamo, A. et al. LSD1 regulates the balance between self-renewal and differentiation in human embryonic stem cells. *Nat Cell Biol* 13, 652-9 (2011).

30. Shi, Y., Kirwan, P. & Livesey, F. J. Directed differentiation of human pluripotent stem cells to cerebral cortex neurons and neural networks. *Nat Protoc* 7, 1836-46 (2012).

31. Shi, Y., Kirwan, P., Smith, J., Robinson, H. P. & Livesey, F. J. Human cerebral cortex development from pluripotent stem cells to functional excitatory synapses. *Nat Neurosci* 15, 477-86, S1 (2012).

32. Menendez, L. et al. Directed differentiation of human pluripotent cells to neural crest stem cells. *Nat Protoc* 8, 203-12 (2013).

33. Pang, Z. P., Cao, P., Xu, W. & Sudhof, T. C. Calmodulin controls synaptic strength via presynaptic activation of calmodulin kinase II. *J Neurosci* 30, 4132-42 (2010).

34. Zhang, Y. et al. Rapid single-step induction of functional neurons from human pluripotent stem cells. *Neuron* 78, 785-98 (2013).

35. Fusco, C. et al. Smaller and larger deletions of the Williams Beuren syndrome region implicate genes involved in mild facial phenotype, epilepsy and autistic traits. *Eur J Hum Genet* 22, 64-70 (2014).

36. Barnett, C. et al. Williams Syndrome Transcription Factor is critical for neural crest cell function in *Xenopus laevis*. *Mech Dev* 129, 324-38 (2012).

37. Donaudy, F. et al. Nonmuscle myosin heavy-chain gene MYH14 is expressed in cochlea and mutated in patients affected by autosomal dominant hearing impairment (DFNA4). *Am J Hum Genet* 74, 770-6 (2004).

38. Warren, L. et al. Highly efficient reprogramming to pluripotency and directed differentiation of human cells with synthetic modified mRNA. *Cell Stem Cell* 7, 618-30 (2010).

39. Pasi, C. E. et al. Genomic instability in induced stem cells. *Cell Death Differ* 18, 745-53 (2011).

40. Abyzov, A. et al. Somatic copy number mosaicism in human skin revealed by induced pluripotent stem cells. *Nature* 492, 438-42 (2012).

41. Antonell, A. et al. Partial 7q11.23 deletions further implicate GTF2I and GTF2IRD1 as the main genes responsible for the Williams-Beuren syndrome neurocognitive profile. *J Med Genet* 47, 312-20 (2010).

42. Edelmann, L. et al. An atypical deletion of the Williams-Beuren syndrome interval implicates genes associated with defective visuospatial processing and autism. *J Med Genet* 44, 136-43 (2007).

43. Hirota, H. et al. Williams syndrome deficits in visual spatial processing linked to GTF2IRD1 and GTF2I on chromosome 7q11.23. *Genet Med* 5, 311-21 (2003).

44. Lazebnik, M. B., Tussie-Luna, M. I., Hinds, P. W. & Roy, A. L. Williams-Beuren syndrome-associated transcription factor TFII-I regulates osteogenic marker genes. *J Biol Chem* 284, 36234-9 (2009).

45. Sakurai, T. et al. Haploinsufficiency of Gtf2i, a gene deleted in Williams Syndrome, leads to increases in social interactions. *Autism Res* 4, 28-39 (2011).

46. Kruse, K., Pankau, R., Gosch, A. & Wohlfahrt, K. Calcium metabolism in Williams-Beuren syndrome. *J Pediatr* 121, 902-7 (1992).

47. Gothelf, D., Farber, N., Raveh, E., Apter, A. & Attias, J. Hyperacusis in Williams syndrome: characteristics and associated neuroaudiologic abnormalities. *Neurology* 66, 390-5 (2006).

48. Kern, J. K. et al. The pattern of sensory processing abnormalities in autism. *Autism* 10, 480-94 (2006).

49. Pankau, R., Partsch, C. J., Winter, M., Gosch, A. & Wessel, A. Incidence and spectrum of renal abnormalities in Williams-Beuren syndrome. *Am J Med Genet* 63, 301-4 (1996).

50. Wang, K. S., Liu, X., Zhang, Q., Aragam, N. & Pan, Y. Parent-of-origin effects of FAS and PDLIM1 in attention-deficit/hyperactivity disorder. *J Psychiatry Neurosci* 37, 46-52 (2012).

51. Ohno, K., Kato, H., Funahashi, S., Hasegawa, T. & Sato, K. Characterization of CLP36/Elfn/PDLIM1 in the nervous system. *J Neurochem* 111, 790-800 (2009).

52. Antonell, A., Vilardell, M. & Perez Jurado, L. A. Transcriptome profile in Williams-Beuren syndrome lymphoblast cells reveals gene pathways implicated in glucose intolerance and visuospatial construction deficits. *Hum Genet* 128, 27-37 (2010).

53. Ferrero, G. B. et al. An atypical 7q11.23 deletion in a normal IQ Williams-Beuren syndrome patient. *Eur J Hum Genet* 18, 33-8 (2010).

54. Morris, C. A. et al. GTF2I hemizygosity implicated in mental retardation in Williams syndrome: genotype-phenotype analysis of five families with deletions in the Williams syndrome region. *Am J Med Genet A* 123A, 405-59 (2003).

55. Gocke, C. B. & Yu, H. ZNF198 stabilizes the LSD1-CoREST-HDAC1 complex on chromatin through its MYM-type zinc fingers. *PLoS One* 3, e3255 (2008).

56. Hakimi, M. A., Dong, Y., Lane, W. S., Speicher, D. W. & Shiekhattar, R. A candidate X-linked mental retardation gene is a component of a new family of histone deacetylase-containing complexes. *J Biol Chem* 278, 7234-9 (2003).

57. Ming, G. L. et al. Cellular Reprogramming: Recent Advances in Modeling Neurological Diseases. *J Neurosci* 31, 16070-16075 (2011).

58. Yang, P. et al. RCOR2 is a subunit of the LSD1 complex that regulates ESC property and substitutes for SOX2 in reprogramming somatic cells to pluripotency. *Stem Cells* 29, 791-801 (2011).

59. Chimge, N. O., Makeyev, A. V., Ruddle, F. H. & Bayarsaihan, D. Identification of the TFII-I family target genes in the vertebrate genome. *Proc Natl Acad Sci, USA* 105, 9006-10 (2008).

60. Makeyev, A. V. et al. Diversity and complexity in chromatin recognition by TFII-I transcription factors in pluripotent embryonic stem cells and embryonic tissues. *PLoS One* 7, e44443 (2012).

61. Fan, A. X. et al. Genomic and proteomic analysis of transcription factor TFII-I reveals insight into the response to cellular stress. *Nucleic Acids Res* (2014).

62. Sabaratnam, M., Turk, J. & Vroegop, P. Case report: autistic disorder and chromosomal abnormality 46, XX duplication (4) p12-p13. *Eur Chld Adolesc Psychiatry* 9, 307-11 (2000).

63. Ramasamy, A. et al. Genetic variability in the regulation of gene expression in ten regions of the human brain. *Nat Neurosci* 17, 1418-28 (2014).

64. Hawrylycz, M. J. et al. An anatomically comprehensive atlas of the adult human brain transcriptome. *Nature* 489, 391-9 (2012).

65. Letra, A. et al. Follow-up association studies of chromosome region 9q and nonsyndromic cleft lip/palate. *Am J Med Genet A* 152A, 1701-10 (2010).
66. Bonilla-Claudio, M. et al. Bmp signaling regulates a dose-dependent transcriptional program to control facial skeletal development. *Development* 139, 709-19 (2012).
67. Cobourne, M. T. et al. Sonic hedgehog signalling inhibits palatogenesis and arrests tooth development in a mouse model of the nevoid basal cell carcinoma syndrome. *Dev Biol* 331, 38-49 (2009).
68. Dennis, J. F. et al. Mutations in Hedgehog acyltransferase (Hhat) perturb Hedgehog signaling, resulting in severe acrania-holoprosencephaly-agnathia craniofacial defects. *PLoS Genet* 8, e1002927 (2012).
69. Dobreva, G. et al. SATB2 is a multifunctional determinant of craniofacial patterning and osteoblast differentiation. *Cell* 125, 971-86 (2006).
70. Kurosaka, H., Iulianella, A., Williams, T. & Trainor, P. A. Disrupting hedgehog and WNT signaling interactions promotes cleft lip pathogenesis. *J Clin Invest* 124, 1660-71 (2014).
71. Metzis, V. et al. Patched1 is required in neural crest cells for the prevention of orofacial clefs. *Hum Mol Genet* 22, 5026-35 (2013).
72. Singh, S., Yin, X., Pisano, M. M. & Greene, R. M. Molecular profiles of mitogen activated protein kinase signaling pathways in orofacial development. *Birth Defects ResA Clin Mol Teratol* 79, 35-44 (2007).
73. Zhao, X. et al. The role of SATB2 in skeletogenesis and human disease. *Cytokune Growth Factor Rev* 25, 35-44 (2014).
74. Minoux, M. & Rijli, F. M. Molecular mechanisms of cranial neural crest cell migration and patterning in craniofacial development. *Development* 137, 2605-21 (2010).
75. Phillips, H. M. et al. Neural crest cell survival is dependent on Rho kinase and is required for development of the mid face in mouse embryos. *PLoS One* 7, e37685 (2012).
76. Ge, X. et al. Modeling supravalvular aortic stenosis syndrome with human induced pluripotent stem cells. *Circulation* 126, 1695-704 (2012).
77. Burgold, T. et al. The H3K27 Demethylase JMJD3 is Required for Maintenance of the Embryonic Respiratory Neuronal Network, Neonatal Breathing, and Survival. *Cell Rep* 2, 1244-58 (2012).
78. Mohn, F. et al. Lineage-specific polycomb targets and de novo DNA methylation define restriction and potential of neuronal progenitors. *Mol Cell* 30, 755-66 (2008).
79. Burgold, T. et al. The histone H3 lysine 27-specific demethylase Jmjd3 is required for neural commitment. *PLoS One* 3, e3034 (2008).
80. Bernstein, B. E. et al. A bivalent chromatin structure marks key developmental genes in embryonic stem cells. *Cell* 125, 315-26 (2006).

---

The invention claimed is:

1. A method of preventing and/or treating an at least one behavior-cognitive defect in an individual with a copy number variation (CNV) at 7q11.23, comprising:
   administering an LSD1 inhibitor to said individual; wherein the said administration disrupts the transcriptional repressive activity of LSD1 on lysine 4 of histone H3 tails;
   wherein the degree of LSD1 inhibition sufficiently reduces the function of the GTF2I transcriptional co-repressor complex;
   wherein the disruption of GTF2I function increases BEND4 upregulation;
   wherein genes which are imputable to GTF2I also change expression significantly upon LSD1 inhibition, such as but not limited to expression of one or more of IGF1R, SDH2, ARRB1, NRK, EPHA4, IGFBP3, SERINC5, PRICKLE1, NLGN2, PTPRD, COX7B, ADCY1, MAP2, EDHA4, and COL9A1, or any combination therein.

2. The method of claim 1, wherein the subject has an intellectual disability and/or Autism Spectrum Disorder.

3. The method of claim 1, wherein the copy number variations (CNV) at 7q11.23 causes 7dupASD.

4. The method of claim 1, wherein the copy number variations (CNV) at 7q11.23 causes a 7q11.23 microduplication-dependent Schizophrenia.

5. The method of claim 1, wherein the LSD1 inhibitor is N-[4-[trans-2-aminocyclopropyl]phenyl]-3-(2-oxooxazolidin-3-yl)benzamide hydrochloride.

6. The method of claim 1, wherein the LSD1 inhibitor is (trans)-N1-((1R, 2S)-2-phenylcyclopropyl)cyclohexane-1, 4-diamine hydrochloride.

7. The method of claim 1, wherein treatment with the LSD1 inhibitor significantly increases expression of one or more of IGFBP3, ANXA2, MAP2, ELF3, EPHA4, ATP2A3, PRICKLE1, NRK, CDH2, IGFBP5, GLDC, DPPA2, ARRB1, SERINC5, COL9A1, or COX7B.

8. The method of claim 1, wherein treatment with the LSD1 inhibitor significantly decreases expression of one or more of NLGN2, MYSM1, PTPRD, ATAD5, IGF1R, or RHBDF2.

9. The method of claim 1, wherein treatment with the LSD1 inhibitor significantly alters expression of one or more of NACAD, JAZF1, ADCY1, ZNF578, NID1, ITPR2, FOXN3, or FAM189A2.

10. The method of claim 1, wherein the at least one behavioral-cognitive defect is selected from the group consisting of autistic-like behaviors, attention deficit hyperactivity disorder (ADHD), language impairment, anxiety, intellectual disability, global developmental delay, learning difficulties, impairment in adaptive behavior, language delay, oral motor and speech sound delay, oral motor and speech sound disorder, social anxiety, separation anxiety, social phobia, autism spectrum disorder (ASD), selective mutism, oppositional defiant disorder (ODD), repetitive behaviors/movements, stereotypies, compromised visuomotor integration, social communication impairment/deficits or any combination thereof.

* * * * *